(12) United States Patent
Heckmeier et al.

(10) Patent No.: US 7,033,652 B2
(45) Date of Patent: Apr. 25, 2006

(54) LIQUID-CRYSTALLINE MEDIUM

(75) Inventors: Michael Heckmeier, Hemsbach (DE); Martin Engel, Darmstadt (DE); Brigitte Schuler, Grossostheim (DE); Volker Reiffenrath, Rossdorf (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 10/290,292

(22) Filed: Nov. 8, 2002

(65) Prior Publication Data

US 2003/0186002 A1    Oct. 2, 2003

(30) Foreign Application Priority Data

Nov. 9, 2001    (DE) ................. 101 55 079

(51) Int. Cl.
*C09K 19/12*    (2006.01)
*C09K 19/34*    (2006.01)
*C09K 19/30*    (2006.01)
*C09K 19/52*    (2006.01)
*C07C 25/02*    (2006.01)

(52) U.S. Cl. ............. 428/1.1; 252/299.01; 252/299.61; 252/299.63; 252/299.66; 570/127; 570/129

(58) Field of Classification Search .......... 252/299.66, 252/299.01, 299.61, 299.63; 428/1.1; 570/127, 570/129
See application file for complete search history.

(56) References Cited

FOREIGN PATENT DOCUMENTS

| DE | 30 22 818 | 1/1982 |
| DE | 19748109 | * 5/1999 |

OTHER PUBLICATIONS

CAPLUS 1995: 689079.*
CAPLUS 1996: 590418.*
CAPLUS 1996: 661099.*
English translation by computer for JP 09-118882, http://www4.ipdl.ncipi.go.jp/Tokujitu/PAJdetail.ipdl?N0000=60&N0120=01&N2001=2&N3001=H09-118882.*

* cited by examiner

*Primary Examiner*—Shean C. Wu
(74) *Attorney, Agent, or Firm*—Millen, White, Zelano, Branigan, P.C.

(57) ABSTRACT

Liquid-crystalline media comprising at least one compound of the formula I

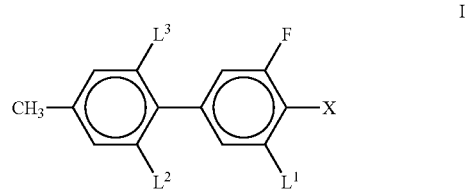

in which
X, $L^1$, $L^2$ and $L_3$ are as defined herein, are useful for use in electro-optical displays.

46 Claims, No Drawings

LIQUID-CRYSTALLINE MEDIUM

The present invention relates to a liquid-crystalline medium, to the use thereof for electro-optical purposes, and to displays containing this medium.

Liquid-crystals are used principally as dielectrics in display devices, since the optical properties of such substances can be modified by an applied voltage. Electro-optical devices based on liquid crystals are extremely well known to the person skilled in the art and can be based on various effects. Examples of such devices are cells having dynamic scattering, DAP (deformation of aligned phases) cells, guest/host cells, TN cells having a twisted nematic structure, STN (supertwisted nematic) cells, SBE (super-birefringence effect) cells and OMI (optical mode interference) cells. The commonest display devices are based on the Schadt-Helfrich effect and have a twisted nematic structure.

The liquid-crystal materials must have good chemical and thermal stability and good stability to electric fields and electromagnetic radiation. Furthermore, the liquid-crystal materials should have low viscosity and produce short addressing times, low threshold voltages and high contrast in the cells.

They should furthermore have a suitable mesophase, for example a nematic or cholesteric mesophase for the above-mentioned cells, at the usual operating temperatures, i.e., in the broadest possible range above and below room temperature. Since liquid crystals are generally used as mixtures of a plurality of components, it is important that the components are readily miscible with one another. Further properties, such as the electrical conductivity, the dielectric anisotropy and the optical anisotropy, have to satisfy various requirements depending on the cell type and area of application. For example, materials for cells having a twisted nematic structure should have positive dielectric anisotropy and low electrical conductivity.

For example, for matrix liquid-crystal displays with integrated non-linear elements for switching individual pixels (MLC displays), media having large positive dielectric anisotropy, broad nematic phases, relatively low birefringence, very high specific resistance, good UV and temperature stability and low vapour pressure are desired.

Matrix liquid-crystal displays of this type are known. Non-linear elements which can be used for individual switching of the individual pixels are, for example, active elements (i.e., transistors). The term "active matrix" is then used, where a distinction can be made between two types:
1. MOS (metal oxide semiconductor) or other diodes on a silicon wafer as substrate.
2. Thin-film transistors (TFTs) on a glass plate as substrate.

The use of single-crystal silicon as substrate material restricts the display size, since even modular assembly of various part-displays results in problems at the joints.

In the case of the more promising type 2, which is preferred, the electro-optical effect used is usually the TN effect. A distinction is made between two technologies: TFTs comprising compound semiconductors, such as, for example, CdSe, or TFTs based on polycrystalline or amorphous silicon. Intensive work is being carried out worldwide on the latter technology.

The TFT matrix is applied to the inside of one glass plate of the display, while the other glass plate carries the transparent counterelectrode on its inside. Compared with the size of the pixel electrode, the TFT is very small and has virtually no adverse effect on the image. This technology can also be extended to fully colour-capable displays, in which a mosaic of red, green and blue filters is arranged in such a way that a filter element is opposite each switchable pixel.

The TFT displays usually operate as TN cells with crossed polarisers in transmission and are illuminated from the back.

The term MLC displays here covers any matrix display with integrated non-linear elements, i.e., besides the active matrix, also displays with passive elements, such as varistors or diodes (MIM=metal-insulator-metal).

MLC displays of this type are particularly suitable for TV applications (for example, pocket TVs) or for high-information displays for computer applications (e.g., laptops) and in automobile or aircraft construction. Besides problems regarding the angle dependence of the contrast and the response times, difficulties also arise in MLC displays due to insufficiently high specific resistance of the liquid-crystal mixtures [TOGASHI, S., SEKIGUCHI, K., TANABE, H., YAMAMOTO, E., SORIMACHI, K., TAJIMA, E., WATANABE, H., SHIMIZU, H., Proc. Eurodisplay 84, September 1984: A 210–288 Matrix LCD Controlled by Double Stage Diode Rings, p. 141 ff, Paris; STROMER, M., Proc. Eurodisplay 84, September 1984: Design of Thin Film Transistors for Matrix Addressing of Television Liquid Crystal Displays, p. 145 ff, Paris]. With decreasing resistance, the contrast of an MLC display deteriorates, and the problem of after-image elimination may occur. Since the specific resistance of the liquid-crystal mixture generally drops over the life of an MLC display owing to interaction with the interior surfaces of the display, a high (initial) resistance is very important in order to obtain acceptable service lives. In particular in the case of low-volt mixtures, it was hitherto impossible to achieve very high specific resistance values. It is furthermore important that the specific resistance exhibits the smallest possible increase with increasing temperature and after heating and/or UV exposure. The low-temperature properties of the mixtures from the prior art are also particularly disadvantageous. It is demanded that no crystallisation and/or smectic phases occur, even at low temperatures, and the temperature dependence of the viscosity is as low as possible. The MLC displays from the prior art thus do not meet today's requirements.

In addition to liquid-crystal displays which use backlighting, i.e., are operated transmissively and if desired transflectively, reflective liquid-crystal displays are also particularly interesting. These reflective liquid-crystal displays use the ambient light for information display. They thus consume significantly less energy than back-lit liquid-crystal displays having a corresponding size and resolution. Since the TN effect is characterized by very good contrast, reflective displays of this type can even be read well in bright ambient conditions. This is already known of simple reflective TN displays, as used, for example, in watches and pocket calculators. However, the principle can also be applied to high-quality, higher-resolution active matrix-addressed displays, such as, for example, TFT displays. Here, as already in the transmissive TFT-TN displays which are generally conventional, the use of liquid crystals of low birefringence (Δn) is necessary in order to achieve low optical retardation (d·Δn). This low optical retardation results in usually acceptable low viewing-angle dependence of the contrast (cf. DE 30 22 818). In reflective displays, the use of liquid crystals of low birefringence is even more important than in transmissive displays since the effective layer thickness through which the light passes is approximately twice as large in reflective displays as in transmissive displays having the same layer thickness.

There thus continues to be a great demand for MLC displays having very high specific resistance at the same time as a large working-temperature range, short response times even at low temperatures and low threshold voltage which do not have these disadvantages, or only do so to a reduced extent.

In TN (Schadt-Helfrich) cells, media are desired which facilitate the following advantages in the cells:
extended nematic phase range (in particular down to low temperatures)
the ability to switch at extremely low temperatures (outdoor use, automobile, avionics)
increased resistance to UV radiation (longer service life)
low optical birefringence for small layer thicknesses
low threshold voltage.

The media available from the prior art do not allow these advantages to be achieved while simultaneously retaining the other parameters.

In the case of supertwisted (STN) cells, media are desired which enable greater multiplexability and/or lower threshold voltages and/or broader nematic phase ranges (in particular at low temperatures). To this end, a further widening of the available parameter latitude (clearing point, smectic-nematic transition or melting point, viscosity, dielectric parameters, elastic parameters) is urgently desired.

An object of the invention is to provide media, in particular for MLC, TN or STN displays of this type, which do not have the above-mentioned disadvantages or only do so to a reduced extent, and preferably simultaneously have very high specific resistances and low threshold voltages. This object requires liquid-crystalline compounds which have a high clearing point and low rotational viscosity.

Upon further study of the specification and appended claims, further objects and advantages of this invention will become apparent to those skilled in the art.

It has now been found that these objects can be achieved if use is made of a liquid-crystalline compound which has a terminal polar radical and a terminal $CH_3$ group. The compounds of the formula I reduce the elastic constants, in particular $K_1$, in a positive manner and result in mixtures having particularly low threshold voltages.

The invention thus relates to a liquid-crystalline medium based on a mixture of polar compounds of positive or negative dielectric anisotropy, comprising one or more compounds of the formula I in a temperature range which is favourably located for electro-optical use. In particular, the biphenyls according to the invention are distinguished by their high dielectric anisotropies and their low rotational viscosity values. They are stable chemically, thermally and with respect to light.

The invention also relates to compounds of the formula I.

In the compounds of the formula I, X is preferably selected from F, Cl, CN, NCS, $CF_3$, $SF_5$, $CF_2H$, $CF_2CF_3$, $CF_2CF_2CF_3$, $CH_2CH_2CF_3$, $CF_2CH_2CF_3$, $OCF_3$, $OCF_2H$, $OCFHCF_3$, $OCFHCFH_2$, $OCH_2C_3F_7$, $OCH_2CF_2CHFCF_3$, $O(CH_2)_3CF_3$, $OCFHCF_2H$, $OCF_2CH_3$, $OCF_2CFH_2$, $OCF_2CF_2H$, $OCF_2CF_2CF_2H$, $OCF_2CF_2CFH_2$, $OCFHCF_2CF_3$, $OCFHCF_2CF_2H$, $OCFHCFHCF_3$, $OCH_2CF_2CF_3$, $OCF_2CF_2CF_3$, $OCF_2CFHCFH_2$, $OCF_2CH_2CF_2H$, $OCFHCF_2CFH_2$, $OCFHCFHCF_2H$, $OCFHCH_2CF_3$, $OCH_2CFHCF_3$, $OCH_2CF_2CF_2H$, $OCF_2CFHCH_3$, $OCF_2CH_2CFH_2$, $OCFHCF_2CH_3$, $OCFHCFHCFH_2$, $OCFHCH_2CF_3$, $OCH_2CF_2CFH_2$, $OCH_2CFHCF_2H$, $OCF_2CH_2CH_3$, $OCFHCFHCH_3$, $OCFHCH_2CFH_2$, $OCH_2CF_2CH_3$, $OCH_2CFHCFH_2$, $OCH_2CH_2CF_2H$, $OCHCH_2CH_3$, $OCH_2CFHCH_3$, $OCH_2CH_2CF_2H$, $OCClFCF_3$, $OCClFCClF_2$, $OCClFCFH_2$, $OCFHCCl_2F$, $OCClFCF_2H$, $OCClFCClF_2$, $OCF_2CClH_2$, $OCF_2CCl_2H$, $OCF_2CCl_2F$, $OCF_2CClFH$, $OCF_2CClF_2$, $OCF_2CF_2CClF_2$, $OCF_2CF_2CCl_2F$, $OCClFCF_2CF_3$, $OCClFCF_2CF_2H$, $OCClFCF_2CClF_2$, $OCClFCFHCF_3$, $OCClFCClFCF_3$, $OCCl_2CF_2CF_3$, $OCClHCF_2CF_3$, $OCClFCF_2CF_3$, $OCClFCClFCF_3$, $OCF_2CClFCFH_2$, $OCF_2CF_2CCl_2F$, $OCF_2CCl_2CF_2H$, $OCF_2CH_2CClF_2$, $OCClFCF_2CFH_2$, $OCFHCF_2CCl_2F$, $OCClFCFHCF_2H$, $OCClFCClFCF_2H$, $OCFHCFHCClF_2$, $OCClFCH_2CF_3$, $OCFHCCl_2CF_3$, $OCCl_2CFHCF_3$, $OCH_2CClFCF_3$, $OCCl_2CF_2CF_2H$, $OCH_2CF_2CClF_2$, $OCF_2CClFCH_3$, $OCF_2CFHCCl_2H$, $OCF_2CCl_2CFH_2$, $OCF_2CH_2CCl_2F$, $OCClFCF_2CH_3$, $OCFHCF_2CCl_2H$, $OCClFCClFCFH_2$, $OCFHCFHCCl_2F$, $OCClFCH_2CF_3$, $OCFHCCl_2CF_3$, $OCCl_2CF_2CFH_2$, $OCH_2CF_2CCl_2F$, $OCCl_2CFHCF_2H$, $OCClHCClFCF_2H$, $OCF_2CClHCClH_2$, $OCF_2CH_2CCl_2H$, $OCClFCFHCH_3$, $OCF_2CClFCCl_2H$, $OCClFCH_2CFH_2$, $OCFHCCl_2CFH_2$, $OCCl_2CF_2CH_3$, $OCH_2CF_2CClH_2$, $OCCl_2CFHCFH_2$, $OCH_2CClFCFCl_2$, $OCH_2CH_2CF_2H$, $OCClHCClHCFH_2$, $OCH_2CCl_2CF_2H$, $OCClFCH_2CH_3$, $OCFHCH_2CCl_2H$, $OCClHCFHCClH_2$, $OCH_2CFHCCl_2H$, $OCCl_2CH_2CF_2H$, $OCH_2CCl_2CF_2H$, $CH=CF_2$, $CF=CF_2$, $OCH=CF_2$, $OCF=CF_2$, $CH=CHF$, $OCH=CHF$,

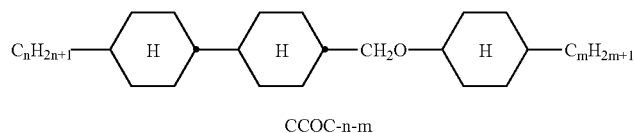

CCOC-n-m in which

X is F, Cl, CN, $SF_5$, NCS, or a halogenated alkyl radical having up to 8 carbon atoms, in which one or more $CH_2$ groups may, in each case independently, be replaced by —O— or —CH=CH— in such a way that O atoms are not linked directly to one another, and $L^1$, $L^2$ and $L^3$ are each, independently of one another, H or F.

In the pure state, the compounds of the formula I are colourless and generally form liquid-crystalline mesophases $CF=CHF$, and $OCF=CHF$, in particular F, Cl, CN, NCS, $CF_3$, $SF_5$, $CF_2H$, $CF_2CF_3$, $CF_2CF_2CF_3$, $CH_2CH_2CF_3$, $CF_2CH_2CF_3$, $OCF_3$, $OCF_2H$, $OCFHCF_3$, $OCFHCFH_2$, $OCFHCF_2H$, $OCF_2CH_3$, $OCF_2CFH_2$, $OCF_2CF_2H$, $OCF_2CF_2CF_2H$, $OCF_2CF_2CFH_2$, $OCFHCF_2CF_3$, $OCFHCF_2CF_2H$, $OCH_2C_3F_7$, $OCF_2CF_2CF_3$, $OCF_2CHFCF_3$ and $OCClFCF_2CF_3$.

Preferred smaller groups of compounds of the formula I are those of the sub-formulae I1 to I5:

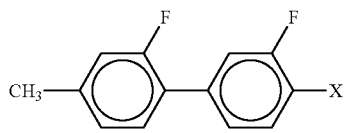
I1
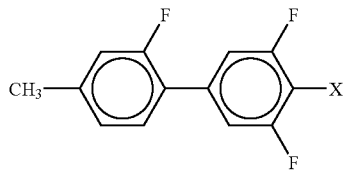
I2
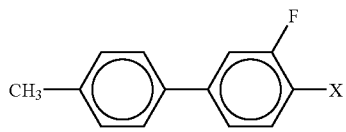
I3
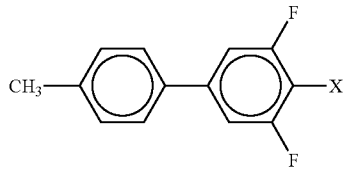
I4
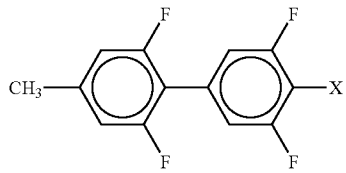
I5
in which
X is as defined in above. X in the sub-formulae I1 to I5 is preferably F or OCF$_3$. Particular preference is given to compounds of the formula I2 in which X is F or OCF$_3$.
Particularly preferred media comprise one or more compounds selected from the group consisting of the compounds of the formulae
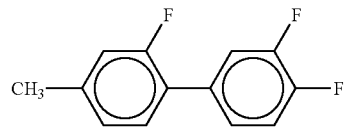
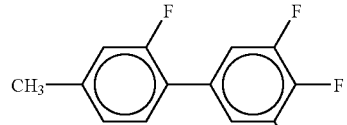
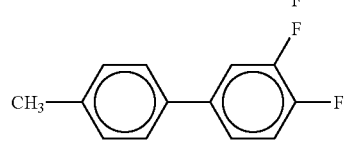
-continued
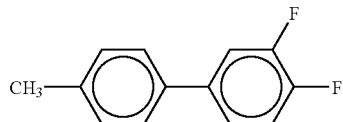
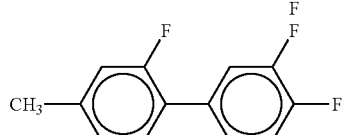
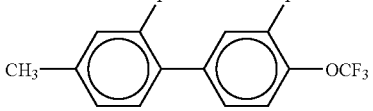
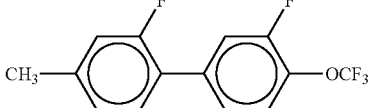
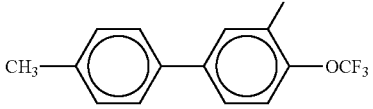
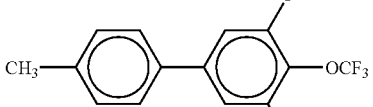
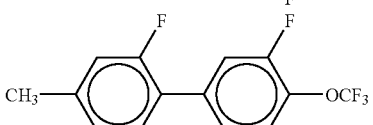
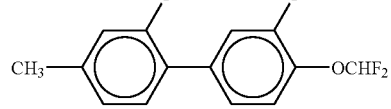
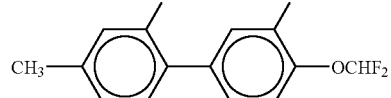
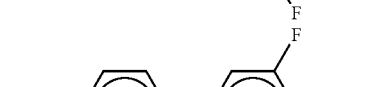

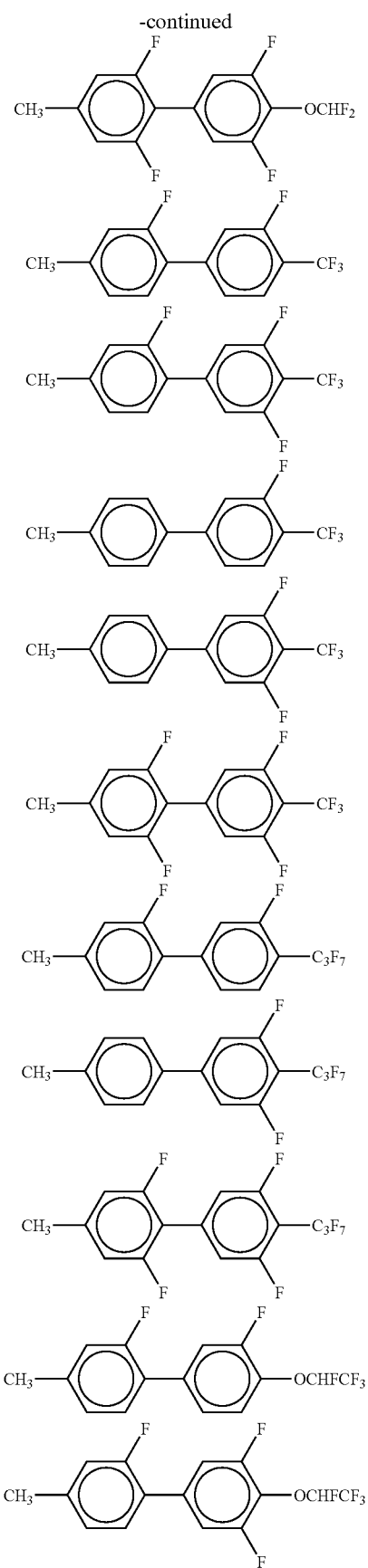
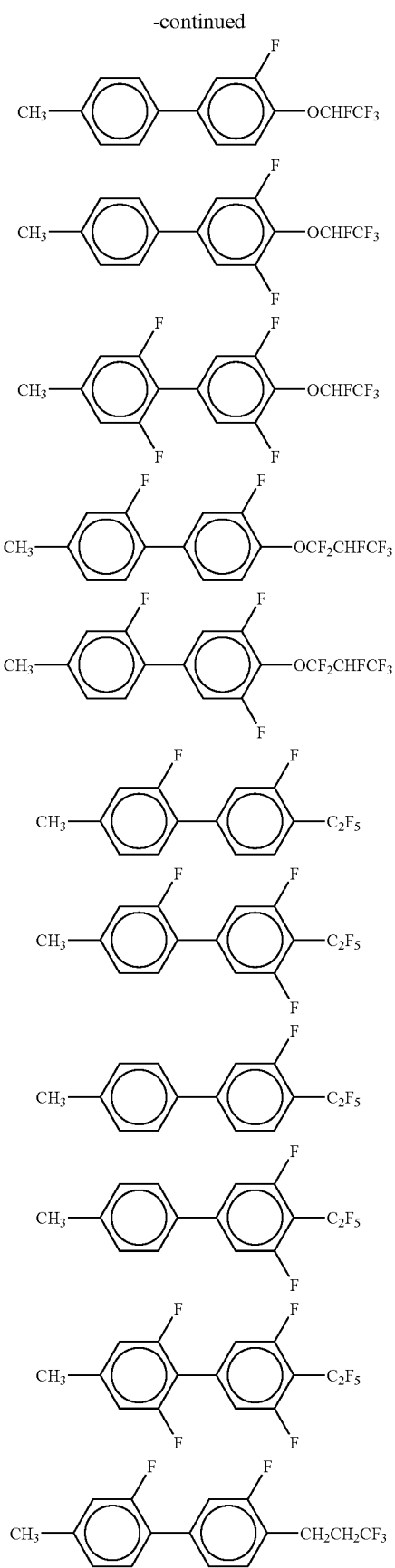

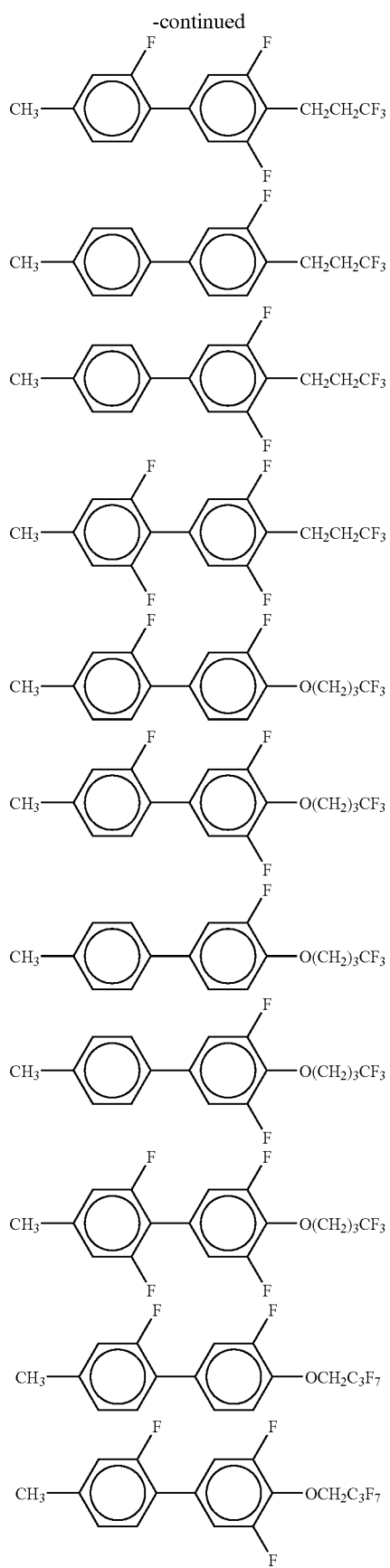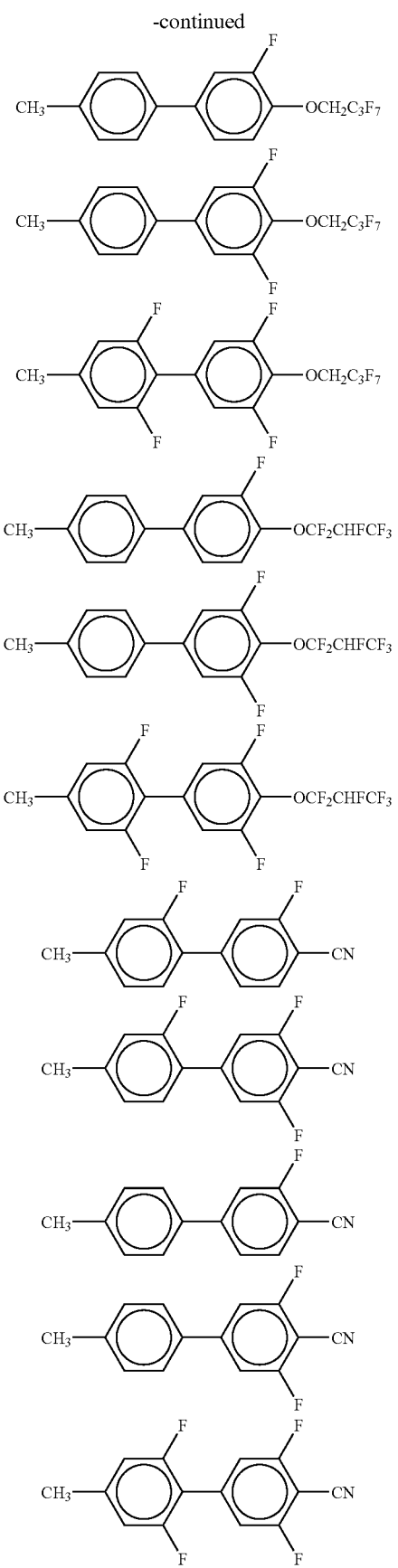

-continued

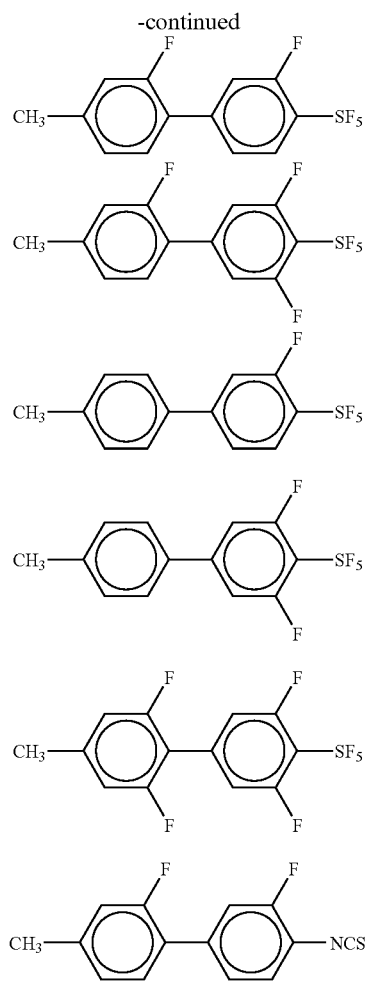

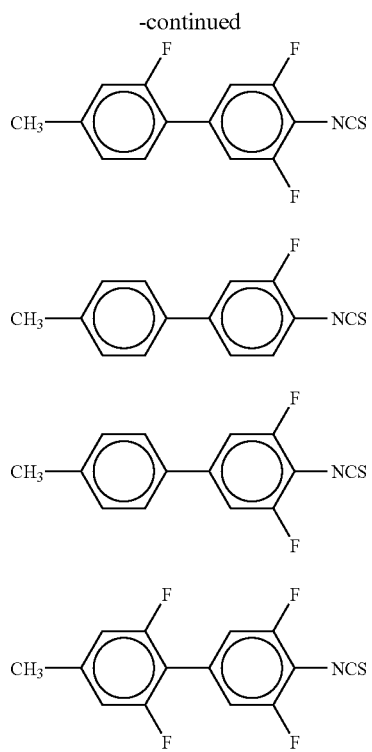

The compounds of the formula I are prepared by methods known per se, as described in the literature (for example in the standard works, such as Houben-Weyl, Methoden der Organischen Chemie [Methods of Organic Chemistry], Georg-Thieme-Verlag, Stuttgart), to be precise under reaction conditions which are known and suitable for the said reactions. Use can also be made here of variants which are known per se, but are not mentioned here in greater detail.

Scheme 1

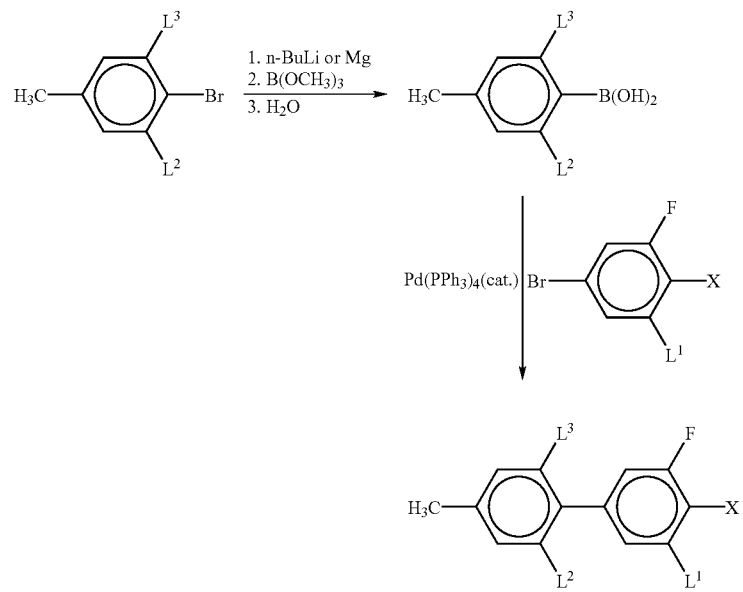

Scheme 2
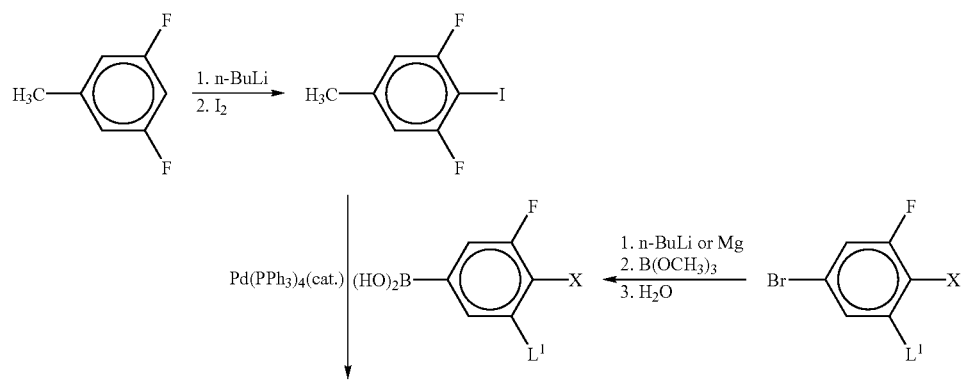
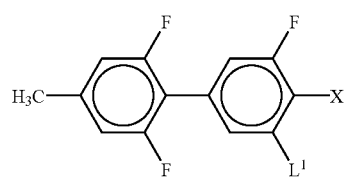
Scheme 3
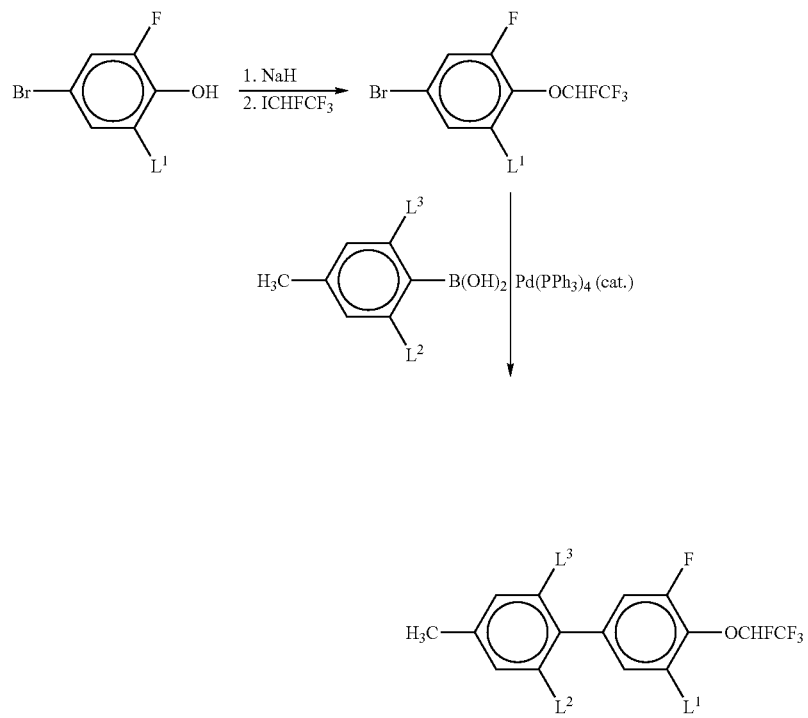

Scheme 4

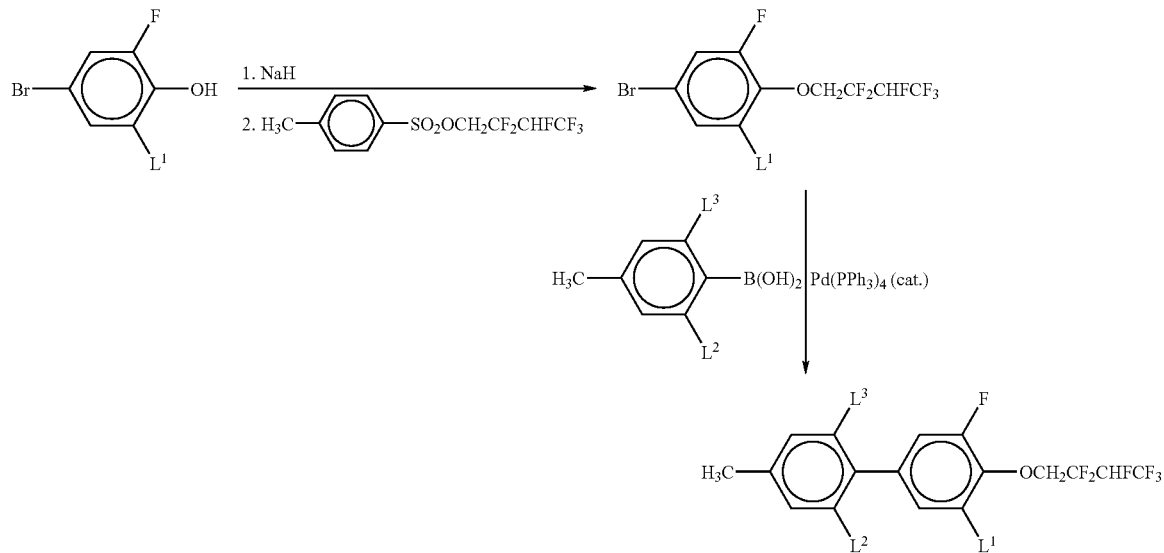

Scheme 5

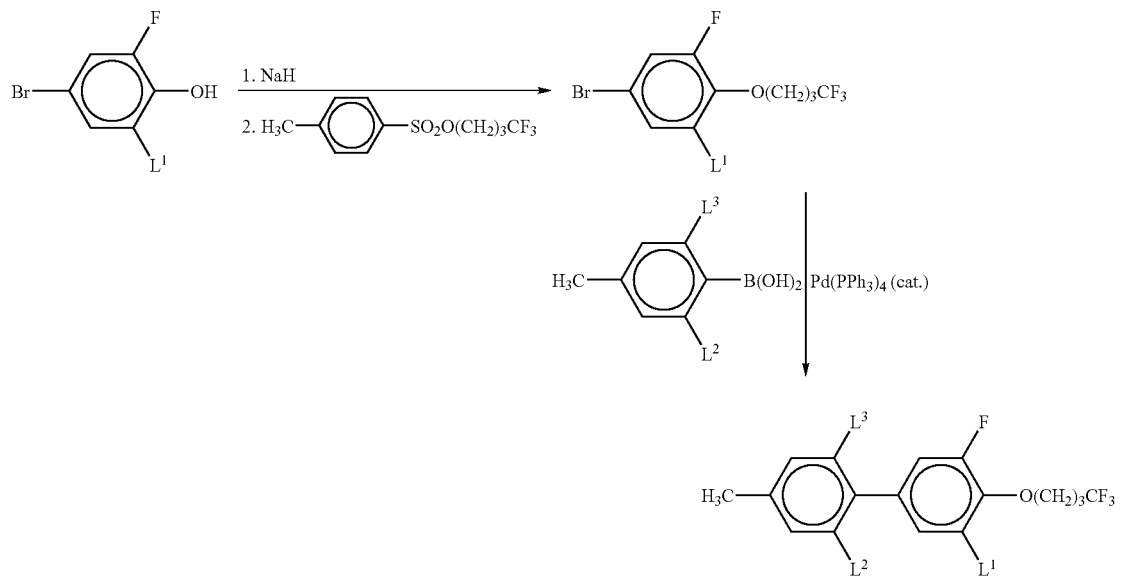

The invention also relates to electro-optical displays (in particular STN or MLC displays having two plane-parallel outer plates, which, together with a frame, form a cell, integrated non-linear elements for switching individual pixels on the outer plates, and a nematic liquid-crystal mixture of positive dielectric anisotropy and high specific resistance which is located in the cell) which contain media of this type, and to the use of these media for electro-optical purposes.

The liquid-crystal mixtures according to the invention enable a significant widening of the available parameter latitude.

The achievable combinations of clearing point, optical anisotropy, viscosity at low temperature, thermal and UV stability, and dielectric anisotropy are far superior to previous materials from the prior art.

The requirement for a high clearing point, a nematic phase at low temperature and a high Δ∈ has hitherto only been achieved to an inadequate extent. Although liquid-crystal mixtures such as, for example, MLC-6476 and MLC-6625 (Merck KGaA, Darmstadt, Germany) have comparable clearing points and low-temperature stabilities, they have, however, relatively high Δn values and also higher threshold voltages of about ≧1.7 V.X.

Other mixture systems have comparable viscosities and Δ∈ values, but only have clearing points in the region of 60° C.

The liquid-crystal mixtures according to the invention, while retaining the nematic phase down to −20° C. and preferably down to −30° C., particularly preferably down to −40° C., enable clearing points above 80° C., preferably above 90° C., particularly preferably above 100° C., simultaneously dielectric anisotropy values Δ∈ of ≧4, preferably ≧6, and a high value for the specific resistance to be achieved, enabling excellent STN and MLC displays to be obtained. In particular, the mixtures are characterised by low operating voltages. The TN thresholds are below 1.5 V, preferably below 1.3 V.

It goes without saying that, through a suitable choice of the components of the mixtures according to the invention, it is also possible for higher clearing points (for example, above 110° C.) to be achieved at a higher threshold voltage or lower clearing points to be achieved at lower threshold voltages with retention of the other advantageous properties. At viscosities correspondingly increased only slightly, it is likewise possible to obtain mixtures having greater Δ∈ and thus lower thresholds. The MLC displays according to the invention preferably operate at the first Gooch and Tarry transmission minimum [C. H. Gooch and H. A. Tarry, Electron. Lett. 10, 2–4, 1974; C. H. Gooch and H. A. Tarry, Appl. Phys., Vol. 8, 1575–1584, 1975], where, besides particularly favourable electro-optical properties, such as low angle dependence of the contrast (German Patent 30 22 818), a lower dielectric anisotropy is sufficient at the same threshold voltage as in an analogous display at the second minimum. This enables significantly higher specific resistances to be achieved using the mixtures according to the invention at the first minimum than in the case of mixtures comprising cyano compounds. Through a suitable choice of the individual components and their proportions by weight, the person skilled in the art is able to set the birefringence necessary for a pre-specified layer thickness of the MLC display using simple routine methods.

The flow viscosity $\nu_{20}$ at 20° C. is preferably <60 mm$^2$·s$^{-1}$, particularly preferably <50 mm$^2$·s$^1$. The nematic phase range is preferably at least 90°, in particular at least 100°. This range preferably extends at least from −30° to +80°.

Measurements of the capacity holding ratio (HR) [S. Matsumoto et al., Liquid Crystals 5, 1320 (1989); K. Niwa et al., Proc. SID Conference, San Francisco, June 1984, p. 304 (1984); G. Weber et al., Liquid Crystals 5, 1381 (1989)] have shown that mixtures according to the invention comprising compounds of the formula I exhibit a significantly smaller decrease in the HR with increasing temperature than, for example, analogous mixtures comprising cyanophenylcyclohexanes of the formula

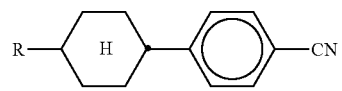

or esters of the formula

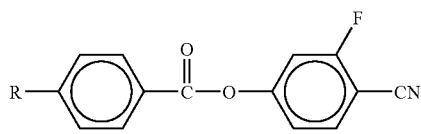

instead of the compounds of the formula I.

The UV stability of the mixtures according to the invention is also considerably better, i.e., they exhibit a significantly smaller decrease in the HR on exposure to UV.

The media according to the invention are preferably based on one or more (preferably one, two, three or more) compounds of the formula I, i.e., the proportion of these compounds is 5–95%, preferably 5–50% and particularly preferably in the range 15–40%.

The individual compounds of the formulae I to X and their sub-formulae which can be used in the media according to the invention are either known or they can be prepared analogously to the known compounds.

Preferred embodiments are indicated below:

Medium additionally comprises one or more compounds selected from the group consisting of the general formulae II to X:

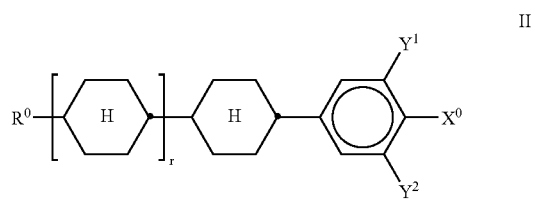

II

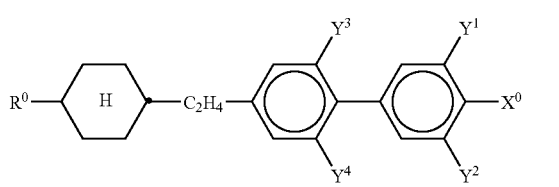

III

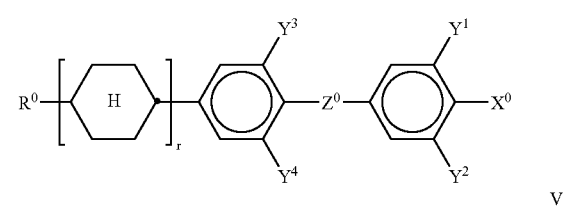

IV

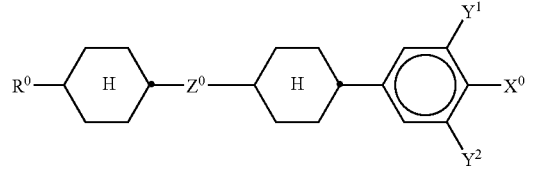

V

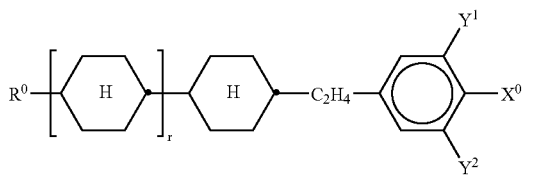

VI

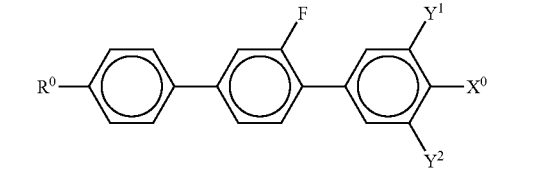

VII

-continued

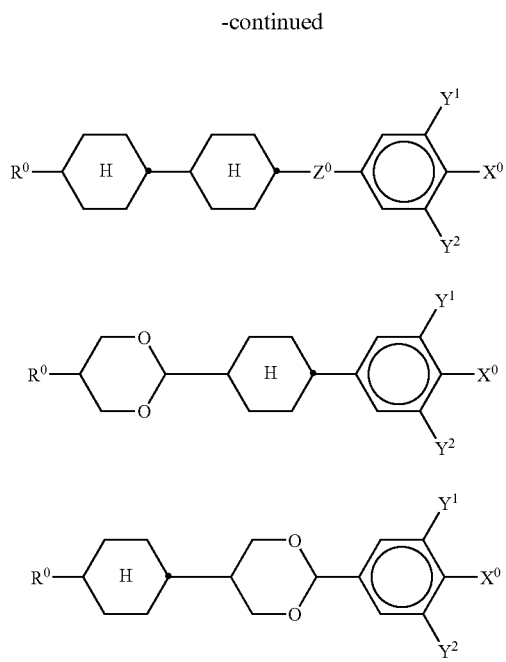

VIII

IX

X in which the individual radicals have the following meanings:

$R^0$ is n-alkyl, oxaalkyl, fluoroalkyl, alkenyloxy or alkenyl, each having from 2 to 12 carbon atoms, $X^0$ is F, Cl, halogenated alkyl, halogenated alkenyl, halogenated alkenyloxy or halogenated alkoxy each having up to 8 carbon atoms, $Z^0$ is —CH=CH—, —$C_2H_4$—, —$CH_2O$—, —$OCH_2$—, —$(CH_2)_4$—, —$C_2F_4$—, —CF=CF—, —$CF_2O$—, —$OCF_2$— or —COO—, $Y^1$, $Y^2$, $Y^3$ and $Y^4$ are each, independently of one another, H or F, and r is 0 or 1.

The compound of the formula IV is preferably

-continued

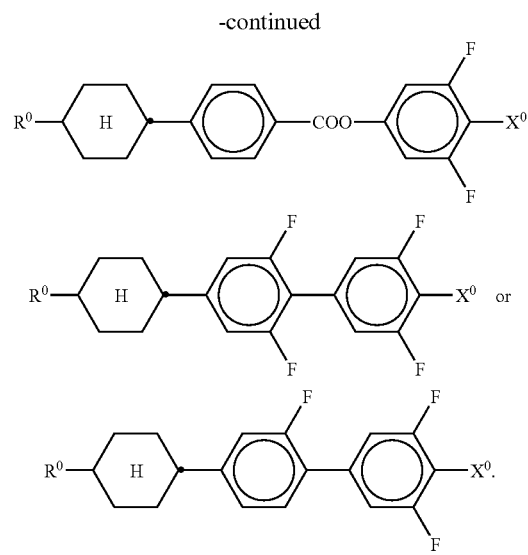

In particular, the medium additionally comprises one or more compounds of the formulae

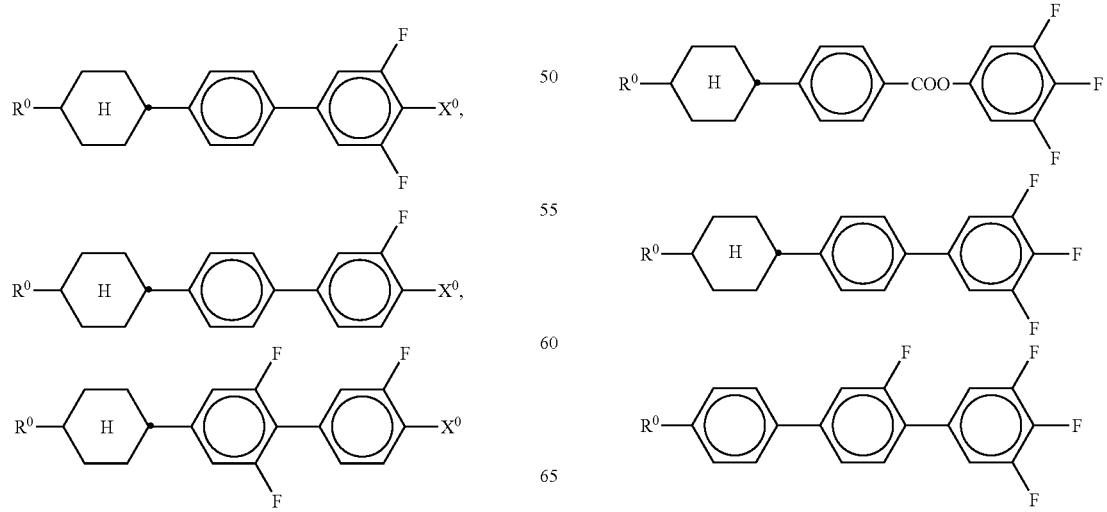

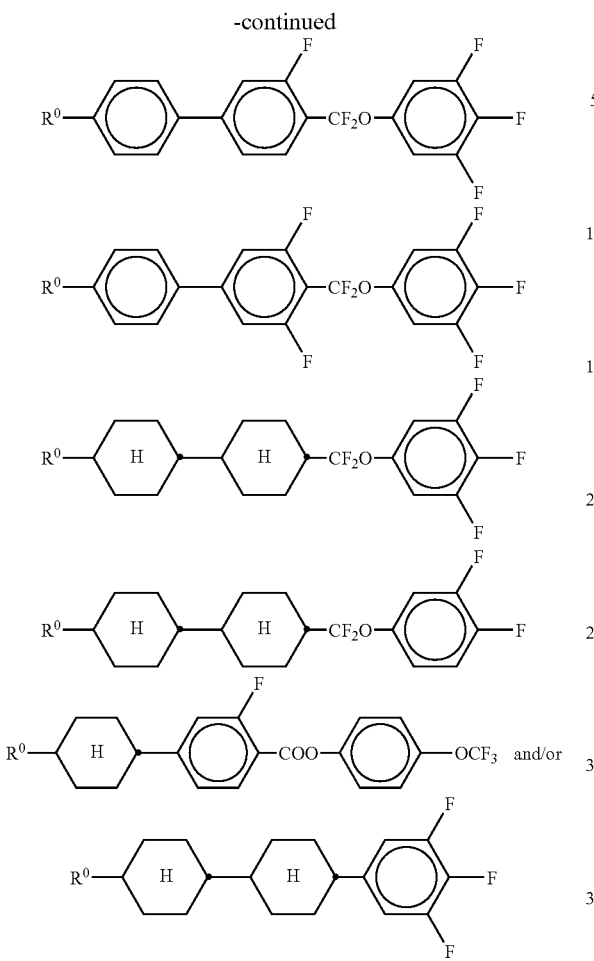
in which $R^0$ and $Y^2$ are as defined above.
The medium preferably comprises one, two or three, furthermore four homologues of the compounds selected from the group consisting of H1 to H18 (n=2–12):
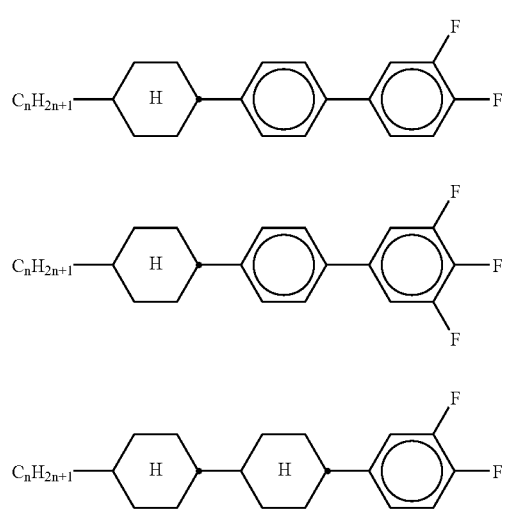

-continued

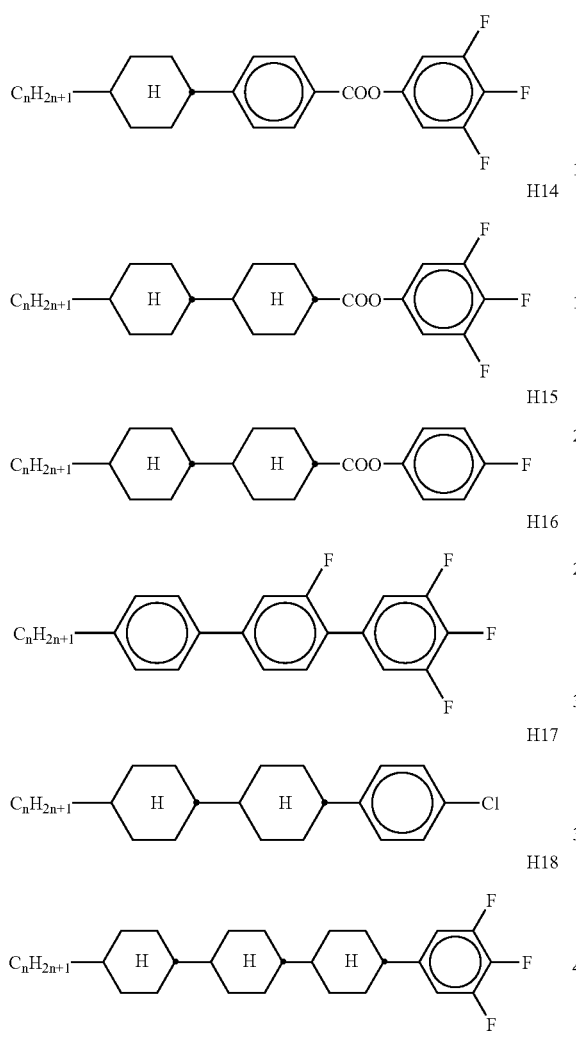

The medium additionally comprises one or more dioxanes of the formula DI and/or DII,

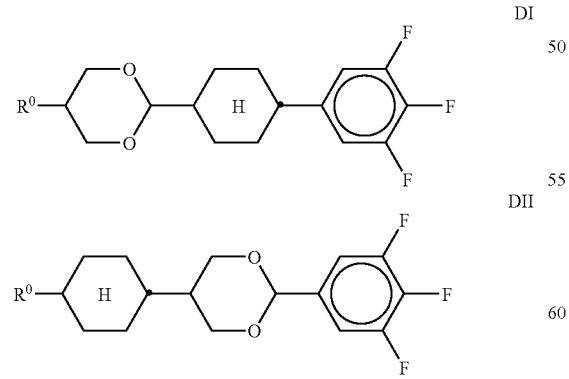

in which $R^0$ is as defined above. $R^0$ in the compounds of the formula DI and/or DII is preferably straight-chain alkyl or alkenyl having up to 8 carbon atoms.

The medium additionally comprises one or more compounds selected from the group consisting of the general formulae XI to XVI:

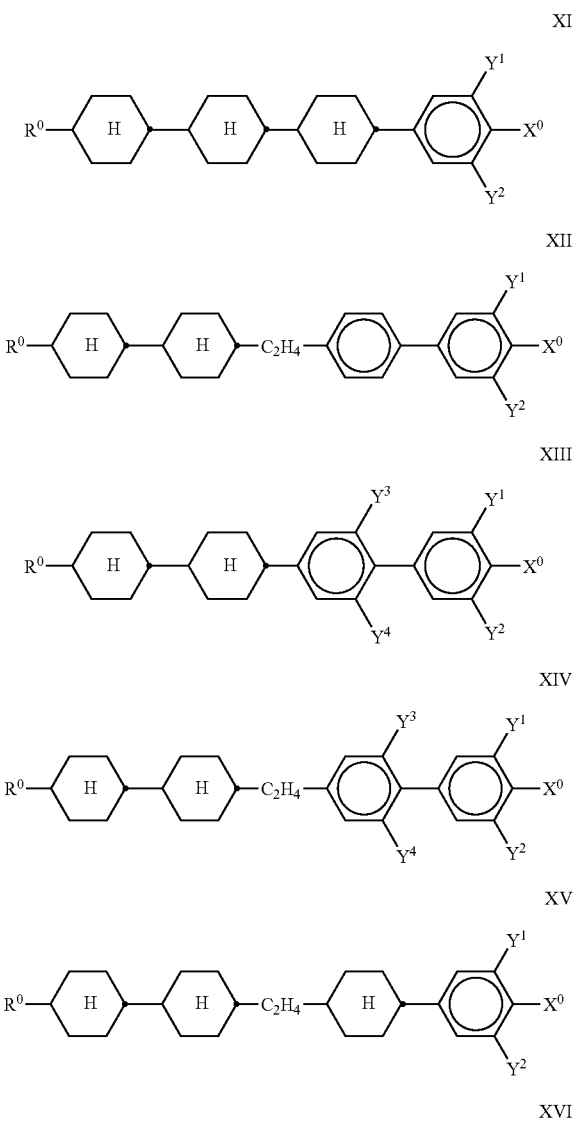

in which $R^0$, $X^0$, $Y^1$, $Y^2$, $Y^3$ and $Y^4$ are each, independently of one another, as defined above. $X^0$ is preferably F, Cl, $CF_3$, $OCF_3$ or $OCHF_2$. $R^0$ is preferably alkyl, oxaalkyl, fluoroalkyl, alkenyl or alkenyloxy.

The proportion of compounds of the formulae I to X together in the mixture as a whole is at least 50% by weight.

The proportion of compounds of the formula I in the mixture as a whole is from 5 to 50% by weight.

The proportion of compounds of the formulae II to X in the mixture as a whole is from 30 to 70% by weight.

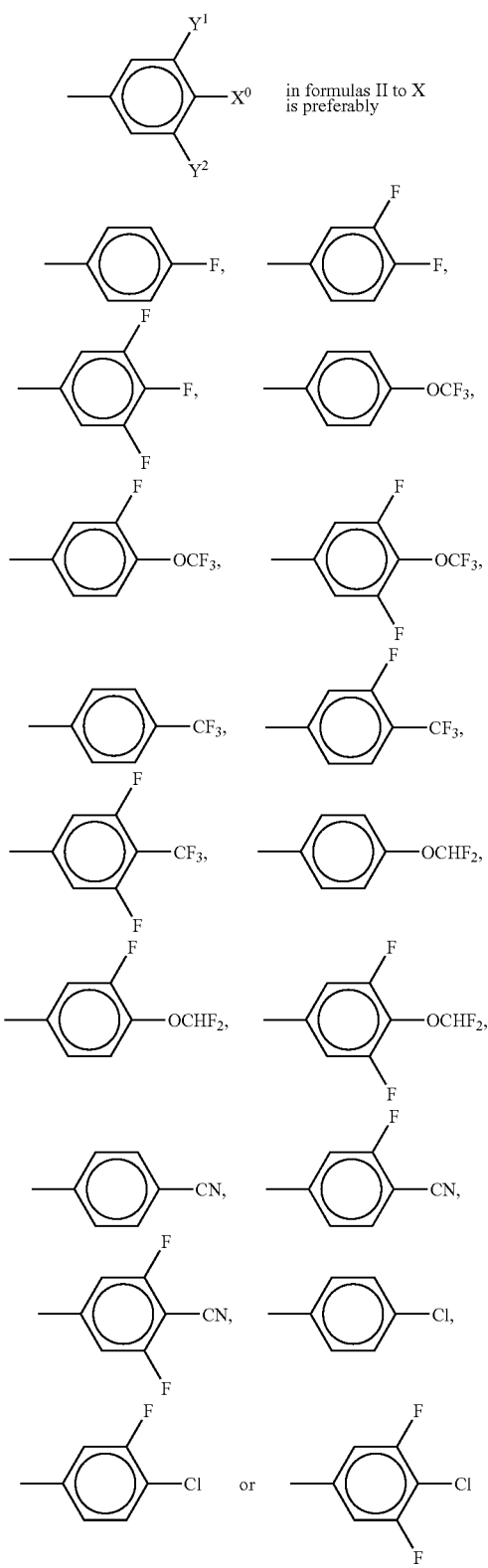

in formulas II to X is preferably

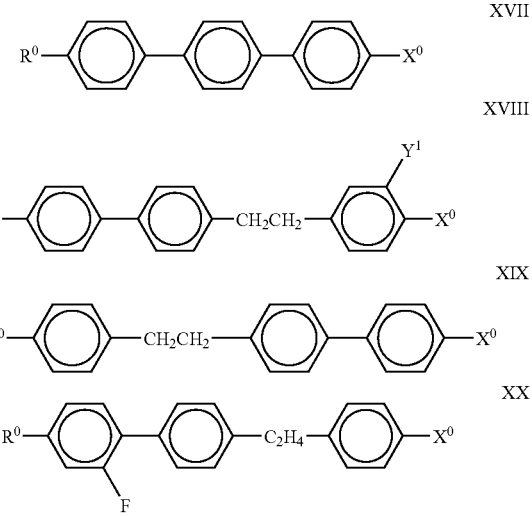

The medium comprises compounds of the formulae II, III, IV, V, VI, VII, VIII, IX and/or X.

$R^0$ is straight-chain alkyl or alkenyl having from 2 to 8 carbon atoms.

The medium consists essentially of compounds of the formulae I to XVI.

The medium comprises further compounds, preferably selected from the following group consisting of the general formulae XVII to XX:

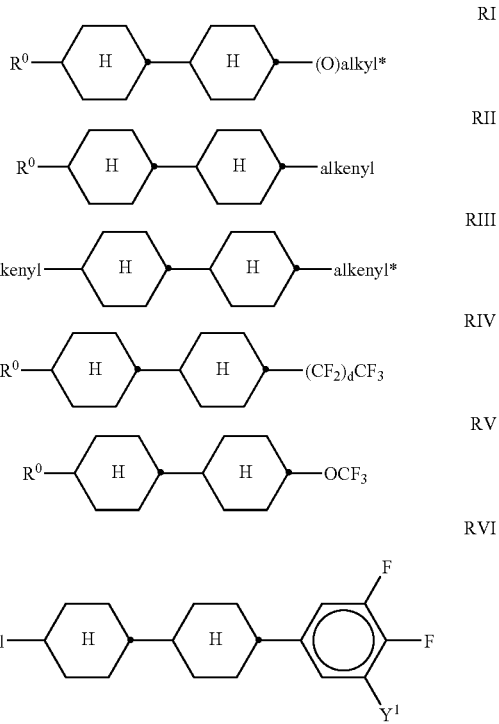

in which $R^0$, $Y^1$ and $X^0$ are as defined above, and the 1,4-phenylene rings may be substituted by CN, chlorine or fluorine. The 1,4-phenylene rings are preferably monosubstituted or polysubstituted by fluorine atoms.

The medium comprises further compounds, preferably selected from the following group consisting of the formulae RI to RXV:

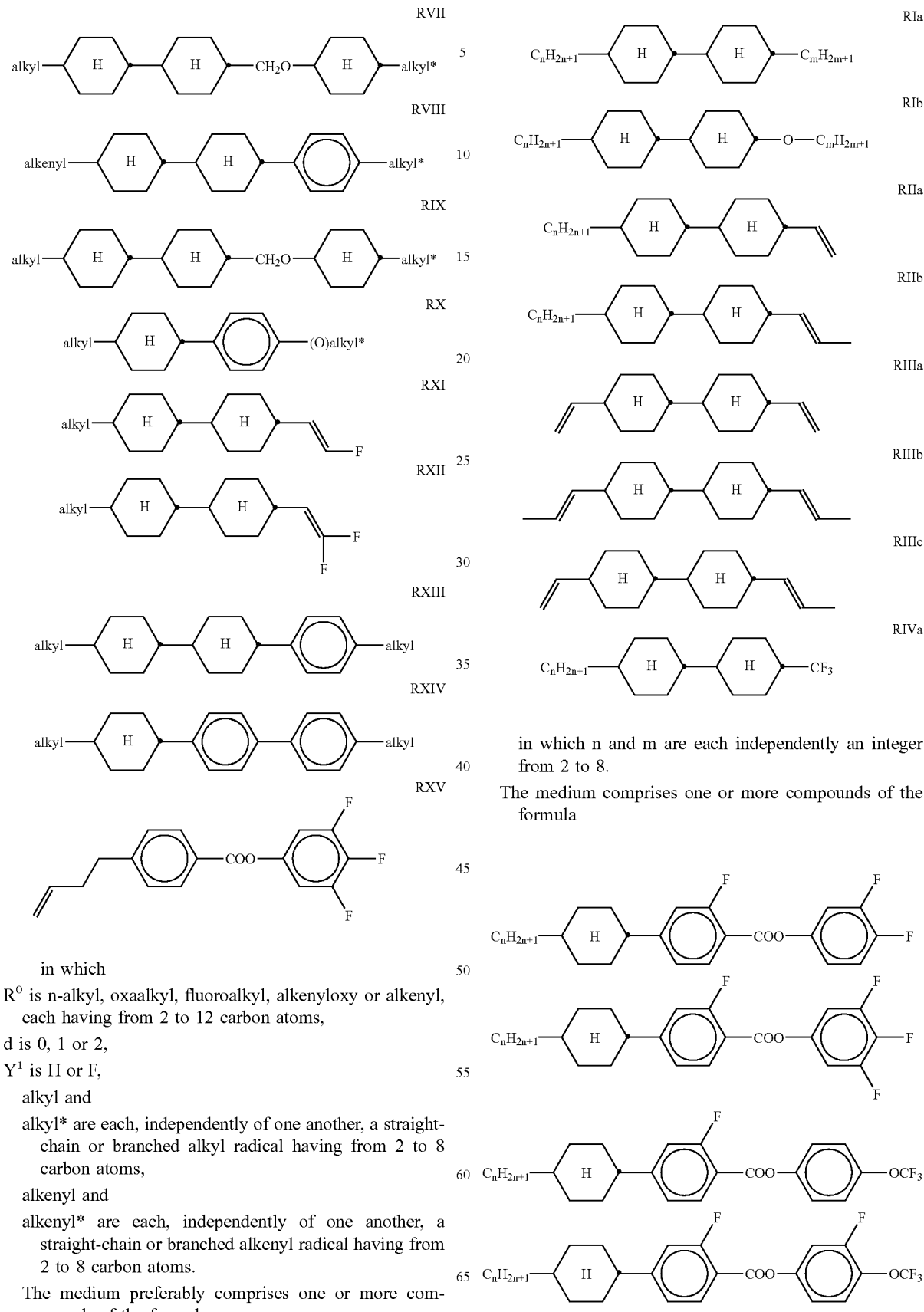

in which n and m are each independently an integer from 2 to 8.

The medium comprises one or more compounds of the formula in which
$R^0$ is n-alkyl, oxaalkyl, fluoroalkyl, alkenyloxy or alkenyl, each having from 2 to 12 carbon atoms,
d is 0, 1 or 2,
$Y^1$ is H or F,
  alkyl and
  alkyl* are each, independently of one another, a straight-chain or branched alkyl radical having from 2 to 8 carbon atoms,
  alkenyl and
  alkenyl* are each, independently of one another, a straight-chain or branched alkenyl radical having from 2 to 8 carbon atoms.

The medium preferably comprises one or more compounds of the formulae

-continued

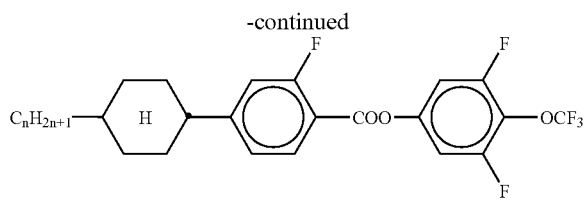

The medium preferably comprises one or more compounds having a $CF_2O$ bridge, in particular compounds of the formula

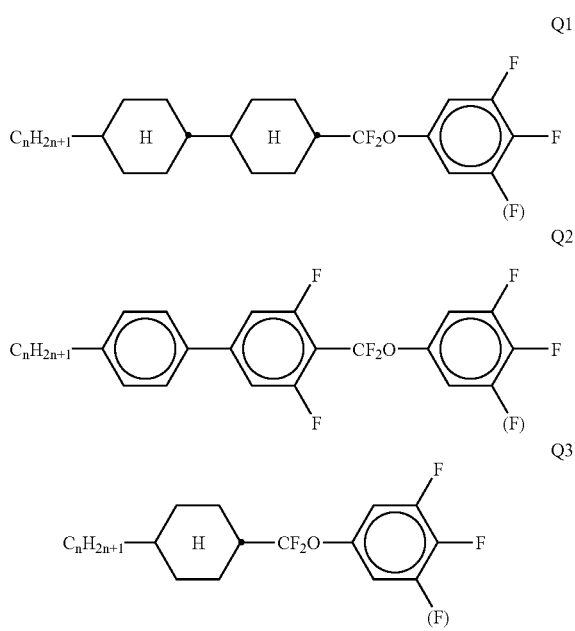

The I: (II+III+IV+V+VI+VII+VIII+IX+X) weight ratio is preferably from 1:10 to 10:1.

It has been found that even a relatively small proportion of compounds of the formula I mixed with conventional liquid-crystal materials, but in particular with one or more compounds of the formulae II, III, IV, V, VI, VII, VIII, IX and/or X, results in a significant lowering of the threshold voltage and in low birefringence values, with broad nematic phases with low smectic-nematic transition temperatures being observed at the same time, improving the shelf life. The compounds of the formulae I to X are colourless, stable and readily miscible with one another and with other liquid-crystalline materials.

The term "alkyl" or "alkyl*" covers straight-chain and branched alkyl groups having from 2 to 8 carbon atoms, in particular the straight-chain groups ethyl, propyl, butyl, pentyl, hexyl and heptyl. Groups having 2–5 carbon atoms are generally preferred.

The term "alkenyl" or "alkenyl*" covers straight-chain and branched alkenyl groups having up to 8 carbon atoms, in particular the straight-chain groups. Preferred alkenyl groups are $C_2$–$C_7$-1E-alkenyl, $C_4$–$C_7$-3E-alkenyl, $C_5$–$C_7$-4-alkenyl, $C_6$–$C_7$-5-alkenyl and $C_7$-6-alkenyl, in particular $C_2$–$C_7$-1E-alkenyl, $C_4$–$C_7$-3E-alkenyl and $C_5$–$C_7$-4-alkenyl. Examples of particularly preferred alkenyl groups are vinyl, 1E-propenyl, 1E-butenyl, 1E-pentenyl, 1E-hexenyl, 1E-heptenyl, 3-butenyl, 3E-pentenyl, 3E-hexenyl, 3E-heptenyl, 4-pentenyl, 4Z-hexenyl, 4E-hexenyl, 4Z-heptenyl, 5-hexenyl, 6-heptenyl and the like. Groups having up to 5 carbon atoms are generally preferred.

The term "fluoroalkyl" preferably covers straight-chain groups having a terminal fluorine, i.e., fluoromethyl, 2-fluoroethyl, 3-fluoropropyl, 4-fluorobutyl, 5-fluoropentyl, 6-fluorohexyl and 7-fluoroheptyl. However, other positions of the fluorine are not excluded.

The term "oxaalkyl" preferably covers straight-chain radicals of the formula $C_nH_{2n+1}$—O—$(CH_2)_m$, in which n and m are each, independently of one another, from 1 to 6. n is preferably=1 and m is preferably from 1 to 6.

Through a suitable choice of the meanings of $R^0$ and $X^0$, the addressing times, the threshold voltage, the steepness of the transmission characteristic lines, etc., can be modified in the desired manner. For example, 1E-alkenyl radicals, 3E-alkenyl radicals, 2E-alkenyloxy radicals and the like generally result in shorter addressing times, improved nematic tendencies and a higher ratio of the elastic constants $k_{33}$ (bend) and $k_{11}$ (splay) compared with alkyl or alkoxy radicals. 4-alkenyl radicals, 3-alkenyl radicals and the like generally give lower threshold voltages and larger values of $k_{33}/k_{11}$ compared with alkyl and alkoxy radicals.

A —$CH_2CH_2$— group in $Z^0$ generally results in higher values of $k_{33}/k_{11}$ compared with a single covalent bond. Higher values of $k_{33}/k_{11}$ facilitate, for example, flatter transmission characteristic lines in TN cells with a 90° twist (in order to achieve grey shades) and steeper transmission characteristic lines in STN, SBE and OMI cells (greater multiplexability), and vice versa.

The optimum mixing ratio of the compounds of the formulae I and II+III+IV+V+VI+VII+VIII+IX+X depends substantially on the desired properties, on the choice of the components of the formulae I, II, III, IV, V, VI, VII, VIII, IX and/or X, and the choice of any other components that may be present. Suitable mixing ratios within the range given above can easily be determined from case to case.

The total amount of compounds of the formulae I to XVI in the mixtures according to the invention is not crucial. The mixtures can therefore comprise one or more further components for the purposes of optimising various properties. However, the observed effect on the addressing times and the threshold voltage is generally greater, the higher the total concentration of compounds of the formulae I to XVI.

In a particularly preferred embodiment, the media according to the invention comprise compounds of the formulae II to X (preferably II and/or III) in which $X^0$ is $OCF_3$, $OCHF_2$, F, $OCH=CF_2$, $OCF=CF_2$, $OCF_2CHFCF_3$ or $OCF_2$—$CF_2H$. A favourable synergistic effect with the compounds of the formula I results in particularly advantageous properties.

The mixtures according to the invention having low optical anisotropy ($\Delta n<0.07$) are particularly suitable for reflective displays. Low $V_{th}$ mixtures are particularly suitable for 2.5 V drivers and 3.3 V drivers and 4V or 5V drivers. Ester-free mixtures are preferred for the latter applications. The mixtures according to the invention are furthermore suitable for high $\Delta n$ IPS applications.

The construction of the MLC display according to the invention from polarisers, electrode base plates and surface-treated electrodes corresponds to the conventional construction for displays of this type. The term "conventional construction" is broadly drawn here and also covers all derivatives and modifications of the MLC display, in particular including matrix display elements based on poly-Si TFT or MIM.

A significant difference between the displays according to the invention and the conventional displays based on the twisted nematic cell consists, however, in the choice of the liquid-crystal parameters of the liquid-crystal layer.

The liquid-crystal mixtures which can be used in accordance with the invention are prepared in a manner conventional per se. In general, the desired amount of the components used in the lesser amount is dissolved in the components making up the principal constituent, advantageously at elevated temperature. It is also possible to mix solutions of the components in an organic solvent, for example in acetone, chloroform or methanol, and to remove the solvent again, for example by distillation, after thorough mixing.

The dielectrics may also comprise further additives known to the person skilled in the art and described in the literature. For example, 0–15% (e.g., 0–10%) of pleochroic dyes, chiral dopants or stabilizers (such as UV absorbers) can be added.

C denotes a crystalline phase, S a smectic phase, $S_C$ a smectic C phase, N a nematic phase and I the isotropic phase.

$V_{10}$ denotes the voltage for 10% transmission (viewing angle perpendicular to the plate surface). $t_{on}$ denotes the switch-on time and $t_{off}$ the switch-off time at an operating voltage corresponding to 2 times the value of $V_{10}$. $\Delta n$ denotes the optical anisotropy and $n_o$ the refractive index. $\Delta\varepsilon$ denotes the dielectric anisotropy ($\Delta\varepsilon=\varepsilon_\parallel-\varepsilon_\perp$, where $\varepsilon_\parallel$ denotes the dielectric constant parallel to the longitudinal molecular axes and $\varepsilon_\perp$ denotes the dielectric constant perpendicular thereto). The electro-optical data were measured in a TN cell at the 1 st minimum (i.e., at a d·Δn value of 0.5) at 20° C., unless expressly stated otherwise. The optical data were measured at 20° C., unless expressly stated otherwise.

In the foregoing and in the following examples, all temperatures are set forth uncorrected in degrees Celsius; and, unless otherwise indicated, all parts and percentages are by weight.

The entire disclosure of all applications, patents and publications, cited above and below, and of corresponding German Application No. 101 55 079.0, filed Nov. 9, 2001 is hereby incorporated by reference.

In the present application and in the examples below, the structures of the liquid-crystal compounds are indicated by means of acronyms, the transformation into chemical formulae taking place in accordance with Tables A and B below. All radicals $C_nH_{2n+1}$ and $C_mH_{2m+1}$ are straight-chain alkyl radicals having n and m carbon atoms respectively; n and m are in each case, independently of one another, 1, 2, 3, 4, 5, 6, 7, 8, 9, 10, 11, 12, 13, 14 or 15. The coding in Table B is self-evident. In Table A, only the acronym for the parent structure is indicated. In individual cases, the acronym for the parent structure is followed, separated by a dash, by a code for the substituents $R^1$, $R^2$, $L^1$ and $L^2$:

| Code for $R^1$, $R^2$, $L^1$, $L^2$ | $R^1$ | $R^2$ | $L^1$ | $L^2$ |
|---|---|---|---|---|
| nm | $C_nH_{2n+1}$ | $C_mH_{2m+1}$ | H | H |
| nOm | $C_nH_{2n+1}$ | $OC_mH_{2m+1}$ | H | H |
| nO.m | $OC_nH_{2n+1}$ | $C_mH_{2m+1}$ | H | H |
| n | $C_nH_{2n+1}$ | CN | H | H |
| nN.F | $C_nH_{2n+1}$ | CN | H | F |
| nF | $C_nH_{2n+1}$ | F | H | H |
| nOF | $OC_nH_{2n+1}$ | F | H | H |
| nCl | $C_nH_{2n+1}$ | Cl | H | H |

-continued

| Code for $R^1$, $R^2$, $L^1$, $L^2$ | $R^1$ | $R^2$ | $L^1$ | $L^2$ |
|---|---|---|---|---|
| nF.F | $C_nH_{2n+1}$ | F | H | F |
| nF.F.F | $C_nH_{2n+1}$ | F | F | F |
| nCF$_3$ | $C_nH_{2n+1}$ | CF$_3$ | H | H |
| nOCF$_3$ | $C_nH_{2n+1}$ | OCF$_3$ | H | H |
| nOCF$_2$ | $C_nH_{2n+1}$ | OCHF$_2$ | H | H |
| nS | $C_nH_{2n+1}$ | NCS | H | H |
| rVsN | $C_rH_{2r+1}$—CH=CH—$C_sH_{2s}$— | CN | H | H |
| rEsN | $C_rH_{2r+1}$—O—$C_2H_{2s}$— | CN | H | H |
| nAm | $C_nH_{2n+1}$ | COOC$_m$H$_{2m+1}$ | H | H |
| nOCCF$_2$.F.F | $C_nH_{2n+1}$ | OCH$_2$CF$_2$H | F | F |

Preferred mixture components are given in Tables A and B.

TABLE A

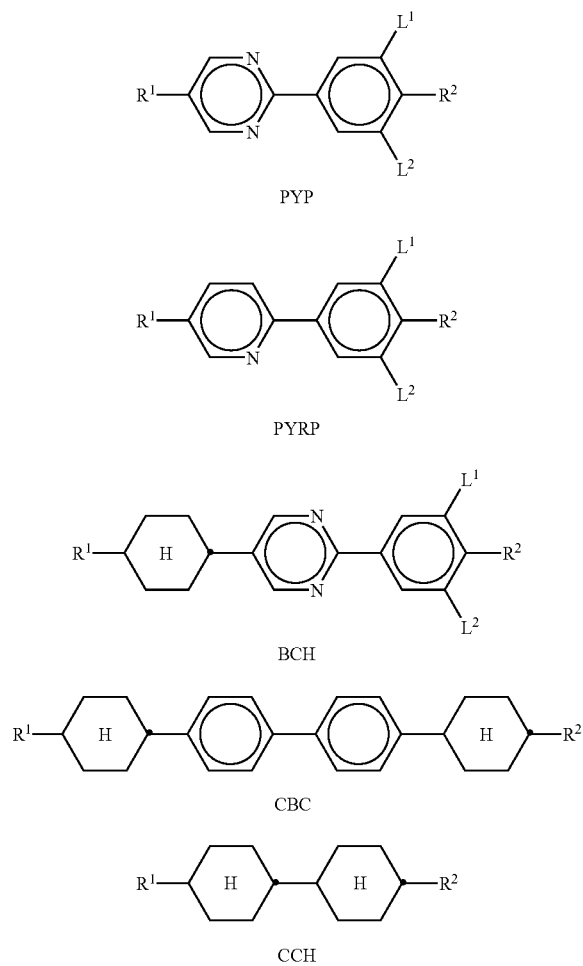

PYP

PYRP

BCH

CBC

CCH

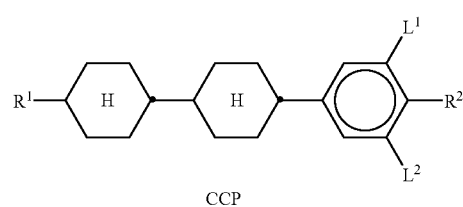

CCP

TABLE A-continued
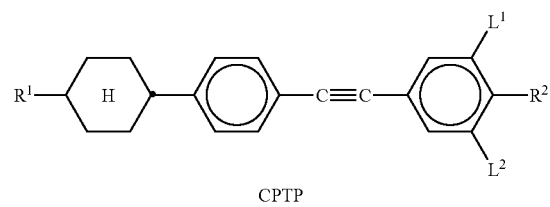
CPTP
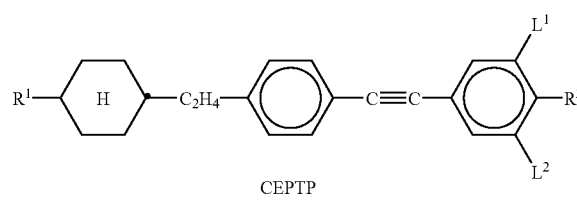
CEPTP
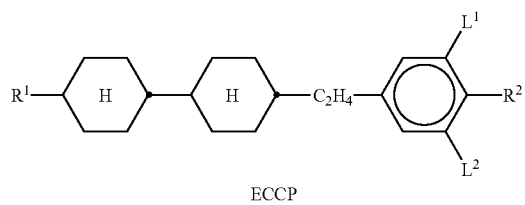
ECCP
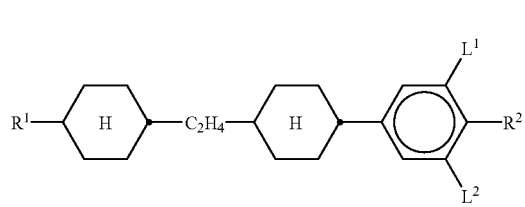
CECP
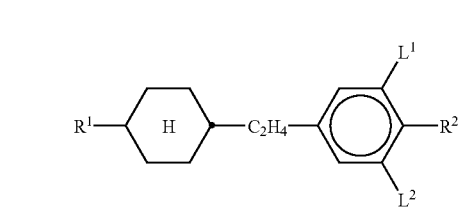
EPCH
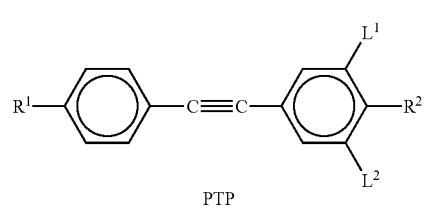
PCH
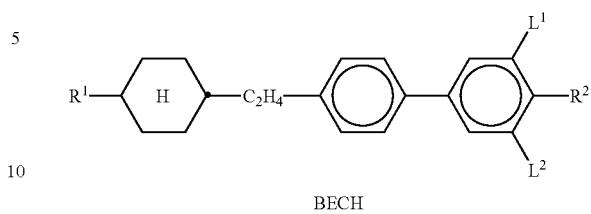
BECH
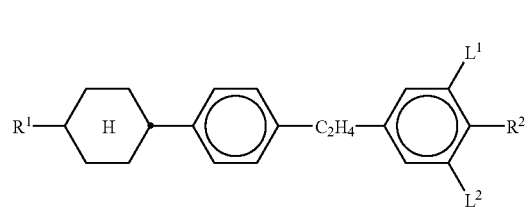
EBCH
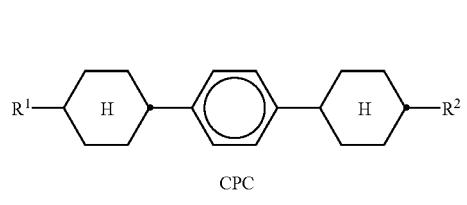
CPC
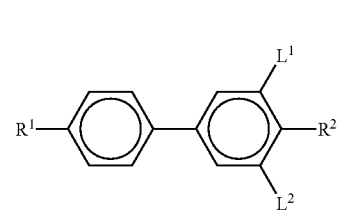
B
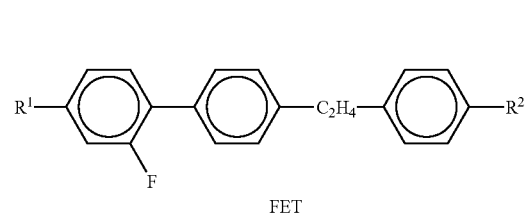
FET
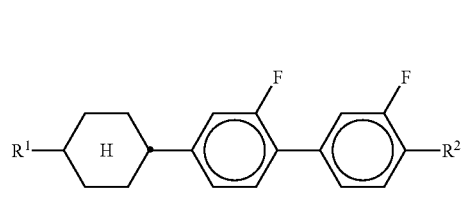
CGG
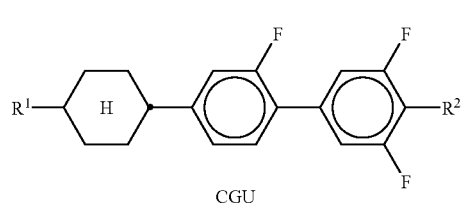
CGU
PTP TABLE A-continued
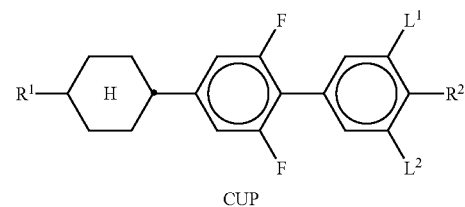
CUP
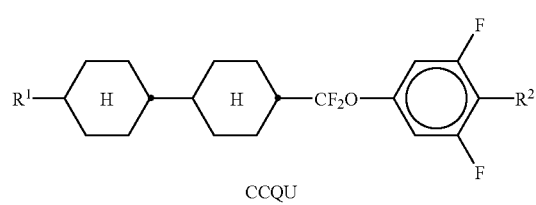
CCQU
TABLE A-continued
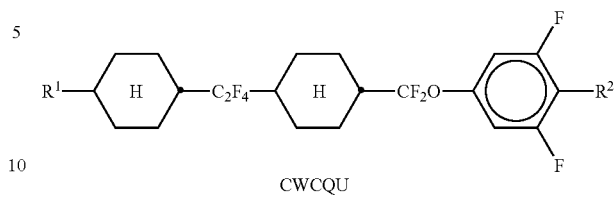
CWCQU
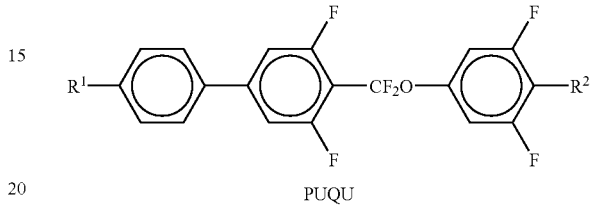
PUQU
TABLE B
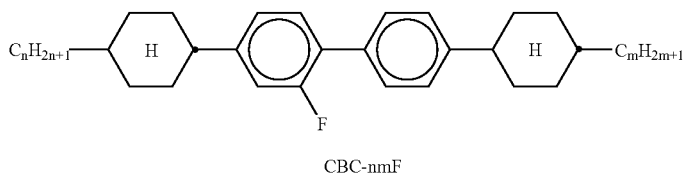
CBC-nmF
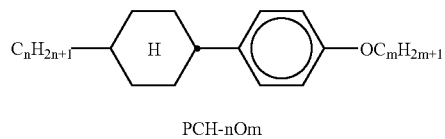
PCH-nOm
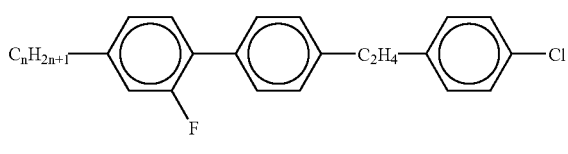
FET-nCl
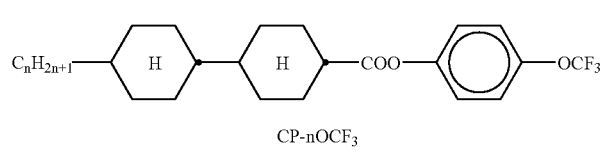
CP-nOCF$_3$
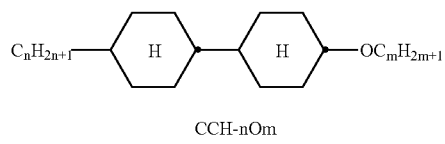
CCH-nOm
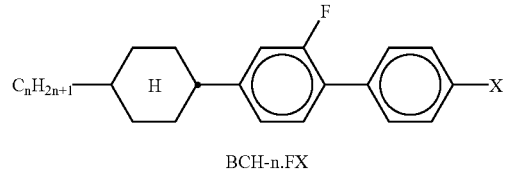
BCH-n.FX TABLE B-continued
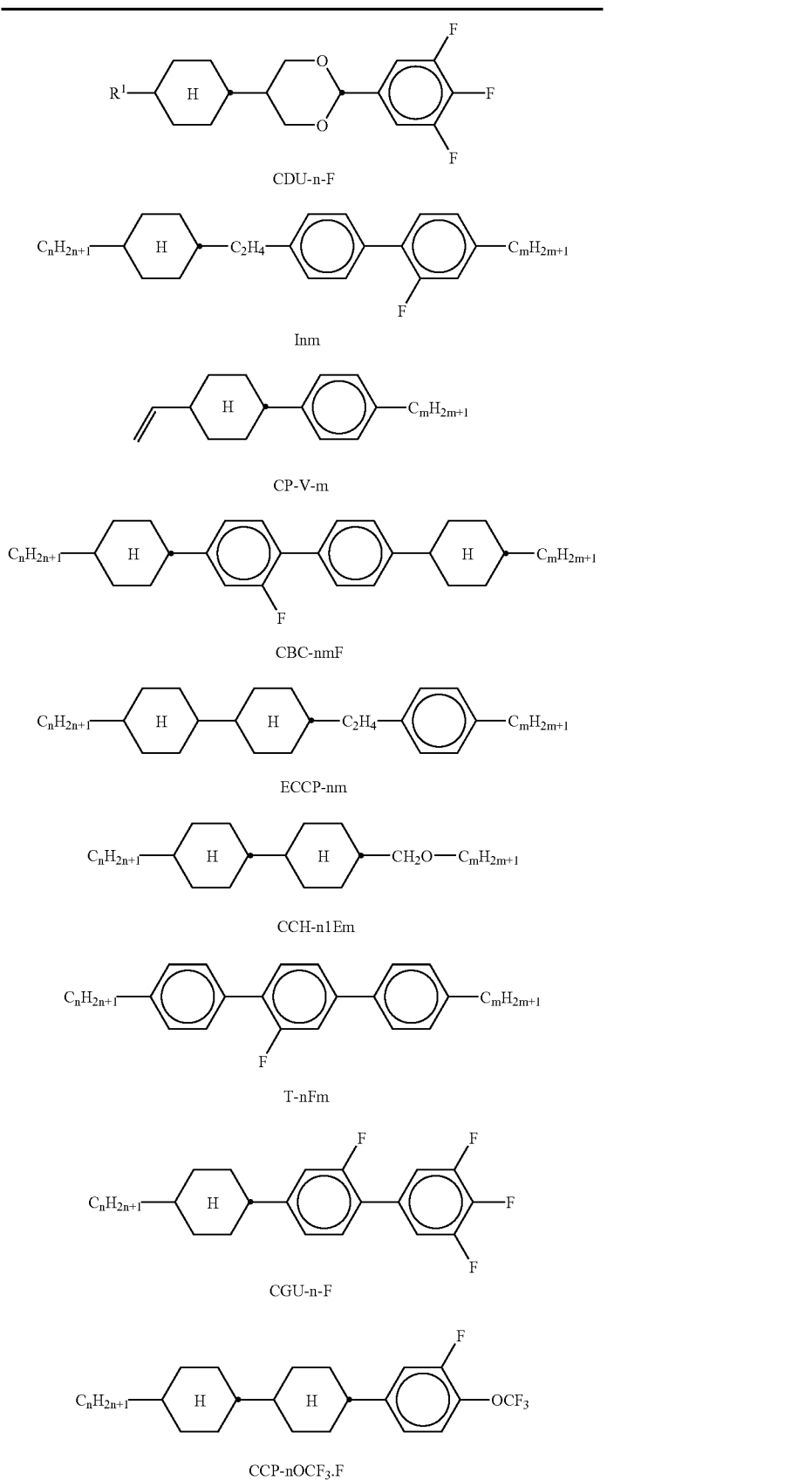

TABLE B-continued
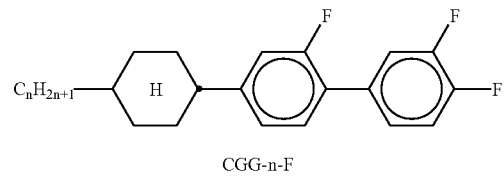
CGG-n-F
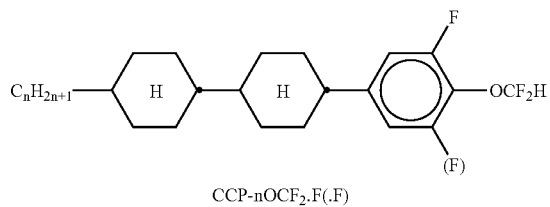
CCP-nOCF₂.F(.F)
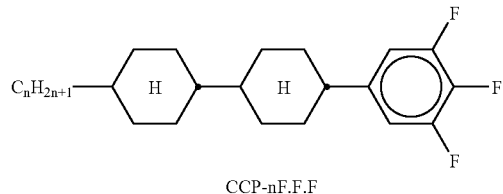
CCP-nF.F.F
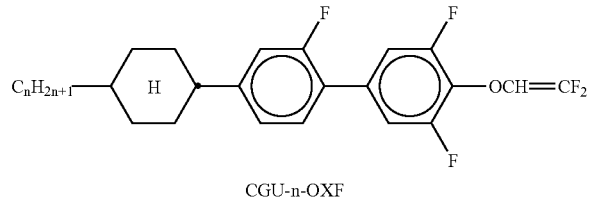
CGU-n-OXF
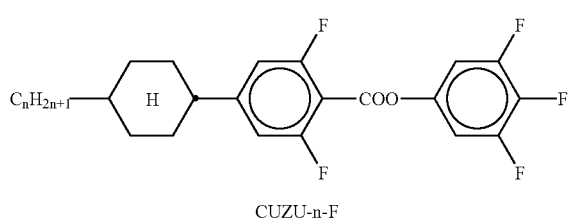
CUZU-n-F
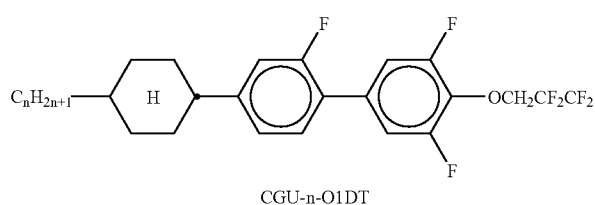
CGU-n-O1DT
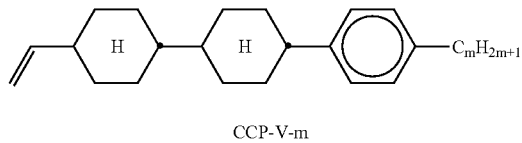
CCP-V-m TABLE B-continued
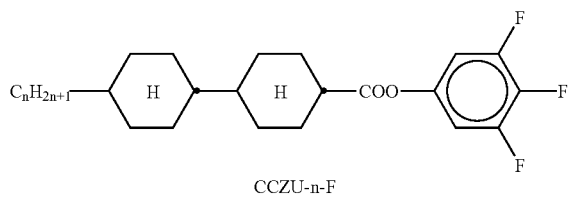
CCZU-n-F
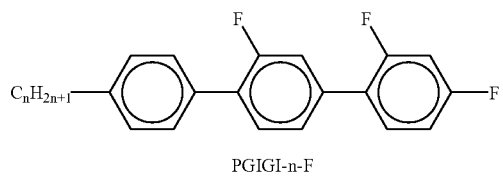
PGIGI-n-F
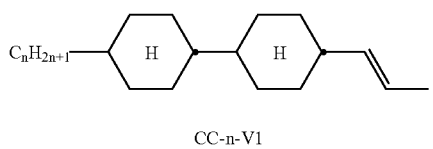
CC-n-V1
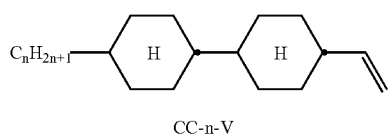
CC-n-V
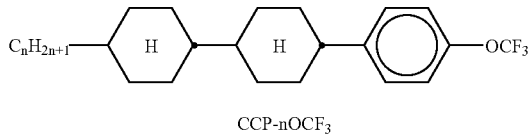
CCP-nOCF3
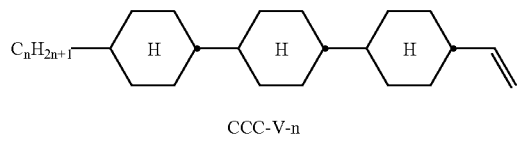
CCC-V-n
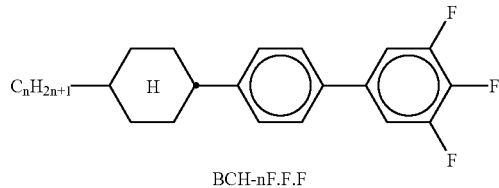
BCH-nF.F.F
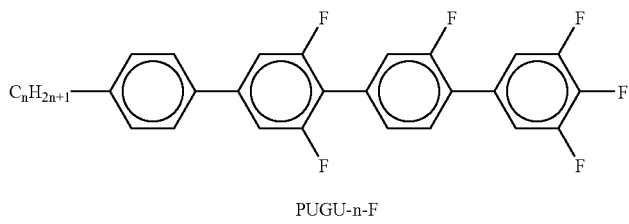
PUGU-n-F TABLE B-continued
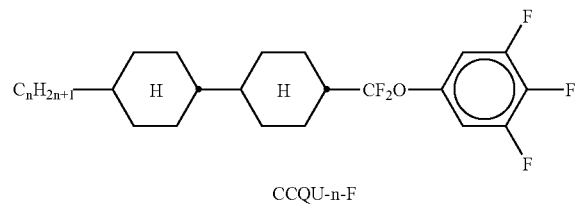
CCQU-n-F
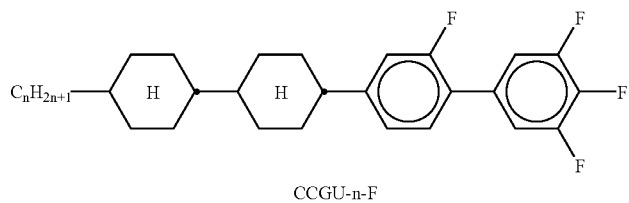
CCGU-n-F
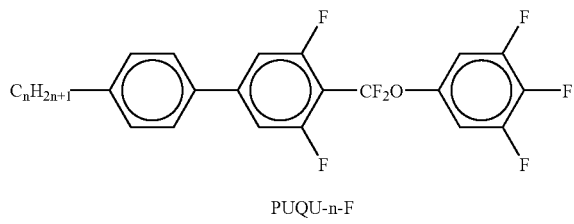
PUQU-n-F
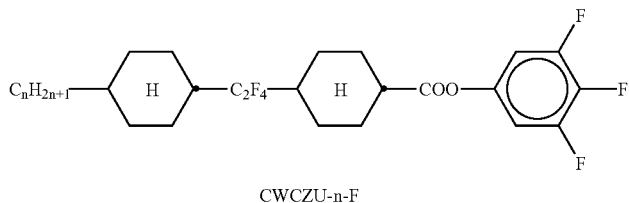
CWCZU-n-F
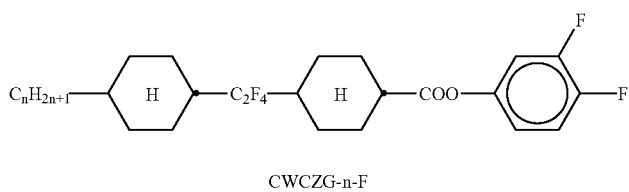
CWCZG-n-F
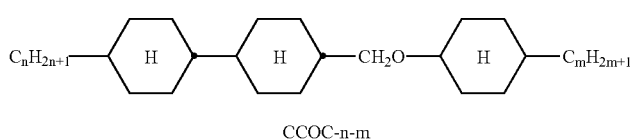
CCOC-n-m
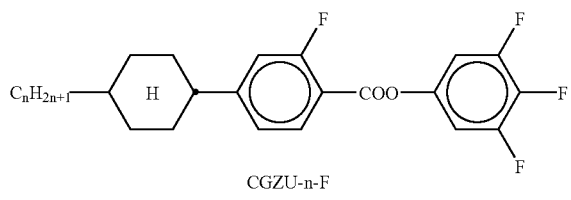
CGZU-n-F
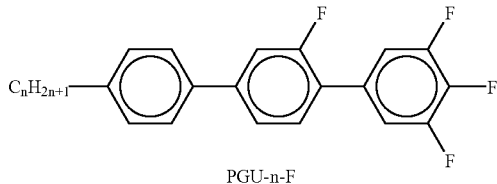
PGU-n-F TABLE B-continued
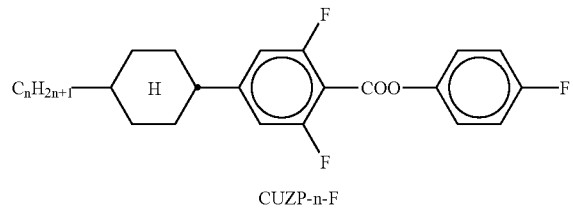
CUZP-n-F
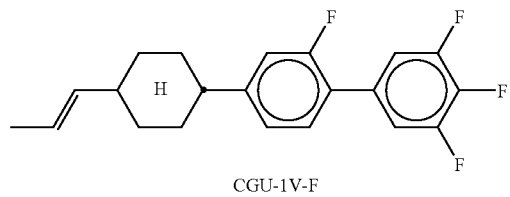
CGU-1V-F
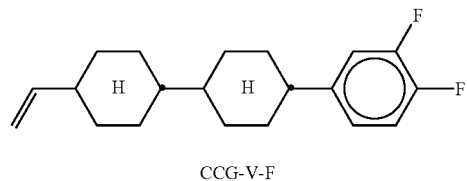
CCG-V-F
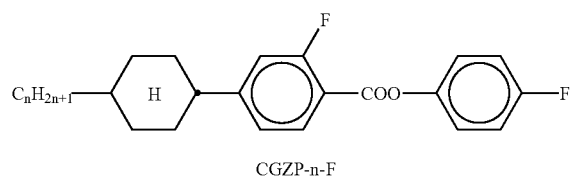
CGZP-n-F
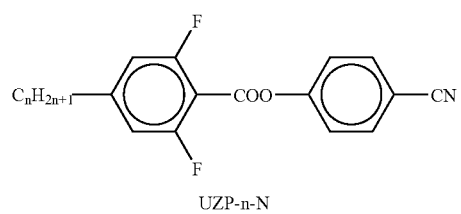
UZP-n-N
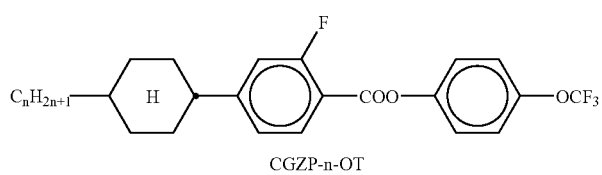
CGZP-n-OT
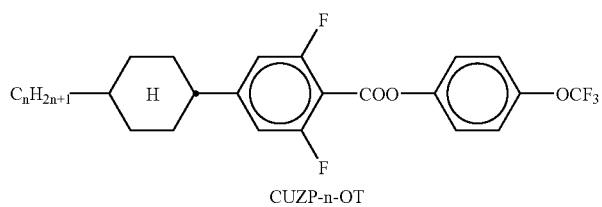
CUZP-n-OT TABLE B-continued
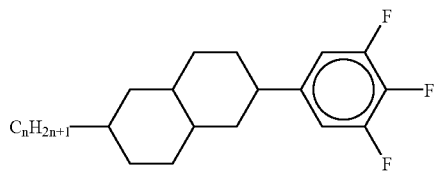
Dec-U-n-F
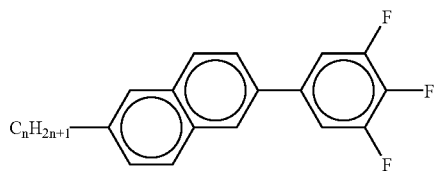
Nap-U-n-F
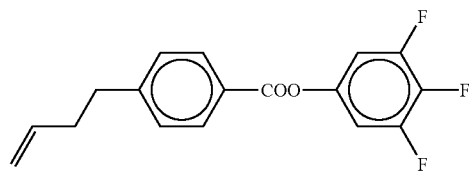
PZU-V2-F
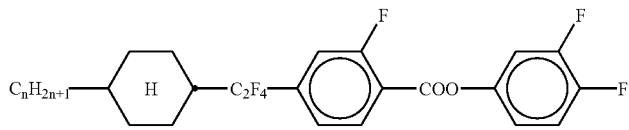
CWGZG-n-F
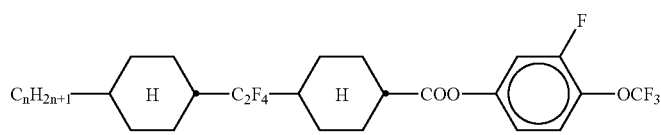
CWCZG-n-OT
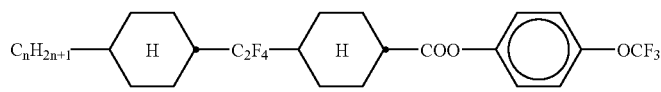
CWCZP-n-OT
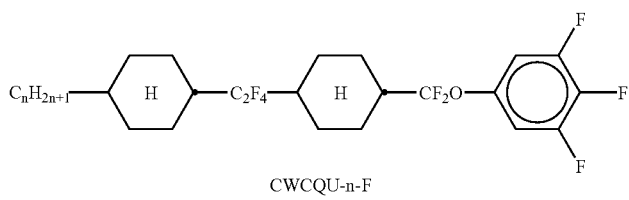
CWCQU-n-F
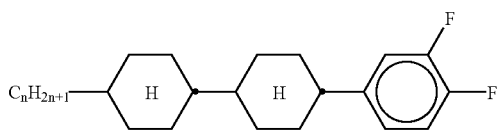
CCP-nF.F TABLE B-continued
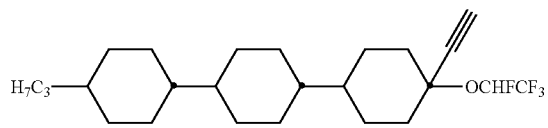
IS-8847
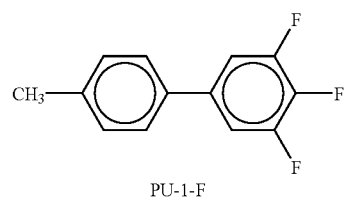
PU-1-F
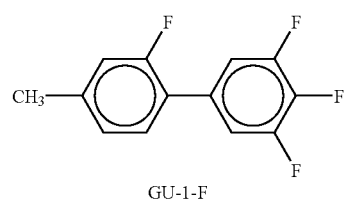
GU-1-F
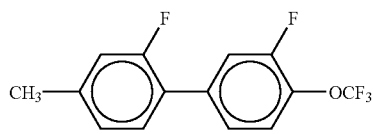
GG-1-OT
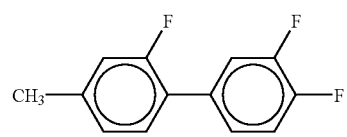
GG-1-F
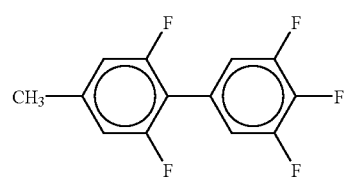
UU-1-F TABLE B-continued
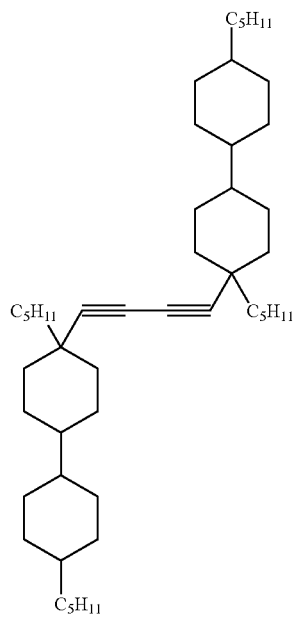
IS-7718
TABLE C
Table C shows possible dopants which are generally added to mixtures according to the invention.
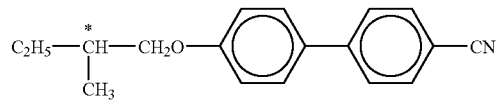
C 15
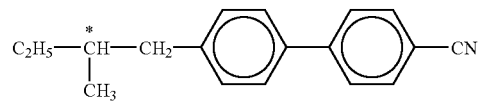
CB 15
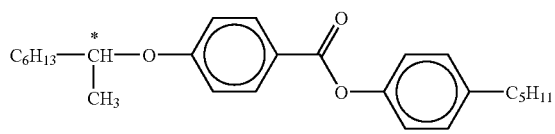
CM 21
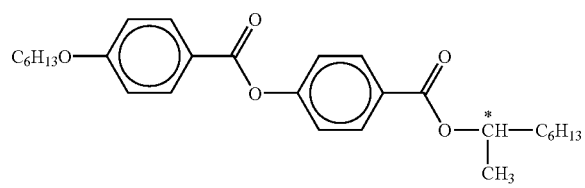
R/S-811

TABLE C-continued
Table C shows possible dopants which are generally added to mixtures according to the invention.
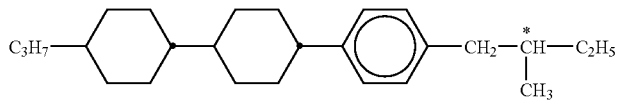
CM 44
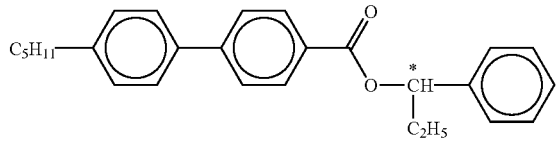
CM 45
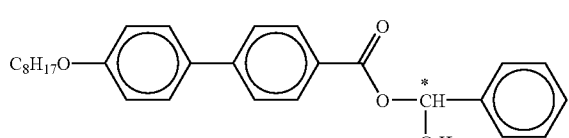
CM 47
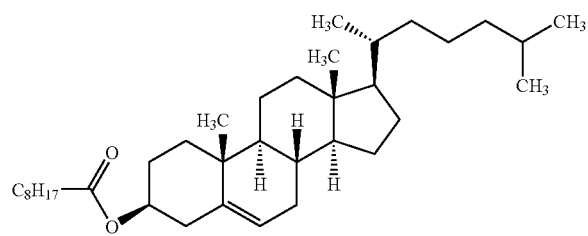
CN
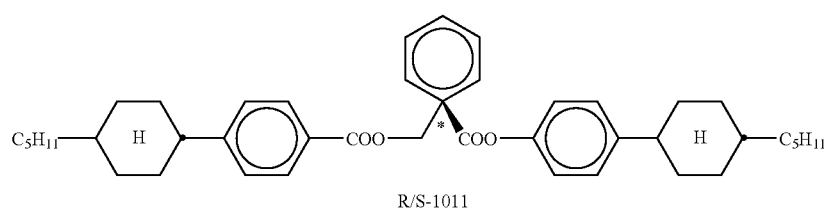
R/S-1011
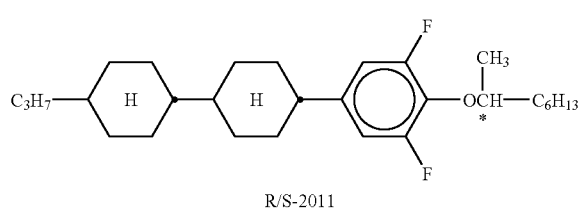
R/S-2011
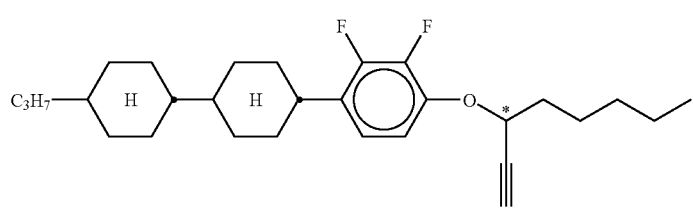
R/S-3011

TABLE C-continued
Table C shows possible dopants which are generally added to mixtures according to the invention.
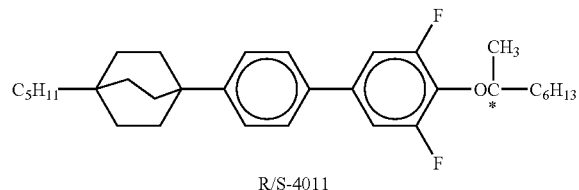
R/S-4011
TABLE D
Stabilisers which can be added, for example, to the mixtures according to the invention are indicated below.
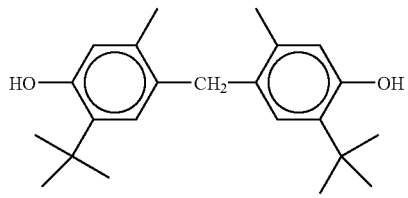
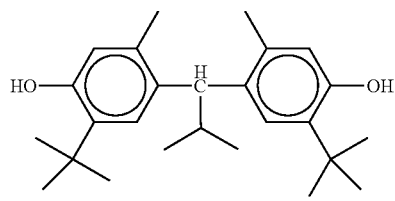
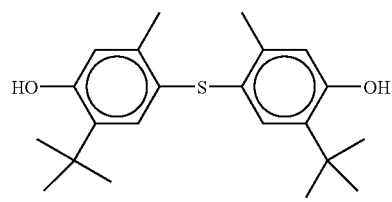
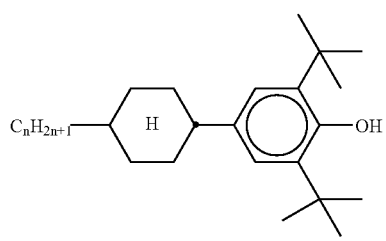
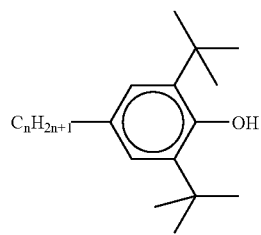

TABLE D-continued
Stabilisers which can be added, for example, to the mixtures according to the invention are indicated below.
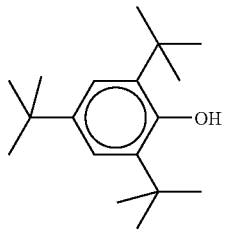
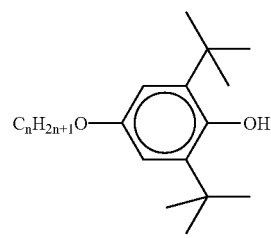
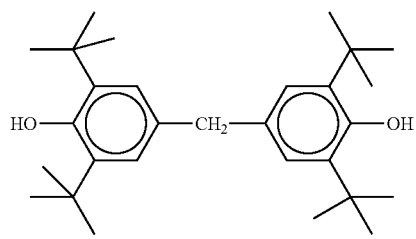
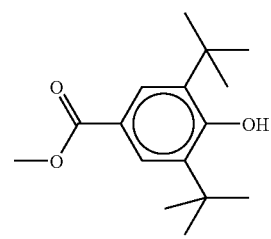
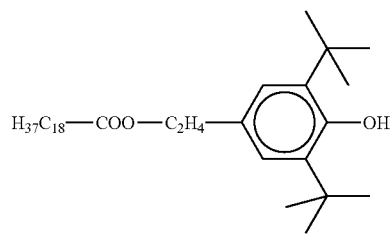
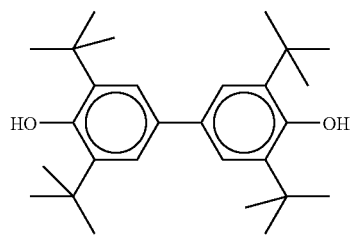

TABLE D-continued
Stabilisers which can be added, for example, to the mixtures according to the invention are indicated below.
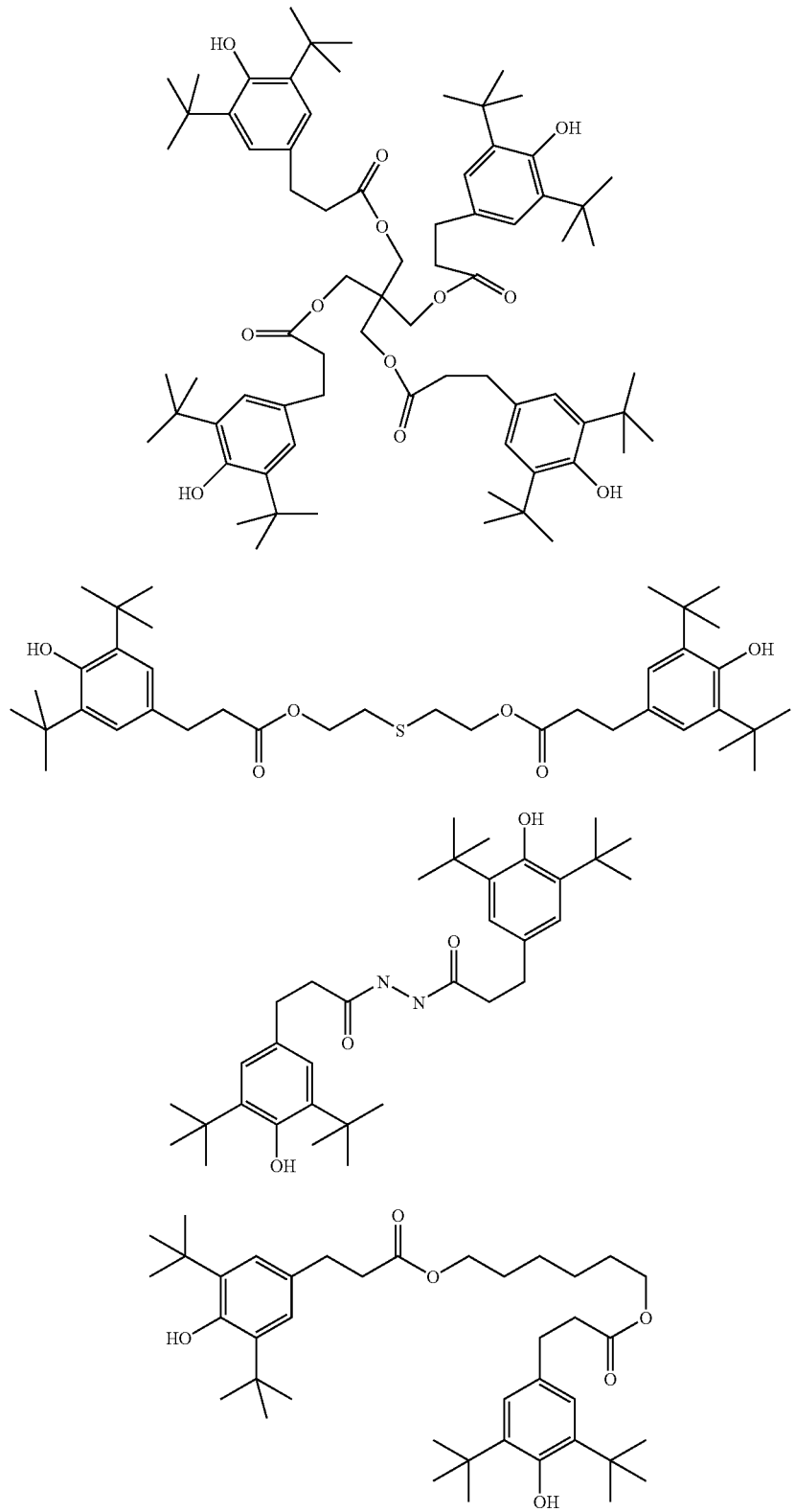

TABLE D-continued
Stabilisers which can be added, for example, to the mixtures according to the invention are indicated below.
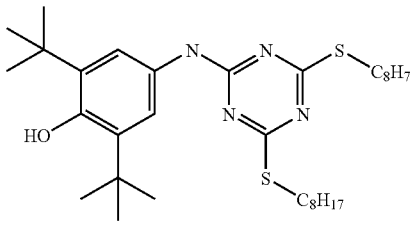
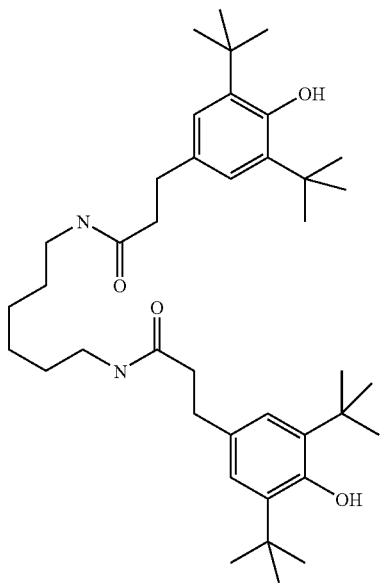
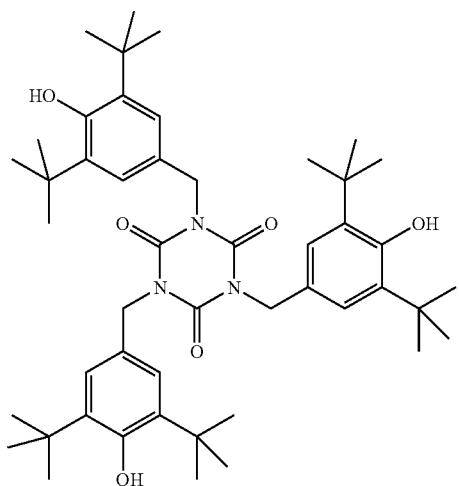

TABLE D-continued
Stabilisers which can be added, for example, to the mixtures according to the invention are indicated below.
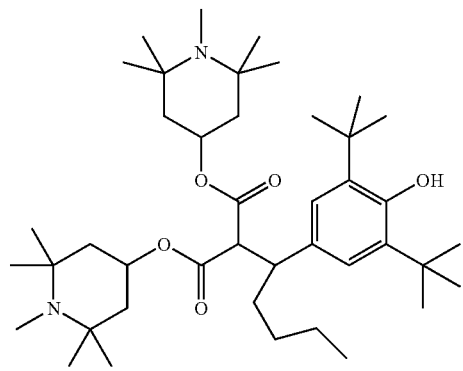
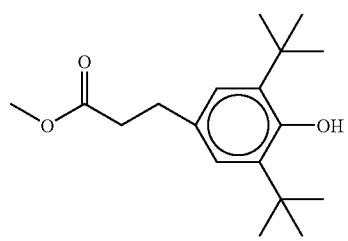
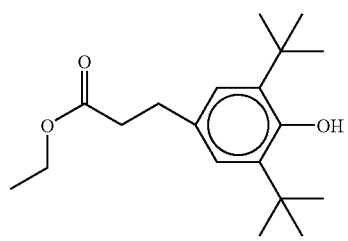
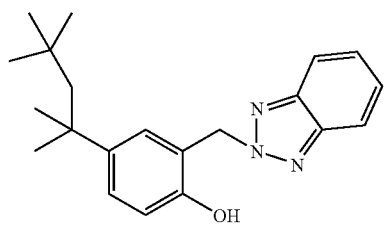
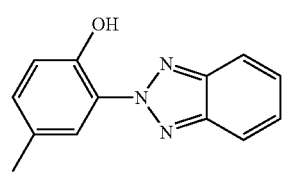
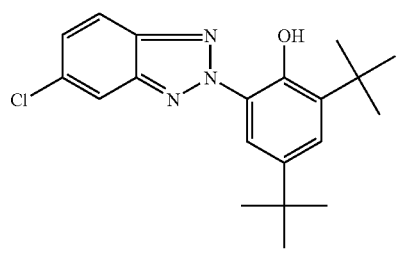

TABLE D-continued
Stabilisers which can be added, for example, to the mixtures according to the invention are indicated below.
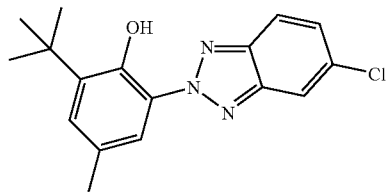
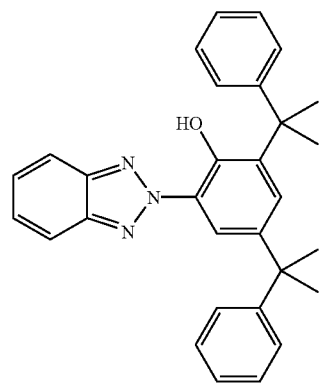
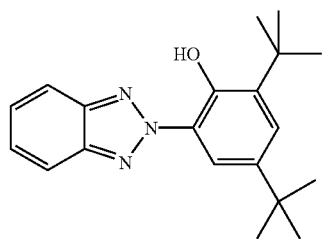
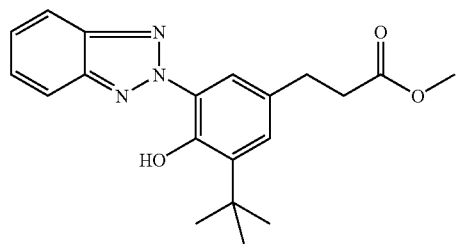
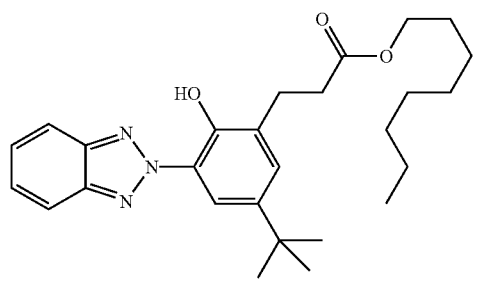

TABLE D-continued
Stabilisers which can be added, for example, to the mixtures according to the invention are indicated below.
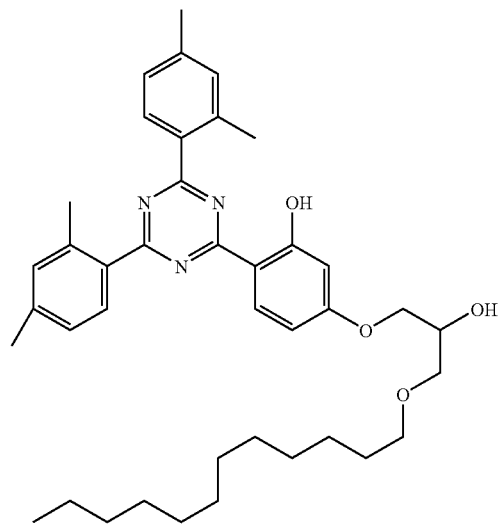
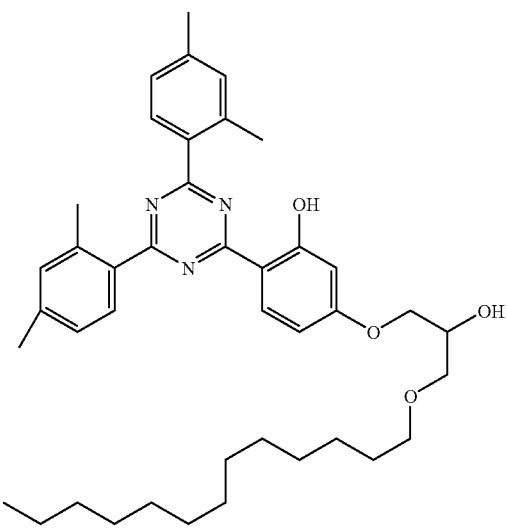
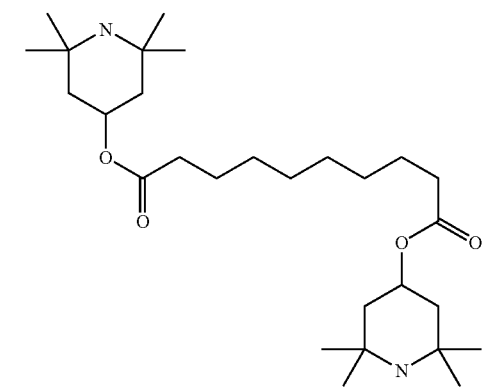

TABLE D-continued

Stabilisers which can be added, for example, to the mixtures
according to the invention are indicated below.

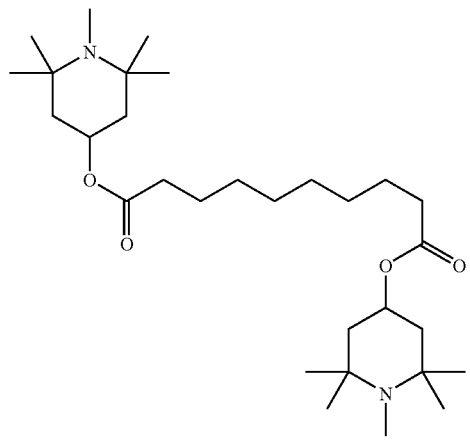

The following examples are intended to explain the invention without restricting it. Above and below, percentages are per cent by weight. All temperatures are given in degrees Celsius. m.p. denotes melting point, cl.p. denotes clearing point. Furthermore, C=crystalline state, N=nematic phase, S=smectic phase and I=isotropic phase. The data between these symbols represent the transition temperatures. Δn denotes optical anisotropy (589 nm, 20° C.), Δ∈ denotes dielectric anisotropy (1 kHz, 20° C.), the flow viscosity $v_{20}$ (mm$^2$/sec) was determined at 20° C. The rotational viscosity $\gamma_1$ [mPa·s] was likewise determined at 20° C.

"Conventional work-up" means that water is added if necessary, the mixture is extracted with dichloromethane, diethyl ether, methyl tert-butyl ether or toluene, the phases are separated, the organic phase is dried and evaporated, and the product is purified by distillation under reduced pressure or crystallisation and/or chromatography. The following abbreviations are used:

| | |
|---|---|
| n-BuLi | 1.6 molar solution of n-butyllithium in n-hexane |
| DMAP | 4-(dimethylamino)pyridine |
| THF | tetrahydrofuran |
| DCC | N,N'-dicyclohexylcarbodiimide |

EXAMPLE 1

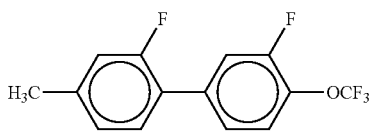

Step 1.1

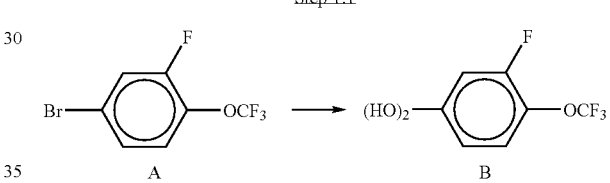

1.1 mol of magnesium turnings in 200 ml of abs. THF are heated under reflux, and 1.0 ml of A in 400 ml of abs. THF is added. The mixture is refluxed for 1 hour and cooled to 0–5° C., and a solution of 1.0 mol of trimethyl borate in 200 ml of abs. THF is added dropwise. The mixture is stirred at 0–5° C. for a further 15 minutes. After 200 ml of H$_2$O have been added, the mixture is acidified at 15° C. using conc. HCl, and 200 ml of methyl tert-butyl ether are added. Finally, the organic phase is subjected to conventional work-up.

Step 1.2

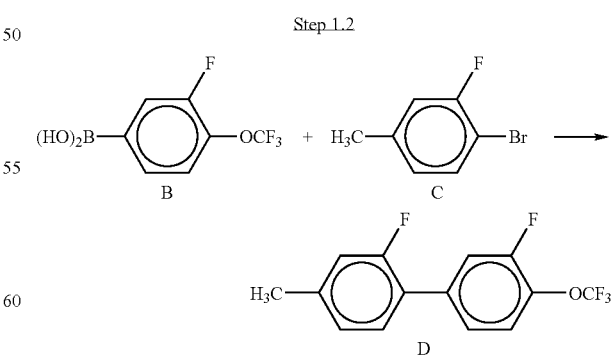

0.8 mmol of bis(triphenylphosphine)palladium, 0.82 mmol of hydrazinium hydroxide and 38.9 mmol of C are added to 29.6 mmol of sodium metaborate octahydrate in 39.5 ml of H$_2$O, and the mixture is stirred for 5 minutes.

After 38.8 mmol of B, dissolved in 60 ml of abs. THF, have been added, the mixture is refluxed overnight. The mixture is allowed to cool to room temperature, 30 ml of methyl tert-butyl ether are added, and the organic phase is separated off. Finally, the mixture is subjected to conventional work-up.

C 16 I; $\Delta n=0.1310$; $\Delta\epsilon=18.4$; $\gamma_1=26$; $\nu_{20}=8$

The following compounds are prepared analogously:

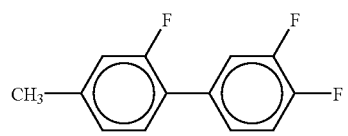
C 17 I; $\Delta n = 0.1338$; $\Delta\epsilon = 16.4$; $\gamma_1 = 16$

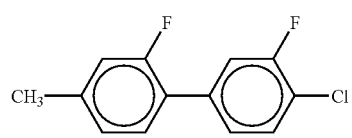

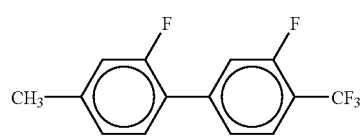

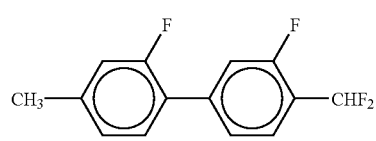

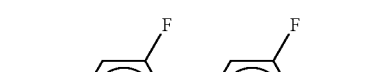

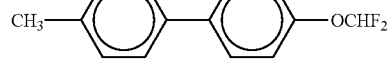

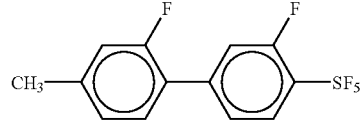

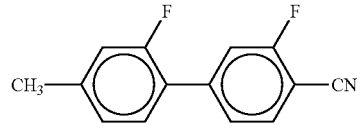

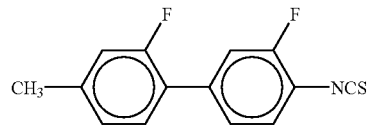

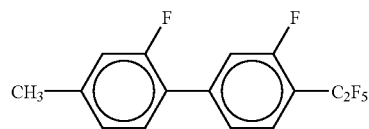

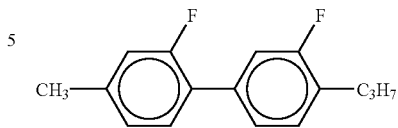

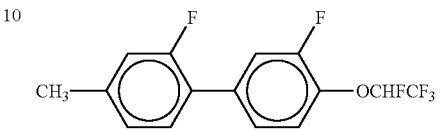

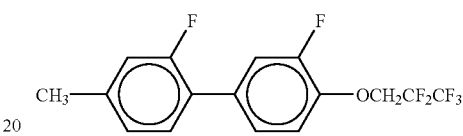

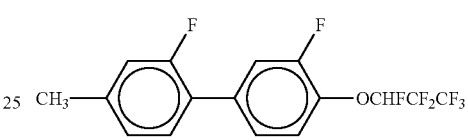

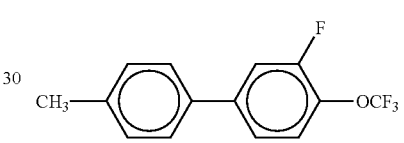

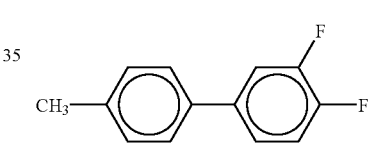
C 33 I; $\Delta n = 0.1545$; $\Delta\epsilon = 12.9$; $\gamma_1 = 22$; $\nu_{20} = 4$

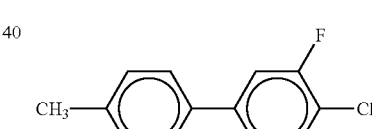
C 50 I; $\Delta n = 0.1625$; $\Delta\epsilon = 10.6$; $\gamma_1 = 12$; $\nu_{20} = 3$

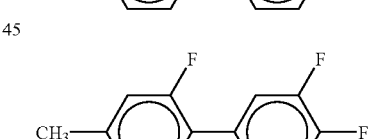
C 62 I; $\Delta n = 0.1647$; $\Delta\epsilon = 11.0$; $\gamma_1 = 27$; $\nu_{20} = 5$

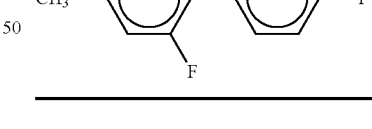
C 56 I; $\Delta n = 0.1207$; $\Delta\epsilon = 20.5$; $\gamma_1 = 22$; $\nu_{20} = 8$

EXAMPLE 2

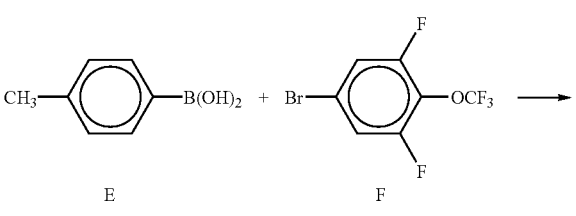

E         F

-continued

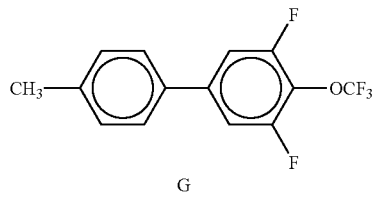

G 0.9 mmol of bis(triphenylphosphine)palladium, 0.8 mmol of hydrazinium hydroxide, 41.3 mmol of F and 30 ml of abs. THF are added to 31.4 mmol of sodium metaborate octahydrate in 42 ml of $H_2O$, and the mixture is stirred for 5 minutes.

After E, dissolved in 90 ml of abs. THF, has been added, the mixture is refluxed for 3 hours. The mixture is allowed to cool to room temperature, and water and methyl tert-butyl ether are added. The organic phase is separated off and subjected to conventional work-up.

C 37 I; $\Delta n=0.1413$; $\Delta\epsilon=17.0$; $\gamma_1=29$; $v_{20}=7$

The following compounds of the formula

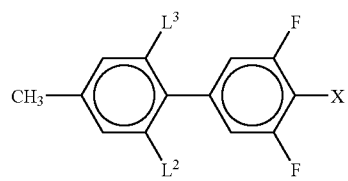

are prepared analogously:

| X | $L^2$ | $L^3$ | |
|---|---|---|---|
| $OCF_3$ | H | F | C 53 I; $\Delta n = 0.1223$; $\Delta\epsilon = 22.6$; $\gamma_1 = 37$; $v_{20} = 10$ |
| F | H | H | C 27 I; $\Delta n = 0.1388$; $\Delta\epsilon = 16.9$; $\gamma_1 = 13$; $v_{20} = 3$ |
| F | H | F | C 63 I; $\Delta n = 0.1227$; $\Delta\epsilon = 21.1$; $\gamma_1 = 15$; $v_{20} = 5$ |
| Cl | H | H | |
| Cl | H | F | |
| $CF_3$ | H | H | C 63 I; $\Delta n = 0.1530$; $\Delta\epsilon = 24.4$; $\gamma_1 = 31$ |
| $CF_3$ | H | F | C 67 I; $\Delta n = 0.1275$; $\Delta\epsilon = 28.2$; $\gamma_1 = 33$ |
| $CHF_2$ | H | H | |
| $CHF_2$ | H | F | |
| $OCHF_2$ | H | H | |
| $OCHF_2$ | H | F | |
| $SF_5$ | H | H | |
| $SF_5$ | H | F | |
| CN | H | H | |
| CN | H | F | |
| F | F | F | C 73 I; $\Delta n = 0.1013$; $\Delta\epsilon = 25.9$; $\gamma_1 = 22$ |
| $OCF_3$ | F | F | C 77 I; $\Delta n = 0.1088$; $\Delta\epsilon = 23.1$ |
| NCS | H | H | |
| NCS | H | F | |
| $C_2F_5$ | H | H | |
| $C_2F_5$ | H | F | |
| $C_3H_7$ | H | H | C 84 I; $\Delta n = 0.1387$; $\Delta\epsilon = 17.1$ |
| $C_3H_7$ | H | F | C 32 I; $\Delta n = 0.1215$; $\Delta\epsilon = 21.3$ |
| $OCHFCF_3$ | H | H | C 55 I; $\Delta n = 0.1417$; $\Delta\epsilon = 21.5$; $\gamma_1 = 56$ |
| $OCHFCF_3$ | H | F | C 20 I; $\Delta n = 0.1279$; $\Delta\epsilon = 25.3$; $\gamma_1 = 64$ |
| $OCH_2CF_2CF_3$ | H | H | |
| $OCH_2CF_2CF_3$ | H | F | |
| $OCHFCF_2CF_3$ | H | H | |
| $OCHFCF_2CF_3$ | H | F | |

MIXTURE EXAMPLES

Example M1

| | | | |
|---|---|---|---|
| CCH-35 | 4.00% | Clearing point [° C.]: | 80.5 |
| CC-3-V1 | 9.00% | $\Delta n$ [589 nm, 20° C.]: | 0.1043 |
| CC-5-V | 8.50% | $\gamma_1$ [mPa · s, 20° C.]: | 88 |
| CCP-2OCF$_3$ | 7.00% | $V_{10}$ [V]: | 1.37 |
| CCP-3OCF$_3$ | 7.00% | | |
| CCP-4OCF$_3$ | 4.00% | | |
| PGU-2-F | 8.50% | | |
| CCZU-3-F | 14.00% | | |
| CGZP-2-OT | 9.00% | | |
| CGZP-3-OT | 7.00% | | |
| GG-1-OT | 15.00% | | |
| BCH-32 | 4.00% | | |
| CBC-33 | 3.00% | | |

Example M2

| | | | |
|---|---|---|---|
| CCP-2F.F.F | 10.00% | S → N [° C.]: | <−40 |
| CCP-2OCF$_3$ | 7.00% | Clearing point [° C.]: | 78.0 |
| CCP-3OCF$_3$ | 7.00% | $\Delta n$ [589 nm, 20° C.]: | 0.0901 |
| CCP-4OCF$_3$ | 6.00% | $\gamma_1$ [mPa · s, 20° C.]: | 130 |
| CCP-2OCF$_3$.F | 12.00% | | |
| CCZU-2-F | 5.00% | | |
| CCZU-3-F | 15.00% | | |
| CCZU-5-F | 4.00% | | |
| CGZP-2-OT | 7.00% | | |
| CGZP-3-OT | 7.00% | | |
| CCGU-3-F | 4.00% | | |
| CCH-3CF$_3$ | 1.00% | | |
| GG-1-OT | 15.00% | | |

Example M3

| | |
|---|---|
| CCP-1F.F.F | 6.00% |
| CCP-2F.F.F | 7.00% |
| CCP-2OCF$_3$.F | 12.00% |
| CCZU-2-F | 5.00% |
| CCZU-3-F | 15.00% |
| CCZU-5-F | 5.00% |
| CGZP-1-OT | 12.00% |
| CGZP-2-OT | 8.00% |
| CGZP-3-OT | 6.00% |
| CCC-3-V | 9.00% |
| GG-1-OT | 15.00% |

Example M4

| | | | |
|---|---|---|---|
| CCP-1F.F.F | 5.00% | S → N [° C.]: | <−40 |
| CCP-2F.F.F | 8.00% | Clearing point [° C.]: | 82.0 |
| CCP-3F.F.F | 3.00% | $\Delta n$ [589 nm, 20° C.]: | 0.0887 |
| CCP-2OCF$_3$.F | 5.00% | $\gamma_1$ [mPa · s, 20° C.]: | 135 |
| CCP-2OCF$_3$ | 6.00% | | |
| CCP-3OCF$_3$ | 4.00% | | |
| CCZU-2-F | 4.00% | | |
| CCZU-3-F | 15.00% | | |
| CCZU-5-F | 5.00% | | |
| CGZP-2-OT | 11.00% | | |
| CGZP-3-OT | 9.00% | | |
| CCOC-3-3 | 4.00% | | |
| GG-1-OT | 11.00% | | |
| CCGU-3-F | 4.00% | | |
| CC-3-V | 6.00% | | |

Example M5

| | | | |
|---|---|---|---|
| CC-5-V | 7.00% | S → N [° C.]: | <−20 |
| CC-3-V1 | 10.00% | Clearing point [° C.]: | 74.5 |
| CCH-35 | 5.00% | $\Delta n$ [589 nm, 20° C.]: | 0.0773 |
| CC-3-V | 18.00% | $\gamma_1$ [mPa · s, 20° C.]: | 57 |
| GG-1-OT | 12.00% | $V_{10}$ [V]: | 1.84 |
| CCP-V-1 | 7.00% | | |
| CCZU-3-F | 15.00% | | |
| CCP-3OCF$_3$ | 8.00% | | |
| CCP-4OCF$_3$ | 8.00% | | |
| CGZP-2-OT | 10.00% | | |

Example M6

| | | | |
|---|---|---|---|
| CC-3-V | 6.00% | S → N [° C.]: | <−40 |
| CCP-2F.F.F | 7.00% | Clearing point [° C.]: | 71.0 |

| | | | | |
|---|---|---|---|---|
| CCP-3OCF₃ | 8.00% | Δn [589 nm, 20° C.]: | 0.0887 | |
| CCP-4OCF₃ | 6.00% | Δε [1 kHz, 20° C.]: | 12.3 | |
| CCZU-2-F | 5.00% | γ₁ [mPa · s, 20° C.]: | 108 | |
| CCZU-3-F | 15.00% | V₁₀ [V]: | 1.08 | |
| CCZU-5-F | 5.00% | | | |
| CGZP-2-OT | 11.00% | | | |
| CGZP-3-OT | 7.00% | | | |
| CCOC-3-3 | 3.00% | | | |
| CCOC-4-3 | 3.00% | | | |
| CCGU-3-F | 3.00% | | | |
| GG-1-OT | 21.00% | | | |

Example M7

| | | | | |
|---|---|---|---|---|
| CC-5-V | 4.00% | S → N [° C.]: | <-30 | |
| CC-3-V1 | 11.00% | Clearing point [° C.]: | 78.0 | |
| CCH-35 | 5.00% | Δn [589 nm, 20° C.]: | 0.0781 | |
| CC-3-V | 18.00% | γ₁ [mPa · s, 20° C.]: | 61 | |
| GG-1-OT | 12.00% | V₁₀ [V]: | 1.78 | |
| CCZU-2-F | 4.00% | | | |
| CCZU-3-F | 15.00% | | | |
| CCP-3OCF₃ | 8.00% | | | |
| CCP-4OCF₃ | 8.00% | | | |
| CGZP-2-OT | 7.00% | | | |
| CBC-33 | 1.00% | | | |
| CCP-V-1 | 7.00% | | | |

Example M8

| | |
|---|---|
| GG-1-OT | 10.00% |
| CC-5-V | 5.00% |
| CC-3-V1 | 5.00% |
| CGU-2-F | 11.00% |
| CGU-3-F | 11.00% |
| CGU-5-F | 9.00% |
| BCH-3F.F.F | 15.00% |
| BCH-5F.F.F | 10.00% |
| PGU-2-F | 9.00% |
| PGU-3-F | 5.00% |
| CCP-V-1 | 10.00% |

Example M9

| | | | |
|---|---|---|---|
| CC-3-V | 9.50% | Clearing point [° C.]: | 73.0 |
| GG-1-OT | 12.00% | Δn [589 nm, 20° C.]: | 0.1472 |
| PGU-2-F | 11.00% | Δε [kHz, 20° C.]: | 12.0 |
| PGU-3-F | 11.00% | γ₁ [mPa · s, 20° C.]: | 106 |
| PGU-5-F | 10.00% | V₀ [V]: | 1.02 |
| CGZP-2-OT | 10.00% | | |
| CGZP-3-OT | 4.00% | | |
| BCH-2F.F | 6.00% | | |
| PGIGI-3-F | 3.00% | | |
| BCH-32 | 6.00% | | |
| CCP-V-1 | 15.00% | | |
| CBC-33 | 2.50% | | |

Example M10

| | | | |
|---|---|---|---|
| CC-3-V | 2.00% | Clearing point [° C.]: | 69.5 |
| CCP-2F.F.F | 9.00% | Δn [589 nm, 20° C.]: | 0.0889 |
| CCP-2OCF₃.F | 7.00% | γ₁ [mPa · s, 20° C.]: | 118 |
| CCP-3OCF₃ | 6.00% | V₁₀ [V]: | 1.03 |
| CCP-4OCF₃ | 6.00% | | |
| PGU-2-F | 1.00% | | |
| CCZU-2-F | 5.00% | | |
| CCZU-3-F | 15.00% | | |
| CCZU-5-F | 5.00% | | |
| CGZP-2-OT | 11.00% | | |
| CGZP-3-OT | 9.00% | | |
| CCOC-3-3 | 2.00% | | |
| CCOC-4-3 | 3.00% | | |
| GG-1-OT | 19.00% | | |

Example M11

| | |
|---|---|
| CC-3-V | 15.00% |
| CCGU-3-F | 3.00% |
| CCP-3OCF₃ | 8.00% |
| CCP-4OCF₃ | 6.00% |
| CCZU-2-F | 5.00% |
| CCZU-3-F | 15.00% |
| CCZU-5-F | 5.00% |
| CGZP-2-OT | 11.00% |
| CGZP-3-OT | 9.00% |
| CCOC-3-3 | 3.00% |
| GG-1-OT | 20.00% |

Example M12

| | |
|---|---|
| CC-5-V | 6.00% |
| CC-3-V1 | 10.00% |
| CCH-35 | 5.00% |
| CC-3-V | 18.00% |
| GG-1-OT | 12.00% |
| CCP-V-1 | 4.00% |
| CCZU-3-F | 14.00% |
| CCP-3OCF₃ | 8.00% |
| CCP-4OCF₃ | 8.00% |
| CCP-5OCF₃ | 4.00% |
| CGZP-2-OT | 10.00% |
| CBC-33 | 1.00% |

Example M13

| | | | |
|---|---|---|---|
| CC-5-V | 8.50% | S → N [° C.]: | <-20 |
| CC-3-V1 | 11.00% | Clearing point [° C.]: | 78.5 |
| CCH-35 | 5.00% | Δn [589 nm, 20° C.]: | 0.0791 |
| CC-3-V | 18.00% | γ₁ [mPa · s, 20° C.]: | 61 |
| GG-1-OT | 12.00% | V₁₀ [V]: | 1.80 |
| CCZU-3-F | 15.50% | | |
| CCP-3OCF₃ | 8.00% | | |
| CCP-4OCF₃ | 8.00% | | |
| CGZP-2-OT | 10.00% | | |
| CBC-33 | 4.00% | | |

Example M14

| | | | |
|---|---|---|---|
| CC-5-V | 3.50% | S → N [° C.]: | <-30 |
| CC-3-V1 | 11.00% | Clearing point [° C.]: | 78.5 |
| CCH-35 | 5.00% | Δn [589 nm, 20° C.]: | 0.0791 |
| CC-3-V | 18.00% | γ₁ [mPa · s, 20° C.]: | 61 |
| GG-1-OT | 12.00% | V₁₀ [V]: | 1.76 |
| CCZU-2-F | 4.00% | | |
| CCZU-3-F | 15.00% | | |
| CCP-3OCF₃ | 8.00% | | |
| CCP-4OCF₃ | 8.00% | | |
| CGZP-2-OT | 8.00% | | |
| CBC-33 | 1.50% | | |
| CCP-V-1 | 6.00% | | |

Example M15

| | | | |
|---|---|---|---|
| CC-3-V | 6.00% | S → N [° C.]: | <-12.0 |
| GG-1-OT | 10.00% | Clearing point [° C.]: | 75.0 |
| PGU-2-F | 9.00% | Δn [589 nm, 20° C.]: | 0.1532 |
| PGU-3-F | 10.00% | | |
| PGU-5-F | 9.00% | | |
| CGZP-2-OT | 9.00% | | |
| CGZP-3-OT | 4.00% | | |
| BCH-3F.F.F | 12.00% | | |
| PGIGI-3-F | 9.00% | | |
| BCH-32 | 5.00% | | |
| CCP-V-1 | 15.00% | | |
| CBC-33 | 2.00% | | |

Example M16

| | |
|---|---|
| CCP-2F.F.F | 13.00% |
| CCP-3F.F.F | 11.00% |
| CCP-5F.F.F | 6.00% |
| CCZU-2-F | 4.00% |
| CCZU-3-F | 15.00% |
| CCZU-5-F | 4.00% |
| CCP-2OCF₃.F | 6.00% |
| CCP-3OCF₃.F | 5.00% |
| CGU-2-F | 3.00% |
| CGU-3-F | 2.00% |
| CCOC-3-3 | 2.00% |
| CCOC-4-3 | 2.00% |
| CC-5-V | 4.00% |
| CCH-3CF₃ | 7.00% |
| GG-1-OT | 4.00% |
| IS-8847 | 12.00% |

Example M17

| | |
|---|---|
| CCH-35 | 5.00% |
| CC-3-V1 | 9.00% |
| CC-5-V | 9.00% |

| | |
|---|---|
| CCP-2OCF₃ | 7.00% |
| CCP-3OCF₃ | 7.00% |
| CCP-4OCF₃ | 4.00% |
| PGU-2-F | 8.00% |
| CCZU-3-F | 12.00% |
| CGZP-2-OT | 10.00% |
| CGZP-3-OT | 7.00% |
| GG-1-OT | 14.00% |
| BCH-32 | 5.00% |
| CBC-33 | 3.00% |

Example M18

| | |
|---|---|
| CCP-2F.F.F | 12.00% |
| CCP-3F.F.F | 12.00% |
| CCP-5F.F.F | 6.00% |
| CCZU-2-F | 4.00% |
| CCZU-3-F | 16.00% |
| CCZU-5-F | 4.00% |
| CCP-2OCF₃.F | 6.00% |
| CCP-5OCF₃F | 6.00% |
| CGU-2-F | 3.00% |
| CGU-3-F | 7.00% |
| CCOC-3-3 | 3.00% |
| CCOC-4-3 | 3.00% |
| IS-8847 | 12.00% |
| GG-1-OT | 6.00% |

Example M19

| | |
|---|---|
| CCP-2F.F.F | 13.00% |
| CCP-3F.F.F | 11.00% |
| CCP-5F.F.F | 6.00% |
| CCP-2OCF₃.F | 11.00% |
| CCP-5OCF₃.F | 12.00% |
| CGU-3-F | 5.00% |
| CCOC-3-3 | 3.00% |
| CCOC-4-3 | 4.00% |
| CCOC-3-5 | 2.00% |
| CCH-3CF₃ | 6.00% |
| CCH-5CF₃ | 6.00% |
| GG-1-OT | 6.00% |
| IS-8847 | 15.00% |

Example M20

| | |
|---|---|
| CCP-2F.F.F | 13.00% |
| CCP-3F.F.F | 11.00% |
| CCP-5F.F.F | 6.00% |
| CCP-2OCF₃.F | 12.00% |
| CCP-3OCF₃.F | 12.00% |
| CCP-5OCF₃.F | 12.00% |
| CGU-2-F | 5.00% |
| CCOC-3-3 | 3.00% |
| CCOC-4-3 | 3.00% |
| CCOC-3-5 | 2.00% |
| CCH-5CF₃ | 5.00% |
| GG-1-OT | 8.00% |
| IS-7718 | 8.00% |

Example M21

| | |
|---|---|
| CCP-2F.F.F | 11.00% |
| CCP-3F.F.F | 13.00% |
| CCP-5F.F.F | 6.00% |
| CCZU-2-F | 5.00% |
| CCZU-3-F | 16.00% |
| CCZU-5-F | 4.00% |
| CCP-3OCF₃.F | 3.00% |
| CCP-5OCF₃.F | 12.00% |
| CGU-2-F | 4.00% |
| CGU-3-F | 12.00% |
| CCOC-4-3 | 3.00% |
| IS-7718 | 8.00% |
| GG-1-OT | 3.00% |

Example M22

| | |
|---|---|
| CCP-2F.F.F | 13.00% |
| CCP-3F.F.F | 11.00% |
| CCP-5F.F.F | 6.00% |
| CCZU-2-F | 5.00% |
| CCZU-3-F | 16.00% |
| CCZU-5-F | 4.00% |
| CCP-2OCF₃.F | 6.00% |
| CCP-5OCF₃.F | 7.00% |
| CCOC-3-3 | 3.00% |
| CCOC-4-3 | 4.00% |
| CCOC-3-5 | 2.00% |
| GG-1-OT | 7.00% |
| IS-7718 | 8.00% |
| CCH-3CF₃ | 4.00% |
| CCH-5CF₃ | 4.00% |

Example M23

| | |
|---|---|
| CCP-2F.F.F | 13.00% |
| CCP-3F.F.F | 11.00% |
| CCP-5F.F.F | 6.00% |
| CCZU-2-F | 5.00% |
| CCZU-3-F | 16.00% |
| CCZU-5-F | 4.00% |
| CCP-2OCF₃.F | 5.00% |
| CCP-5OCF₃.F | 4.00% |
| CCOC-3-3 | 2.00% |
| CCOC-4-3 | 2.00% |
| GG-1-OT | 3.00% |
| IS-8847 | 15.00% |
| CCH-3CF₃ | 8.00% |
| CCH-5CF₃ | 6.00% |

Example M24

| | | | |
|---|---|---|---|
| PGU-2-F | 6.00% | S → N [° C.]: | <-40 |
| CGZP-2-OT | 9.00% | Clearing point [° C.]: | 73.5 |
| BCH-3F.F.F | 6.00% | Δn [589 nm, 20° C.]: | 0.0910 |
| CCP-2F.F.F | 9.00% | γ₁ [mPa · s, 20° C.]: | 77 |
| CCG-V-F | 4.00% | V₀ [V]: | 1.44 |
| CCZU-2-F | 3.00% | | |
| CCZU-3-F | 13.00% | | |
| CCP-V-1 | 6.00% | | |
| CC-3-V1 | 11.00% | | |
| CC-5-V | 16.00% | | |
| CCH-35 | 4.00% | | |
| GG-1-OT | 10.00% | | |
| CBC-33 | 3.00% | | |

Example M25

| | | | |
|---|---|---|---|
| CC-3-V | 10.00% | S → N [° C.]: | <-30 |
| GG-1-OT | 12.00% | Clearing point [° C.]: | 75.0 |
| PGU-2-F | 11.00% | Δn [589 nm, 20° C.]: | 0.1467 |
| PGU-3-F | 11.00% | γ₁ [mPa · s, 20° C.]: | 116 |
| PGU-5-F | 9.00% | | |
| CGZP-2-OT | 7.50% | | |
| CGZP-3-OT | 6.50% | | |
| BCH-3F.F.F | 5.50% | | |
| PGIGI-3-F | 4.00% | | |
| BCH-32 | 4.00% | | |
| CCP-V-1 | 15.00% | | |
| CBC-33 | 2.00% | | |
| CBC-33F | 2.50% | | |

Example M26

| | |
|---|---|
| CCP-2F.F.F | 13.00% |
| CCP-3F.F.F | 11.00% |
| CCP-5F.F.F | 6.00% |
| CCP-2OCF₃.F | 11.00% |
| CCP-5OCF₃.F | 12.00% |
| CGU-2-F | 7.00% |
| CGU-3-F | 8.00% |
| CCOC-3-3 | 3.00% |
| CCOC-4-3 | 4.00% |
| CCOC-3-5 | 2.00% |
| GG-1-OT | 8.00% |
| IS-8847 | 15.00% |

Example M27

| | |
|---|---|
| CCP-2F.F.F | 13.00% |
| CCP-3F.F.F | 11.00% |
| CCP-5F.F.F | 6.00% |
| CCP-2OCF₃.F | 12.00% |
| CCP-3OCF₃.F | 12.00% |
| CCP-5OCF₃.F | 12.00% |
| CGU-2-F | 4.00% |
| CCH-5CF₃ | 2.00% |

-continued

| | |
|---|---|
| GG-1-OT | 11.00% |
| IS-7718 | 8.00% |
| CCGU-3-F | 9.00% |

Example M28

| | |
|---|---|
| CCP-1F.F.F | 5.00% |
| CCP-2F.F.F | 8.00% |
| CCP-3F.F.F | 3.00% |
| CCP-2OCF$_3$.F | 5.00% |
| CCP-2OCF$_3$ | 6.00% |
| CCP-3OCF$_3$ | 4.00% |
| CCZU-2-F | 4.00% |
| CCZU-3-F | 15.00% |
| CCZU-5-F | 5.00% |
| CGZP-2-OT | 11.00% |
| CGZP-3-OT | 9.00% |
| CCOC-3-3 | 4.00% |
| GG-1-OT | 11.00% |
| CCGU-3-F | 4.00% |
| CC-3-V | 6.00% |

Example M29

| | | | |
|---|---|---|---|
| CCP-2F.F.F | 10.00% | S → N [° C.]: | <-40 |
| CCP-2OCF$_3$ | 6.00% | Clearing point [° C.]: | 75.5 |
| CCP-3OCF$_3$ | 6.00% | Δn [589 nm, 20° C.]: | 0.0884 |
| CCP-4OCF$_3$ | 4.00% | γ$_1$ [mPa · s, 20° C.]: | 134 |
| CCP-2OCF$_3$.F | 12.00% | V$_{10}$ [V]: | 1.09 |
| CCP-3OCF$_3$.F | 4.00% | | |
| CCZU-2-F | 5.00% | | |
| CCZU-3-F | 15.00% | | |
| CCZU-5-F | 4.00% | | |
| CGZP-2-OT | 8.00% | | |
| CGZP-3-OT | 7.00% | | |
| CCGU-3-F | 3.00% | | |
| CCH-3CF$_3$ | 2.00% | | |
| GG-1-F | 10.00% | | |
| CGU-2-F | 4.00% | | |

Example M30

| | | | |
|---|---|---|---|
| CC-5-V | 8.00% | S → N [° C.]: | <-30 |
| CC-3-V1 | 11.00% | Clearing point [° C.]: | 76.0 |
| CCH-35 | 5.00% | Δn [589 nm, 20° C.]: | 0.0765 |
| CC-3-V | 18.00% | γ$_1$ [mPa · s, 20° C.]: | 60 |
| GG-1-F | 9.00% | V$_{10}$ [V]: | 1.79 |
| CCZU-2-F | 4.00% | | |
| CCZU-3-F | 15.00% | | |
| CCP-2OCF$_3$ | 3.00% | | |
| CCP-3OCF$_3$ | 8.00% | | |
| CCP-5OCF$_3$ | 6.00% | | |
| CGZP-2-OT | 11.00% | | |
| CBC-33 | 2.00% | | |

Example M31

| | | | |
|---|---|---|---|
| CC-3-V | 4.00% | Clearing point [° C.]: | 70.0 |
| CCP-2F.F.F | 10.00% | Δn [589 nm, 20° C.]: | 0.0878 |
| CCP-3OCF$_3$ | 8.00% | V$_{10}$ [V]: | 1.04 |
| CCP-4OCF$_3$ | 6.00% | | |
| CCZU-2-F | 5.00% | | |
| CCZU-3-F | 15.00% | | |
| CCZU-5-F | 5.00% | | |
| CGZP-2-OT | 11.00% | | |
| CGZP-3-OT | 9.00% | | |
| CCOC-3-3 | 3.00% | | |
| CCOC-4-3 | 3.00% | | |
| CCGU-3-F | 3.00% | | |
| GG-1-F | 18.00% | | |

Example M32

| | |
|---|---|
| CC-3-V1 | 10.00% |
| CC-5-V | 3.50% |
| CCH-35 | 5.00% |
| CC-3-V | 18.00% |
| GG-1-F | 8.00% |
| PGU-2-F | 11.00% |
| CGZP-2-OT | 11.00% |
| CGZP-3-OT | 4.50% |
| CCZU-2-F | 4.00% |
| CCZU-3-F | 14.00% |
| CCP-3OCF$_3$ | 8.00% |
| CBC-33 | 3.00% |

Example M33

| | |
|---|---|
| PGU-2-F | 8.00% |
| CCP-2OCF$_3$ | 8.00% |
| CCP-3OCF$_3$ | 8.00% |
| CCP-4OCF$_3$ | 6.00% |
| CCP-5OCF$_3$ | 7.00% |
| CCP-2F.F.F | 10.00% |
| CCP-3OCF$_3$.F | 11.00% |
| CC-3-V1 | 10.00% |
| CCH-35 | 5.00% |
| CC-5-V | 10.00% |
| GG-1-F | 12.00% |
| CCGU-3-F | 4.50% |
| CBC-33 | 0.50% |

Example M34

| | |
|---|---|
| CCH-35 | 5.00% |
| CC-3-V1 | 9.00% |
| CC-5-V | 6.00% |
| CCP-2OCF$_3$ | 5.00% |
| CCP-3OCF$_3$ | 8.00% |
| CCP-4OCF$_3$ | 6.00% |
| PGU-2-F | 8.00% |
| CCZU-3-F | 14.00% |
| CGZP-2-OT | 9.00% |
| CGZP-3-OT | 8.00% |
| GG-1-F | 14.00% |
| CBC-33 | 3.00% |
| BCH-32 | 5.00% |

Example M35

| | | | |
|---|---|---|---|
| CC-5-V | 4.00% | S → N [° C.]: | <-30 |
| CC-3-V1 | 11.00% | Clearing point [° C.]: | 77.0 |
| CCH-35 | 5.00% | Δn [589 nm, 20° C.]: | 0.0787 |
| CC-3-V | 17.00% | γ$_1$ [mPa · s, 20° C.]: | 58 |
| PU-1-F | 10.00% | V$_{10}$ [V]: | 1.78 |
| CCZU-2-F | 4.00% | | |
| CCZU-3-F | 15.00% | | |
| CCP-2OCF$_3$ | 3.00% | | |
| CCP-3OCF$_3$ | 8.00% | | |
| CCP-4OCF$_3$ | 6.00% | | |
| CGZP-2-OT | 7.00% | | |
| CGZP-3-OT | 2.00% | | |
| CCP-V-1 | 8.00% | | |

Example M36

| | | | |
|---|---|---|---|
| CCP-2F.F.F | 10.00% | Clearing point [° C.]: | 72.5 |
| CCP-2OCF$_3$ | 8.00% | Δn [589 nm, 20° C.]: | 0.0873 |
| CCP-3OCF$_3$ | 7.00% | γ$_1$ [mPa · s, 20° C.]: | 118 |
| CCP-4OCF$_3$ | 6.00% | V$_{10}$ [V]: | 1.08 |
| CCP-2OCF$_3$.F | 11.00% | | |
| CCH-3CF$_3$ | 1.00% | | |
| CCZU-2-F | 5.00% | | |
| CCZU-3-F | 15.00% | | |
| CCZU-5-F | 5.00% | | |
| CGZP-2-OT | 11.00% | | |
| CGZP-3-OT | 9.00% | | |
| PU-1-F | 12.00% | | |

Example M37

| | | | |
|---|---|---|---|
| CCH-35 | 4.00% | Clearing point [° C.]: | 78.0 |
| CC-3-V1 | 9.00% | Δn [589 nm, 20° C.]: | 0.1060 |
| CC-5-V | 3.50% | γ$_1$ [mPa · s, 20° C.]: | 87 |
| CCP-2OCF$_3$ | 7.00% | V$_{10}$ [V]: | 1.35 |
| CCP-3OCF$_3$ | 7.00% | | |
| CCP-4OCF$_3$ | 5.00% | | |
| PGU-2-F | 8.00% | | |
| PGU-3-F | 3.00% | | |
| CCZU-2-F | 3.50% | | |
| CCZU-3-F | 14.00% | | |
| CGZP-2-OT | 9.00% | | |
| CGZP-3-OT | 7.00% | | |
| PU-1-F | 12.00% | | |
| BCH-32 | 4.00% | | |
| CCP-V-1 | 4.00% | | |

-continued

Example M38

| | | | |
|---|---|---|---|
| CC-5-V | 4.00% | Clearing point [° C.]: | 79.0 |
| CC-3-V1 | 11.00% | $\Delta n$ [589 nm, 20° C.]: | 0.0777 |
| CCH-35 | 5.00% | $V_{10}$ [V]: | 1.79 |
| CC-3-V | 18.00% | | |
| GU-1-F | 10.00% | | |
| CCZU-2-F | 4.00% | | |
| CCZU-3-F | 15.00% | | |
| CCP-3OCF$_3$ | 8.00% | | |
| CCP-4OCF$_3$ | 8.00% | | |
| CGZP-2-OT | 7.50% | | |
| CBC-33 | 1.50% | | |
| CCP-V-1 | 8.00% | | |

Example M39

| | | | |
|---|---|---|---|
| CCP-2F.F.F | 10.00% | Clearing point [° C.]: | 75.5 |
| CCP-2OCF$_3$ | 8.00% | $\Delta n$ [589 nm, 20° C.]: | 0.0888 |
| CCP-3OCF$_3$ | 8.00% | $\gamma_1$ [mPa · s, 20° C.]: | 122 |
| CCP-4OCF$_3$ | 6.00% | $V_{10}$ [V]: | 1.03 |
| CCP-2OCF$_3$.F | 6.00% | | |
| CCGU-3-F | 1.00% | | |
| CCZU-2-F | 4.00% | | |
| CCZU-3-F | 15.00% | | |
| CCZU-5-F | 5.00% | | |
| CGZP-2-OT | 11.00% | | |
| CGZP-3-OT | 9.00% | | |
| GU-1-F | 14.00% | | |
| CCOC-3-3 | 1.00% | | |
| CCP-V-1 | 2.00% | | |

Example M40

| | | | |
|---|---|---|---|
| CC-5-V | 4.00% | S → N [° C.]: | <-20.0 |
| CC-3-V1 | 11.00% | Clearing point [° C.]: | +77.0 |
| CCH-35 | 4.00% | $\Delta n$ [589 nm, 20° C.]: | +0.0782 |
| CC-3-V | 19.00% | $\gamma_1$ [mPa · s, 20° C.]: | 59 |
| GG-1-F | 7.00% | $V_{10.0,20}$ [V]: | 1.79 |
| GU-1-F | 3.00% | | |
| CCZU-2-F | 4.00% | | |
| CCZU-3-F | 15.00% | | |
| CCP-3OCF$_3$ | 8.00% | | |
| CCP-4OCF$_3$ | 4.00% | | |
| CGZP-2-OT | 6.00% | | |
| CGZP-3-OT | 4.00% | | |
| CCP-V-1 | 11.00% | | |

Example M41

| | | | |
|---|---|---|---|
| CC-5-V | 5.00% | S → N [° C.]: | <-20.0 |
| CC-3-V1 | 10.00% | Clearing point [° C.]: | +77.0 |
| CCH-35 | 5.00% | $\Delta n$ [589 nm, 20° C.]: | +0.0779 |
| CC-3-V | 17.00% | $\gamma_1$ [mPa · s, 20° C.]: | 60 |
| GG-1-F | 8.00% | $V_{10.0,20}$ [V]: | 1.76 |
| GU-1-F | 2.00% | | |
| CCZU-2-F | 4.00% | | |
| CCZU-3-F | 15.00% | | |
| CCP-2OCF$_3$ | 4.00% | | |
| CCP-3OCF$_3$ | 8.00% | | |
| CCP-4OCF$_3$ | 5.00% | | |
| CGZP-2-OT | 6.50% | | |
| CGZP-3-OT | 2.50% | | |
| CCP-V-1 | 8.00% | | |

Example M42

| | | | |
|---|---|---|---|
| CC-3-V | 10.00% | S → N [° C.]: | <-30.0 |
| GG-1-F | 10.00% | Clearing point [° C.]: | +74.0 |
| PGU-2-F | 12.00% | $\Delta n$ [589 nm, 20° C.]: | +0.1511 |
| GPU-3-F | 12.00% | $\Delta \epsilon$ (1 kHz, 20° C.]: | +12.4 |
| PGU-5-F | 10.00% | $\gamma_1$ [mPa · s, 20° C.]: | 119 |
| CGZP-2-OT | 8.00% | | |
| CGZP-3-OT | 8.00% | | |
| BCH-3F.F.F | 4.00% | | |
| PGIGI-3-F | 5.00% | | |
| BCH-32 | 6.00% | | |
| CP-V-1 | 11.00% | | |
| CBC-33 | 2.00% | | |
| CBC-53 | 2.00% | | |

Example M43

| | | | |
|---|---|---|---|
| CC-5-V | 2.00% | S → N [° C.]: | <-20.0 |
| CC-3-V1 | 12.00% | Clearing point [° C.]: | +76.0 |
| CCH-35 | 5.00% | $\Delta n$ [589 nm, 20° C.]: | +0.0796 |
| CC-3-V | 19.00% | $V_{10.0,20}$ [V]: | 1.79 |
| GG-1-F | 8.00% | | |
| GU-1-F | 3.00% | | |
| CCZU-2-F | 2.00% | | |
| CCZU-3-F | 15.00% | | |
| CCP-3OCF$_3$ | 8.00% | | |
| CCP-4OCF$_3$ | 4.00% | | |
| CGZP-2-OT | 6.00% | | |
| CGZP-3-OT | 4.00% | | |
| CCP-V-1 | 12.00% | | |

Example M44

| | | | |
|---|---|---|---|
| CC-3-V | 10.00% | Clearing point [° C.]: | +74.0 |
| GU-1-F | 11.00% | $\Delta n$ [589 nm, 20° C.]: | +0.1501 |
| PGU-2-F | 12.00% | | |
| PGU-3-F | 12.00% | | |
| PGU-5-F | 10.00% | | |
| CGZP-2-OT | 8.00% | | |
| CGZP-3-OT | 7.00% | | |
| PGIGI-3-F | 6.00% | | |
| BCH-32 | 6.00% | | |
| CCP-V-1 | 13.00% | | |
| CBC-33 | 3.00% | | |
| CBC-53 | 2.00% | | |

Example M45

| | | | |
|---|---|---|---|
| CC-3-V | 11.00% | Clearing point [° C.]: | +75.0 |
| GU-1-F | 8.00% | $\Delta n$ [589 nm, 20° C.]: | +0.1508 |
| PGU-2-F | 12.00% | | |
| PGU-3-F | 12.00% | | |
| PGU-5-F | 10.00% | | |
| CGZP-2-OT | 8.00% | | |
| CGZP-3-OT | 8.00% | | |
| BCH-3F.F.F | 4.00% | | |
| PGIGI-3-F | 6.00% | | |
| BCH-32 | 6.00% | | |
| CCP-V-1 | 12.00% | | |
| CBC-33 | 3.00% | | |

Example M46

| | | | |
|---|---|---|---|
| CC-3-V | 12.00% | Clearing point [° C.]: | +74.0 |
| GU-1-F | 6.00% | $\Delta n$ [589 nm, 20° C.]: | +0.1494 |
| PGU-2-F | 12.00% | | |
| PGU-3-F | 12.00% | | |
| PGU-5-F | 10.00% | | |
| CGZP-2-OT | 8.00% | | |
| CGZP-3-OT | 8.00% | | |
| BCH-3F.F.F | 7.00% | | |
| PGIGI-3-F | 6.00% | | |
| BCH-32 | 5.00% | | |
| CCP-V-1 | 12.00% | | |
| CBC-33 | 2.00% | | |

Example M47

| | | | |
|---|---|---|---|
| CC-5-V | 4.00% | S → N [° C.]: | <-40.0 |
| CC-3-V1 | 11.00% | Clearing point [° C.]: | +77.0 |
| CCH-35 | 5.00% | $\Delta n$ [589 nm, 20° C.]: | +0.0788 |
| CCH-3-V | 17.00% | $\gamma_1$ [mPa · s, 20° C.]: | 59 |
| PU-1-F | 7.00% | $V_{10}$ [V]: | 1.67 |
| GU-1-F | 3.00% | | |
| CCZU-2-F | 4.00% | | |
| CCZU-3-F | 15.00% | | |
| CCP-2OCF$_3$ | 3.00% | | |
| CCP-3OCF$_3$ | 8.00% | | |
| CCP-4OCF$_3$ | 6.00% | | |
| CGZP-2-OT | 6.50% | | |
| CGZP-3-OT | 2.50% | | |
| CCP-V-1 | 8.00% | | |

Example M48

| | | | |
|---|---|---|---|
| CCP-1F.F.F | 6.00% | S → N [° C.]: | <-40.0 |
| CCP-2F.F.F | 9.00% | Clearing point [° C.]: | +79.5 |
| CCP-2OCF$_3$ | 7.00% | $\Delta n$ [589 nm, 20° C.]: | +0.0878 |
| CCP-3OCF$_3$ | 7.00% | $\gamma_1$ [mPa · s, 20° C.]: | 148 |

Example M49 (continued)

| Compound | % |
|---|---|
| CCP-4OCF₃ | 4.00% |
| CCP-2OCF₃.F | 11.00% |
| CCGU-3-F | 5.00% |
| CCZU-2-F | 4.00% |
| CCZU-3-F | 15.00% |
| CCZU-5-F | 4.00% |
| CGZP-2-OT | 10.00% |
| CGZP-3-OT | 8.00% |
| GU-1-F | 4.00% |
| GU-2-F | 2.00% |
| UU-1-F | 4.00% |

$V_{10}$ [V]: 1.00

Example M50

| Compound | % |
|---|---|
| CCP-2OCF₃ | 8.00% |
| CCP-3OCF₃ | 8.00% |
| CCZU-2-F | 4.00% |
| CCZU-3-F | 15.00% |
| CCZU-5-F | 4.00% |
| CCP-V-1 | 14.00% |
| CDU-2-F | 9.00% |
| PGU-2-F | 1.00% |
| GU-1-F | 7.00% |
| PUQU-2-F | 4.00% |
| PUQU-3-F | 4.50% |
| CC-3-V1 | 11.00% |
| CC-5-V | 5.50% |
| CCH-35 | 5.00% |

Example M51

| Compound | % |
|---|---|
| CCP-2OCF₃ | 8.00% |
| CCP-3OCF₃ | 8.00% |
| CCZU-2-F | 4.00% |
| CCZU-3-F | 15.00% |
| CCZU-5-F | 4.00% |
| CDU-2-F | 9.00% |
| CDU-3-F | 2.50% |
| GU-1-F | 7.00% |
| PUQU-2-F | 4.00% |
| PUQU-3-F | 4.00% |
| CCP-V-1 | 14.00% |
| CC-3-V1 | 10.50% |
| CC-3-V | 10.00% |

Example M52

| Compound | % |
|---|---|
| CCP-2OCF₃ | 8.00% |
| CCP-3OCF₃ | 8.00% |
| CCZU-2-F | 4.00% |
| CCZU-3-F | 15.00% |
| CCZU-5-F | 4.00% |
| CDU-2-F | 9.00% |
| CDU-3-F | 3.50% |
| PGU-2-F | 1.00% |
| GU-1-F | 6.00% |
| PUQU-2-F | 4.00% |
| PUQU-3-F | 5.00% |
| CCP-V-1 | 14.00% |
| CC-3-V1 | 11.00% |
| CC-3-V | 7.50% |

Clearing point [° C.]: +79.0  
Δn [589 nm, 20° C.]: +0.0851  
Δε [kHz, 20° C.]: 10.3  
$\gamma_1$ [mPa · s, 20° C.]: 85

Example M53

| Compound | % |
|---|---|
| CCP-2F.F.F | 9.50% |
| CCP-2OCF₃ | 7.00% |
| CGZP-2-OT | 10.00% |
| CGZP-3-OT | 6.00% |
| CCZU-2-F | 4.00% |
| CCZU-3-F | 10.50% |
| PUQU-2-F | 4.00% |
| PUQU-3-F | 5.00% |
| CDU-2-F | 7.00% |
| PGU-2-F | 5.00% |
| GU-1-F | 5.00% |
| CCP-V-1 | 9.50% |
| CC-3-V1 | 10.50% |
| CC-5-V | 2.00% |
| CCH-35 | 5.00% |

(continued)

| Compound | % |
|---|---|
| CCP-2F.F.F | 9.50% |
| CCP-3OCF₃ | 8.00% |
| CGZP-2-OT | 9.00% |
| CGZP-3-OT | 7.00% |
| CCZU-2-F | 4.00% |
| CCZU-3-F | 10.50% |
| PUQU-2-F | 4.00% |
| PUQU-3-F | 5.00% |
| CDU-2-F | 6.00% |
| PGU-2-F | 6.00% |
| GU-1-F | 5.00% |
| CCP-V-1 | 8.00% |
| CC-3-V1 | 9.00% |
| CC-3-V | 9.00% |

Example M54

| Compound | % |
|---|---|
| CCP-2OCF₃ | 5.00% |
| CCP-3OCF₃ | 8.00% |
| CDU-2-F | 7.00% |
| PGU-2-F | 6.50% |
| CGZP-2-OT | 10.00% |
| CGZP-3-OT | 5.00% |
| CCZU-2-F | 4.00% |
| CCZU-3-F | 13.00% |
| PUQU-2-F | 4.00% |
| PUZU-3-F | 5.00% |
| CCP-V-1 | 4.50% |
| CC-3-V1 | 10.00% |
| CC-5-V | 8.00% |
| CCH-35 | 5.00% |
| GU-1-F | 5.00% |

Example M55

| Compound | % |
|---|---|
| CCP-3OCF₃ | 7.50% |
| CGZP-2-OT | 10.00% |
| CGZP-3-OT | 4.00% |
| CCZU-2-F | 4.00% |
| CCZU-3-F | 12.50% |
| PUQU-2-F | 4.00% |
| PUQU-3-F | 4.00% |
| PZU-V2-F | 5.00% |
| GU-1-F | 5.00% |
| CDU-2-F | 8.50% |
| CDU-3-F | 3.50% |
| PUGU-2-F | 2.50% |
| CCP-V-1 | 15.50% |
| CC-3-V1 | 11.00% |
| CCH-35 | 3.00% |

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A nematic liquid-crystalline medium based on a mixture of polar compounds of positive or negative dielectric anisotropy, said medium comprising at least two components wherein one of said components is one or more compounds of formula I

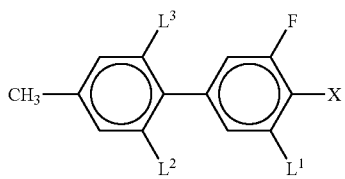

wherein
- X is F, Cl, NCS, or a halogenated alkyl radical having up to 8 carbon atoms, in which one or more $CH_2$ groups may, in each case independently, be replaced by —O— or —CH=CH— in such a way that O atoms are not linked directly to one another, and
- $L^1$, $L^2$ and $L^3$ are each, independently of one another, H or F.

2. A liquid-crystalline medium according to claim 1, wherein X is F, Cl, NCS, $CF_3$, $CF_2H$, $CF_2CF_3$, $CF_2CF_2CF_3$, $CH_2CH_2CF_3$, $CF_2CH_2CF_3$, $OCF_3$, $OCF_2H$, $OCFHCF_3$, $OCFHCFH_2$, $OCFHCF_2H$, $OCF_2CH_3$, $OCF_2CFH_2$, $OCF_2CF_2H$, $OCF_2CF_2CF_3$, $OCF_2CF_2CFH_2$, $OCFHCF_2CF_3$, $OCFHCF_2CF_2H$, $OCF_2CF_2CF_3$, $OCF_2CHFCF_3$, or $OCClFCF_2CF_3$.

3. A liquid-crystalline medium according to claim 1, wherein said one or more compounds is least one compound from formulae I1 to I5

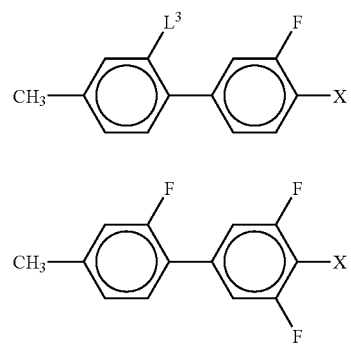

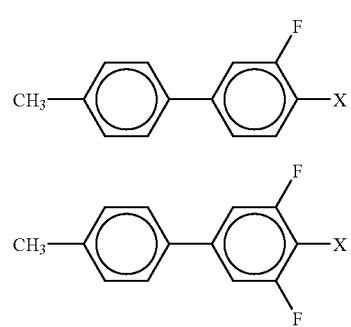

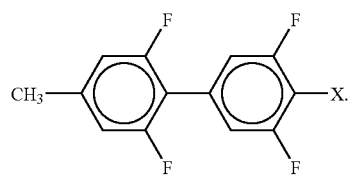

4. A liquid-crystalline medium according to claim 2, wherein said one or more compounds is least one compound from formulae I1 to I5

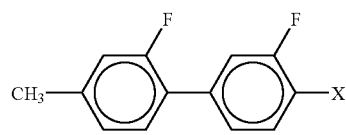

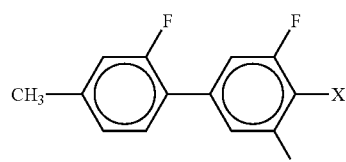

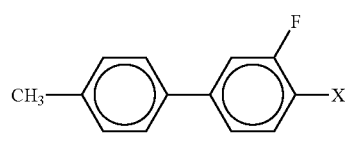

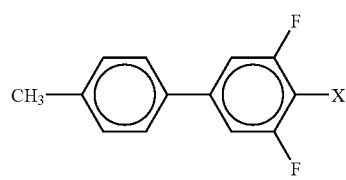

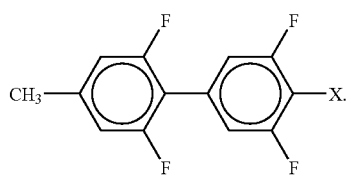

5. A liquid-crystalline medium according to claim 1, further comprising one or more compounds selected from the group consisting of formulae II, III, IV, V, VI, VII, VIII, IX and X:

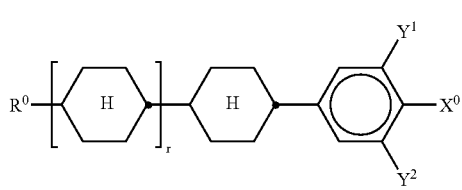

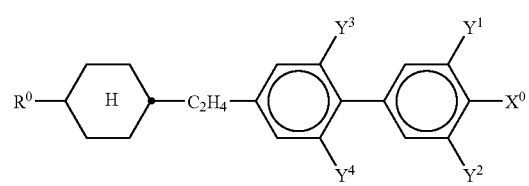

-continued

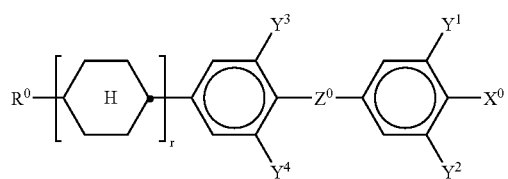
IV

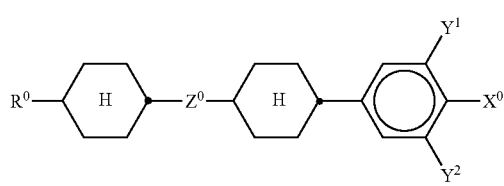
V

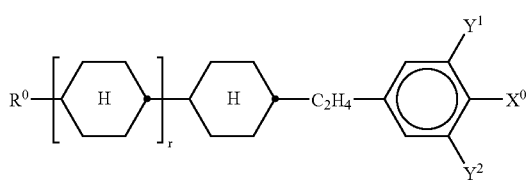
VI

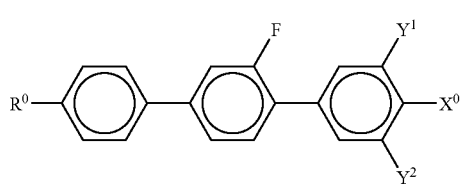
VII

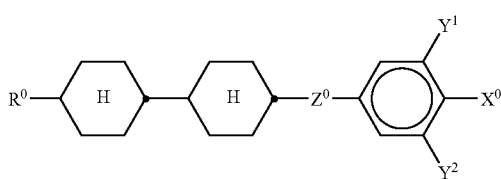
VIII

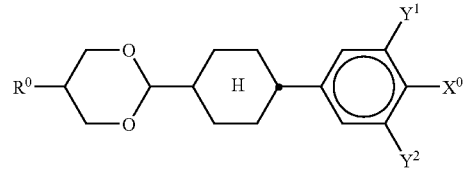
IX

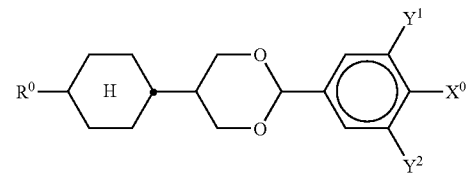
X wherein
- R⁰ is n-alkyl, oxaalkyl, fluoroalkyl, alkenyloxy or alkenyl, each having from 2 to 12 carbon atoms,
- X⁰ is F, Cl, halogenated alkyl, halogenated alkenyl, halogenated alkenyloxy or halogenated alkoxy, each having up to 8 carbon atoms,
- Z⁰ is —CH=CH—, —CH₂O—, —OCH₂—, —(CH₂)₄—, —C₂H₄—, —C₂F₄—, —CF=CF—, —CF₂O—, —OCF₂— or —COO—, Y¹, Y²,
Y³ and Y⁴ are each, independently of one another, H or F, and
r is 0 or 1.

6. A liquid-crystalline medium according to claim 2, further comprising one or more compounds selected from the group consisting of formulae II, III, IV, V, VI, VII, VIII, IX and X:

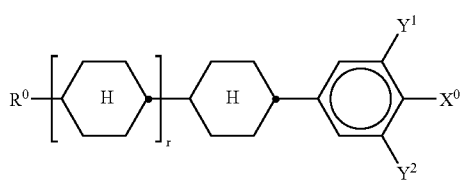
II

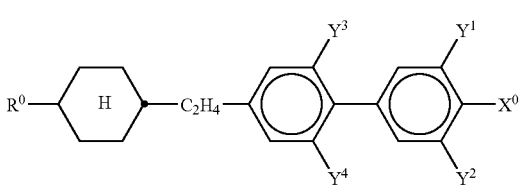
III

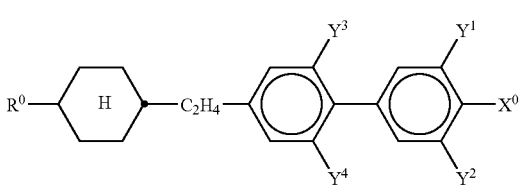
IV

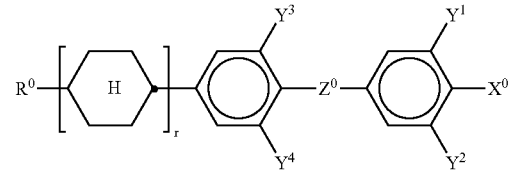
V

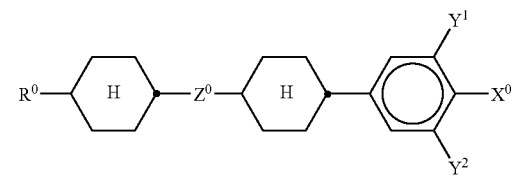
VI

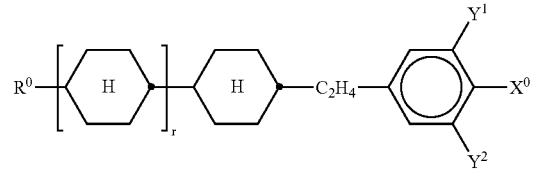
VII

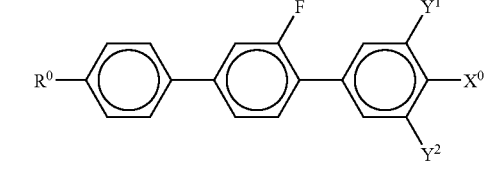
VIII

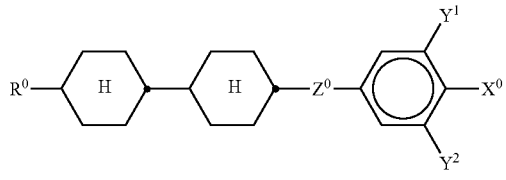

-continued

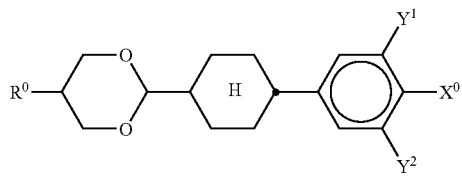
IX

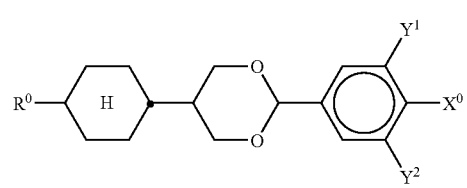
X wherein
- R⁰ is n-alkyl, oxaalkyl, fluoroalkyl, alkenyloxy or alkenyl, each having from 2 to 12 carbon atoms,
- X⁰ is F, Cl, halogenated alkyl, halogenated alkenyl, halogenated alkenyloxy or halogenated alkoxy, each having up to 8 carbon atoms,
- Z⁰ is —CH=CH—, —CH₂O—, —OCH₂—, —(CH₂)₄—, —C₂H₄—, —C₂F₄—, —CF=CF—, —CF₂O—, —OCF₂— or —COO—,
- Y¹, Y²,
- Y³ and Y⁴ are each, independently of one another, H or F, and
- r is 0 or 1.

7. A liquid-crystalline medium according to claim 3, further comprising one or more compounds selected from the group consisting of formulae II, III, IV, V, VI, VII, VIII, IX and X:

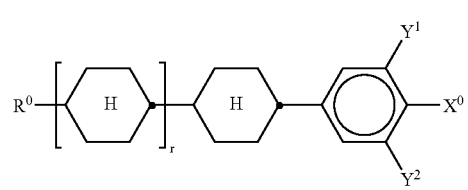
II

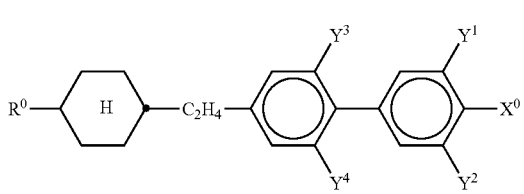
III

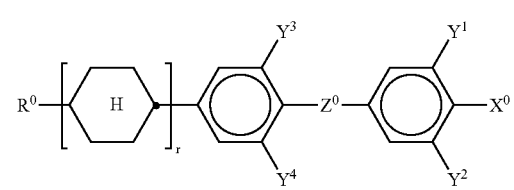
IV

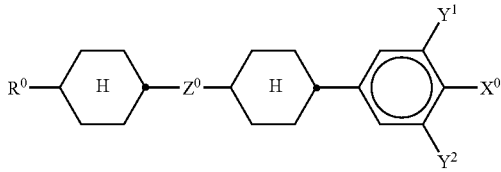
V

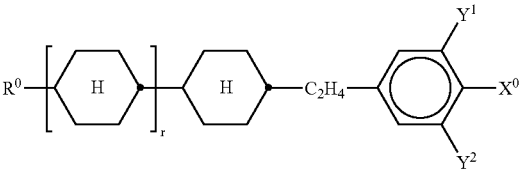
VI

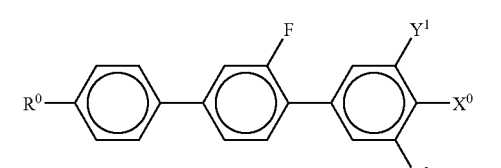
VII

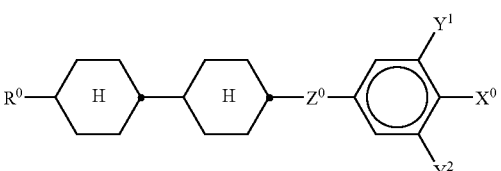
VIII

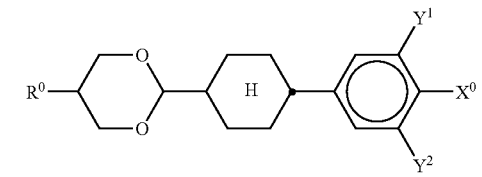
IX

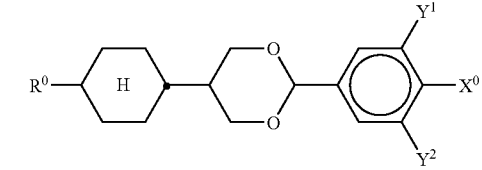
X wherein
- R⁰ is n-alkyl, oxaalkyl, fluoroalkyl, alkenyloxy or alkenyl, each having from 2 to 12 carbon atoms,
- X⁰ is F, Cl, halogenated alkyl, halogenated alkenyl, halogenated alkenyloxy or halogenated alkoxy, each having up to 8 carbon atoms,
- Z⁰ is —CH=CH—, —CH₂O—, —OCH₂—, —(CH₂)₄—, —C₂H₄—, —C₂F₄—, —CF=CF—, —CF₂O—, —OCF₂— or —COO—,
- Y¹, Y²,
- Y³ and Y⁴ are each, independently of one another, H or F, and
- r is 0 or 1.

8. A liquid-crystalline medium according to claim 4, further comprising one or more compounds selected from the group consisting of formulae II, III, IV, V, VI, VII, VIII, IX and X:

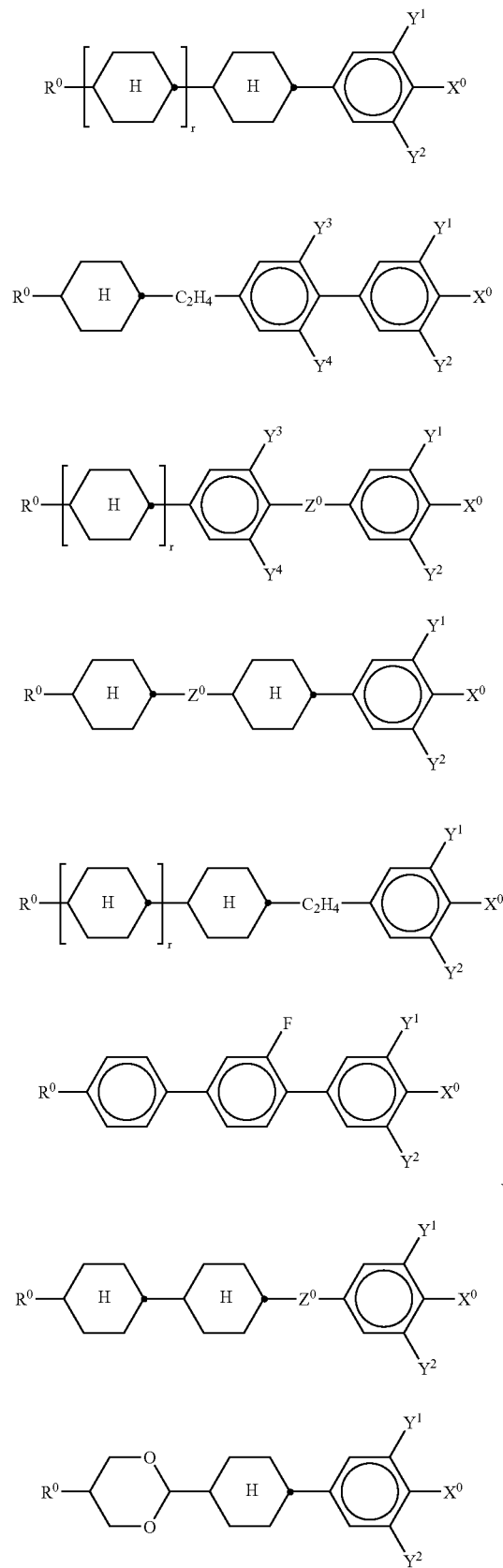

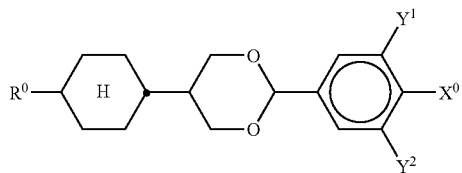

wherein

R⁰ is n-alkyl, oxaalkyl, fluoroalkyl, alkenyloxy or alkenyl, each having from 2 to 12 carbon atoms, X⁰ is F, Cl, halogenated alkyl, halogenated alkenyl, halogenated alkenyloxy or halogenated alkoxy, each having up to 8 carbon atoms, Z⁰ is —CH=CH—, —CH₂O—, —OCH₂—, —(CH₂)₄—, —C₂H₄—, —C₂F₄—, —CF=CF—, —CF₂O—, —OCF₂— or —COO—,

Y¹, Y²,

Y³ and Y⁴ are each, independently of one another, H or F, and r is 0 or 1.

9. A medium according to claim 5, wherein the proportion of compounds of the formulae I to X in the mixture as a whole is at least 50% by weight.

10. A medium according to claim 1, further comprising one or more compounds of formulae RI to RXV

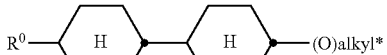

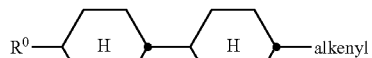

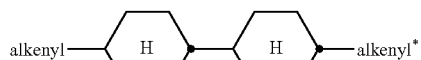

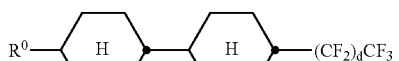

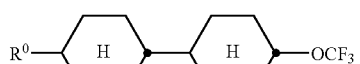

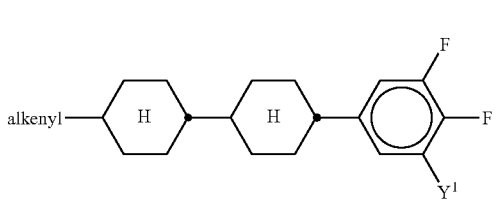

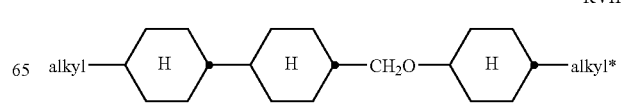

-continued

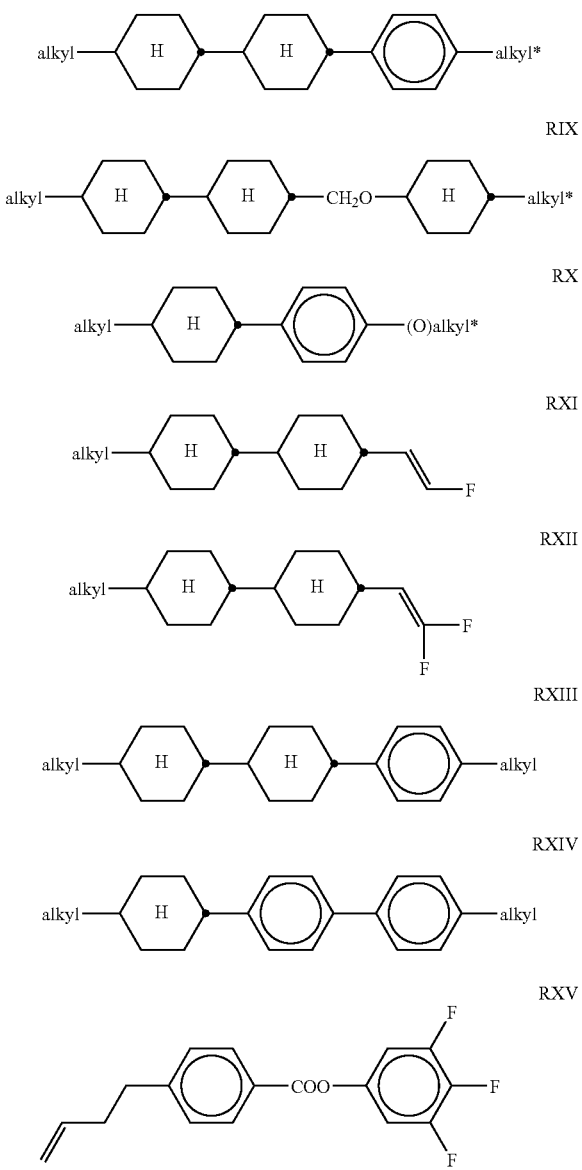

wherein
R⁰ is n-alkyl, oxaalkyl, fluoroalkyl, alkenyloxy or alkenyl, each having from 2 to 12 carbon atoms,
d is 0, 1 or 2,
$Y^1$ is H or F,
alkyl and
alkyl* are each, independently of one another, a straight-chain or branched alkyl radical having from 2 to 8 carbon atoms, and
alkenyl and
alkenyl* are each, independently of one another, a straight-chain or branched alkenyl radical having from 2 to 8 carbon atoms.

11. A medium according to claim 5, wherein $X^0$ is F, $OCHF_2$ or $OCF_3$, and $Y^2$ is H or F.

12. A fluorinated biphenyl of formula I

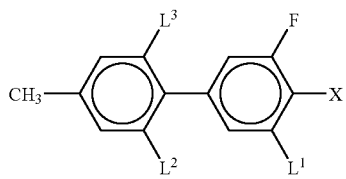

wherein
X is F, Cl, NCS, or a halogenated alkyl radical having up to 8 carbon atoms, in which one or more $CH_2$ groups may, in each case independently, be replaced by —O— or —CH=CH— in such a way that O atoms are not linked directly to one another, and
$L^1$, $L^2$ and $L^3$ are each, independently of one another, H or F,
wherein said compound is not

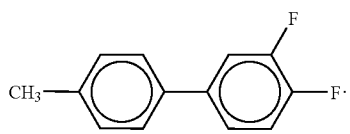

13. A fluorinated biphenyl of formulae I1, I2, I4 to I5

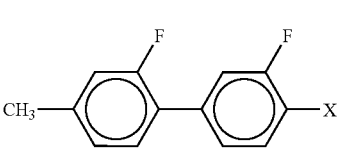

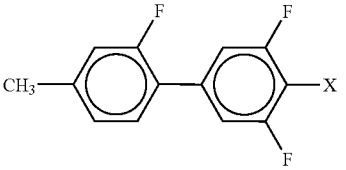

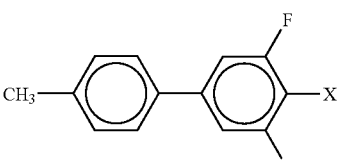

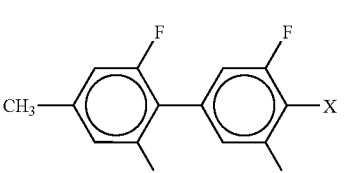

wherein
X is F, Cl, NCS, or a halogenated alkyl radical having up to 8 carbon atoms, in which one or more $CH_2$ groups may, in each case independently, be replaced by —O— or —CH=CH— in such a way that O atoms are not linked directly to one another.

14. A fluorinated biphenyl according to claim 13, wherein X is F or OCF$_3$.

15. In an electro-optical liquid-crystal display containing a liquid-crystalline medium, the improvement wherein said medium is according to claim 1.

16. In a method of generating an electro-optical effect using a liquid crystal display, the improvement wherein said display is according to claim 15.

17. A liquid-crystalline medium based on a mixture of polar compounds of positive or negative dielectric anisotropy, said medium comprising at least two components wherein one of said components is one or more compounds of formula I

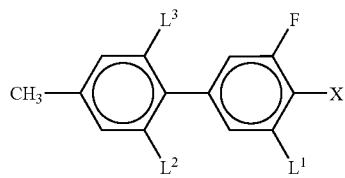

wherein
- X is F, Cl, CN, SF$_5$, NCS, or a halogenated alkyl radical having up to 8 carbon atoms, in which one or more CH$_2$ groups may, in each case independently, be replaced by —O— or —CH=CH— in such a way that O atoms are not linked directly to one another, and
- L$^1$, L$^2$ and L$^3$ are each, independently of one another, H or F, and
- said medium further comprising one or more compounds selected from the group consisting of formulae II, III, IV, V, VI, VII, VIII, IX and X:

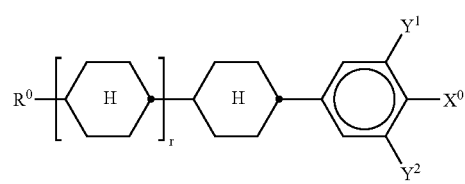

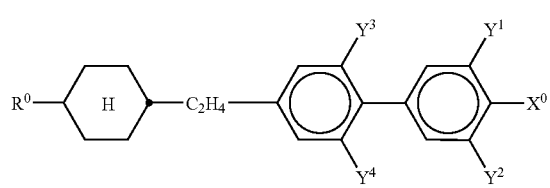

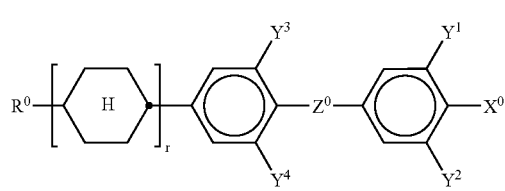

-continued

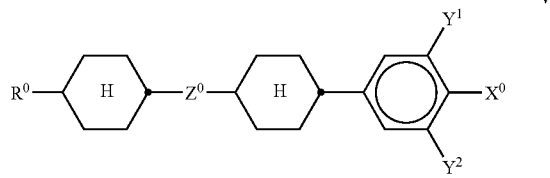

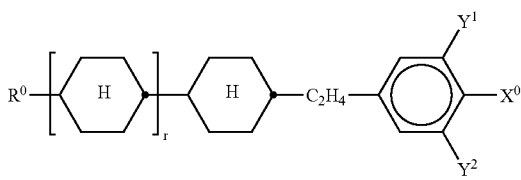

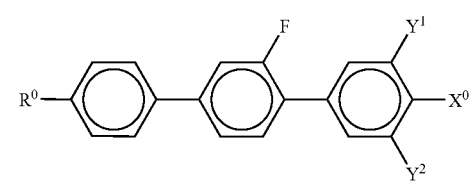

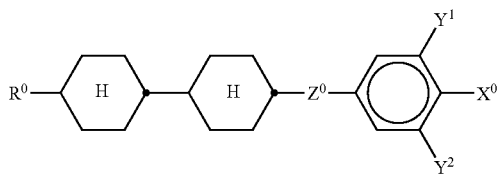

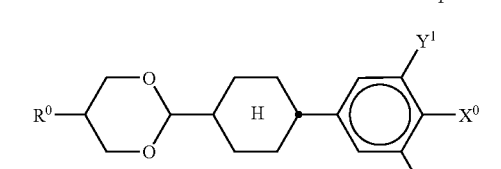

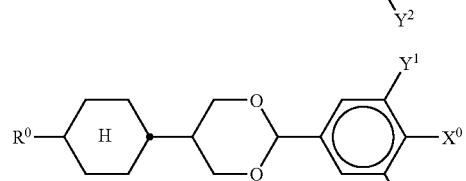

wherein
- R$^0$ is n-alkyl, oxaalkyl, fluoroalkyl, alkenyloxy or alkenyl, each having from 2 to 12 carbon atoms,
- X$^0$ is F, Cl, halogenated alkyl, halogenated alkenyl, halogenated alkenyloxy or halogenated alkoxy, each having up to 8 carbon atoms,
- Z$^0$ is —CH=CH—, —CH$_2$O—, —OCH$_2$—, —(CH$_2$)$_4$—, —C$_2$H$_4$—, —C$_2$F$_4$—, —CF=CF—, —CF$_2$O—, —OCF$_2$— or —COO—,
- Y$^1$, Y$^2$, Y$^3$ and Y$^4$ are each, independently of one another, H or F, and
- r is 0 or 1.

18. A liquid-crystalline medium according to claim 17, wherein X is F, Cl, CN, NCS, CF$_3$, SF$_5$, CF$_2$H, CF$_2$CF$_3$, CF$_2$CF$_2$CF$_3$, CH$_2$CH$_2$CF$_3$, CF$_2$CH$_2$CF$_3$, OCF$_3$, OCF$_2$H, OCFHCF$_3$, OCFHCFH$_2$, OCFHCF$_2$H, OCF$_2$CH$_3$, OCF$_2$CFH$_2$, OCF$_2$CF$_2$H, OCF$_2$CF$_2$CF$_2$H, OCF$_2$CF$_2$CFH$_2$, OCFHCF$_2$CF$_3$, OCFHCF$_2$CF$_2$H, OCF$_2$CF$_2$CF$_3$, OCF$_2$CHFCF$_3$, or OCClFCF$_2$CF$_3$.

19. A liquid-crystalline medium according to claim 17, wherein said one or more compounds is least one compound from formulae I1 to I5

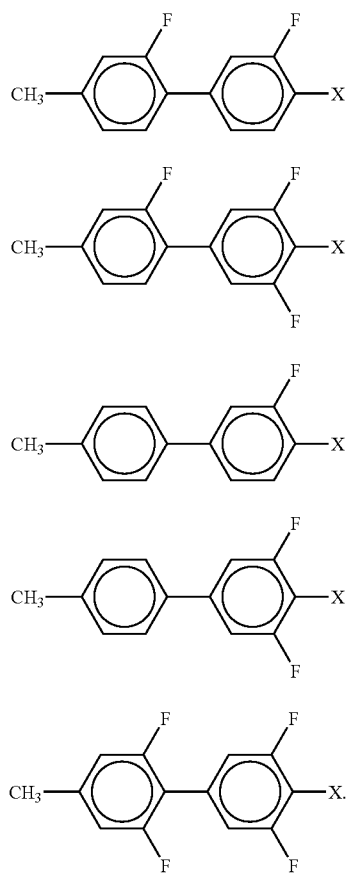

20. A liquid-crystalline medium according to claim 18, wherein said one or more compounds is least one compound from formulae I1 to I5

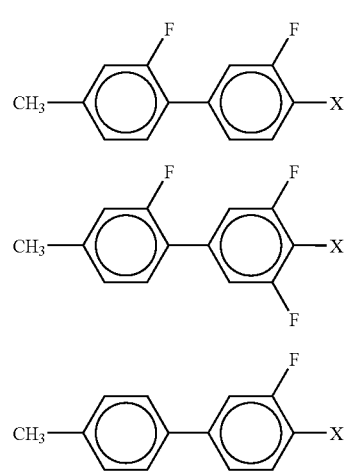

-continued

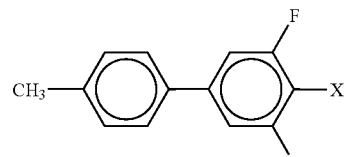

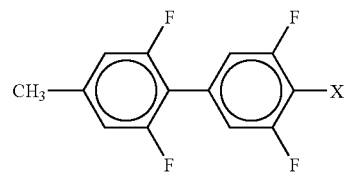

21. A medium according to claim 17, wherein the proportion of compounds of the formulae I to X in the mixture as a whole is at least 50% by weight.

22. A medium according to claim 17, wherein $X^0$ is F, OCHF$_2$ or OCF$_3$, and $Y^2$ is H or F.

23. A fluorinated biphenyl of formula I3

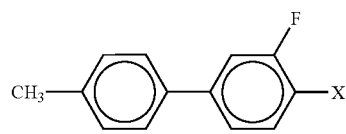

wherein
X is Cl, NCS, or a halogenated alkyl radical having up to 8 carbon atoms, in which one or more CH$_2$ groups may, in each case independently, be replaced by —O— or —CH=CH— in such a way that O atoms are not linked directly to one another.

24. A fluorinated biphenyl according to claim 23, wherein X is OCF$_3$.

25. A nematic liquid-crystalline medium based on a mixture of polar compounds of positive or negative dielectric anisotropy, said medium comprising at least two components wherein one of said components is one or more compounds of formula I

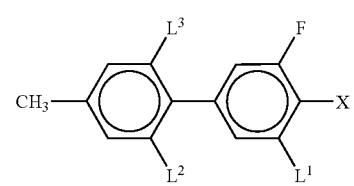

wherein
X is F, Cl, SF$_5$, NCS, or a halogenated alkyl radical having up to 8 carbon atoms, in which one or more CH$_2$ groups may, in each case independently, be replaced by —O— or —CH=CH— in such a way that O atoms are not linked directly to one another, and
L$^1$, L$^2$ and L$^3$ are each, independently of one another, H or F,
wherein said medium has a nematic phase down to −20° C. and a clearing point above 80° C.

26. A liquid-crystalline medium according to claim 25, wherein said medium has a nematic phase down to −30° C. and a clearing point above 90° C.

27. A liquid-crystalline medium according to claim 25, wherein said medium has a nematic phase down to −40° C. and a clearing point above 100° C.

28. A nematic liquid-crystalline medium based on a mixture of polar compounds of positive or negative dielectric anisotropy, said medium comprising at least two components wherein one of said components is one or more compounds of formula I

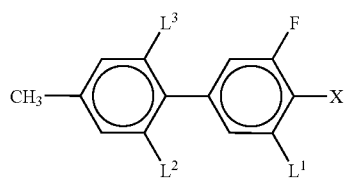

I wherein
  X is F, Cl, SF$_5$, NCS, or a halogenated alkyl radical having up to 8 carbon atoms, in which one or more CH$_2$ groups may, in each case independently, be replaced by —O— or —CH=CH— in such a way that O atoms are not linked directly to one another, and
  L$^1$, L$^2$ and L$^3$ are each, independently of one another, H or F,
    wherein said medium has a dielectric anisotropy value $\Delta\epsilon$ of $\geq 4$.

29. A liquid-crystalline medium according to claim 28, wherein said medium has a dielectric anisotropy value $\Delta\epsilon$ of $\geq 6$.

30. A nematic liquid-crystalline medium based on a mixture of polar compounds of positive or negative dielectric anisotropy, said medium comprising at least two components wherein one of said components is one or more compounds of formula I

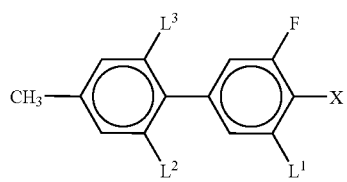

I wherein
  X is F, Cl, CN, SF$_5$, NCS, or a halogenated alkyl radical having up to 8 carbon atoms, in which one or more CH$_2$ groups may, in each case independently, be replaced by —O— or —CH=CH— in such a way that O atoms are not linked directly to one another, and
  L$^1$, L$^2$ and L$^3$ are each, independently of one another, H or F, and
wherein said medium has a TN threshold of below 1.5 V.

31. A liquid-crystalline medium according to claim 30, wherein said medium has a TN threshold of below 1.3 V.

32. A nematic liquid-crystalline medium based on a mixture of polar compounds of positive or negative dielectric anisotropy, said medium comprising at least two components wherein one of said components is one or more compounds of formula I

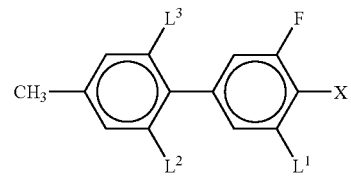

I wherein
  X is F, Cl, CN, SF$_5$, NCS, or a halogenated alkyl radical having up to 8 carbon atoms, in which one or more CH$_2$ groups may, in each case independently, be replaced by —O— or —CH=CH— in such a way that O atoms are not linked directly to one another, and
  L$^1$, L$^2$ and L$^3$ are each, independently of one another, H or F, and
  wherein said medium has a flow viscosity $v_{20}$ at 20° C. of $<60$ mm$^2 \cdot$s$^{-1}$.

33. A liquid-crystalline medium according to claim 32, wherein said medium has a flow viscosity $v_{20}$ at 20° C. of $<50$ mm$^2 \cdot$s$^{-1}$.

34. A nematic liquid-crystalline medium based on a mixture of polar compounds of positive or negative dielectric anisotropy, said medium comprising at least two components wherein one of said components is one or more compounds of formula I

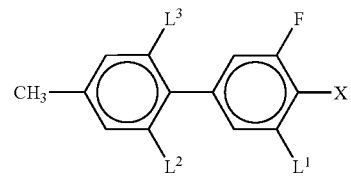

I wherein
  X is F, Cl, SF$_5$, NCS, or a halogenated alkyl radical having up to 8 carbon atoms, in which one or more CH$_2$ groups may, in each case independently, be replaced by —O— or —CH=CH— in such a way that O atoms are not linked directly to one another, and
  L$^1$, L$^2$ and L$^3$ are each, independently of one another, H or F,
    wherein said medium has a nematic phase range of at least 90.

35. A nematic liquid-crystalline medium based on a mixture of polar compounds of positive or negative dielectric anisotropy, said medium comprising at least two components wherein one of said components is one or more compounds of formula I

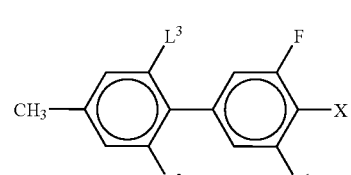

I wherein
X is F, Cl, SF$_5$, NCS, or a halogenated alkyl radical having up to 8 carbon atoms, in which one or more CH$_2$ groups may, in each case independently, be replaced by —O— or —CH=CH— in such a way that O atoms are not linked directly to one another, and L$^1$, L$^2$ and L$^3$ are each, independently of one another, H or F,
wherein the amount of compounds of formula I in said medium is 5–95 wt %.

36. A liquid-crystalline medium according to claim 35, wherein the amount of compounds of formula I in said medium is 5–50%.

37. A liquid-crystalline medium according to claim 35, wherein the amount of compounds of formula I in said medium is 15–40%.

38. A liquid-crystalline medium based on a mixture of polar compounds of positive or negative dielectric anisotropy, said medium comprising at least two components wherein one of said components is one or more compounds of formula I

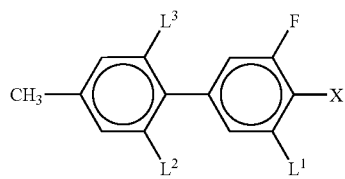

I wherein
X is F, Cl, NCS, or a halogenated alkyl radical having up to 8 carbon atoms, in which one or more CH$_2$ groups may, in each case independently, be replaced by —O— or —CH=CH— in such a way that O atoms are not linked directly to one another, and L$^1$, L$^2$ and L$^3$ are each, independently of one another, H or F, wherein at least one of L$^1$, L$^2$ and L$^3$ is F.

39. A liquid-crystalline medium according to claim 17, wherein X is F, Cl, SF$_5$, NCS, or a halogenated alkyl radical having up to 8 carbon atoms, in which one or more CH$_2$ groups may, in each case independently, be replaced by —O— or —CH=CH— in such a way that O atoms are not linked directly to one another.

40. A liquid-crystalline medium according to claim 18, wherein X is F, Cl, NCS, CF$_3$, SF$_5$, CF$_2$H, CF$_2$CF$_3$, CF$_2$CF$_2$CF$_3$, CH$_2$CH$_2$CF$_3$, CF$_2$CH$_2$CF$_3$, OCF$_3$, OCF$_2$H, OCFHCF$_3$, OCFHCFH$_2$, OCFHCF$_2$H, OCF$_2$CH$_3$, OCF$_2$CFH$_2$, OCF$_2$CF$_2$H, OCF$_2$CF$_2$CF$_2$H, OCF$_2$CF$_2$CFH$_2$, OCFHCF$_2$CF$_3$, OCFHCF$_2$CF$_2$H, OCF$_2$CF$_2$CF$_3$, OCF$_2$CHFCF$_3$, or OCClFCF$_2$CF$_3$.

41. A liquid-crystalline medium according to claim 19, wherein X is F, Cl, SF$_5$, NCS, or a halogenated alkyl radical having up to 8 carbon atoms, in which one or more CH$_2$ groups may, in each case independently, be replaced by —O— or —CH=CH— in such a way that O atoms are not linked directly to one another.

42. A liquid-crystalline medium according to claim 20, wherein X is F, Cl, NCS, CF$_3$, SF$_5$, CF$_2$H, CF$_2$CF$_3$, CF$_2$CF$_2$CF$_3$, CH$_2$CH$_2$CF$_3$, CF$_2$CH$_2$CF$_3$, OCF$_3$, OCF$_2$H, OCFHCF$_3$, OCFHCFH$_2$, OCFHCF$_2$H, OCF$_2$CH$_3$, OCF$_2$CFH$_2$, OCF$_2$CF$_2$H, OCF$_2$CF$_2$CF$_2$H, OCF$_2$CF$_2$CFH$_2$, OCFHCF$_2$CF$_3$, OCFHCF$_2$CF$_2$H, OCF$_2$CF$_2$CF$_3$, OCF$_2$CHFCF$_3$, or OCClFCF$_2$CF$_3$.

43. A medium according to claim 39, wherein the proportion of compounds of the formulae I to X in the mixture as a whole is at least 50% by weight.

44. A medium according to claim 39, wherein X$^0$ is F, OCHF$_2$ or OCF$_3$, and Y$^2$ is H or F.

45. A liquid-crystalline medium based on a mixture of polar compounds of positive or negative dielectric anisotropy, said medium comprising at least two components wherein one of said components is one or more compounds of formula I

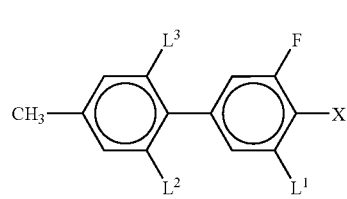

I wherein
X is F, Cl, CN, SF$_5$, NCS, or a halogenated alkyl radical having up to 8 carbon atoms, in which one or more CH$_2$ groups may, in each case independently, be replaced by —O— or —CH=CH— in such a way that O atoms are not linked directly to one another, and L$^1$, L$^2$ and L$^3$ are each, independently of one another, H or F, and
said medium further comprising one or more compounds of formulae RI to RXV

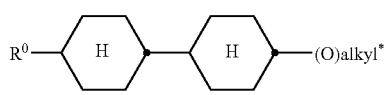

RXVI

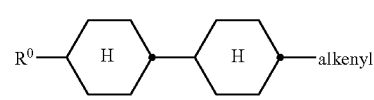

RXVII

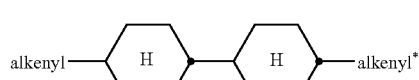

RXVIII

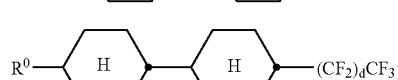

RXIX

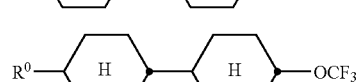

RXX

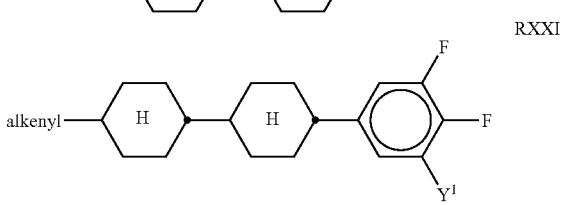

RXXI

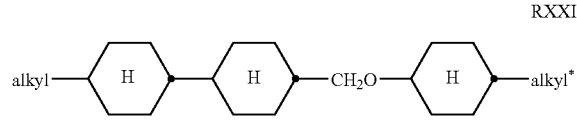

RXXII

-continued

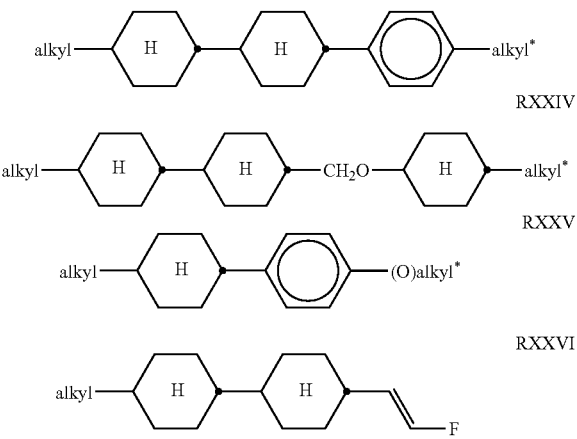

RXXIII

RXXIV

RXXV

RXXVI wherein
R⁰ is n-alkyl, oxaalkyl, fluoroalkyl, alkenyloxy or alkenyl, each having from 2 to 12 carbon atoms,
d is 0, 1 or 2,
$Y^1$ is H or F,
alkyl and
alkyl* are each, independently of one another, a straight-chain or branched alkyl radical having from 2 to 8 carbon atoms, and
alkenyl and
alkenyl* are each, independently of one another, a straight-chain or branched alkenyl radical having from 2 to 8 carbon atoms.

46. A medium according to claim 45, wherein X is F, Cl, SF₅, NCS, or a halogenated alkyl radical having up to 8 carbon atoms, in which one or more CH₂ groups may, in each case independently, be replaced by —O— or —CH═CH— in such a way that O atoms are not linked directly to one another.

* * * * *

UNITED STATES PATENT AND TRADEMARK OFFICE
CERTIFICATE OF CORRECTION

PATENT NO. : 7,033,652 B2
APPLICATION NO. : 10/290292
DATED : April 25, 2006
INVENTOR(S) : Michael Heckmeier et al.

It is certified that error appears in the above-identified patent and that said Letters Patent is hereby corrected as shown below:

Column 85, line Formula I1 at line 35, reads

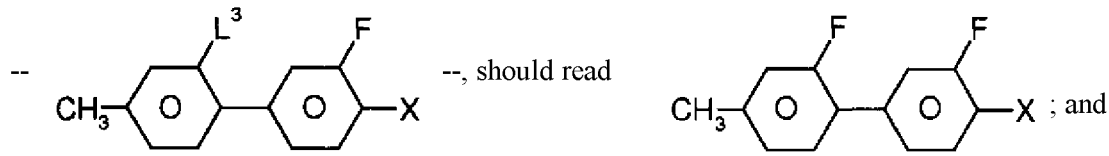

The formulas at column 102, line 35 through column 103, line 19 should be replaced with the following:

RXII

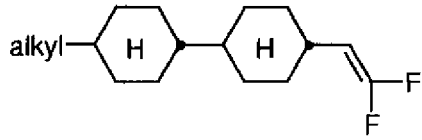

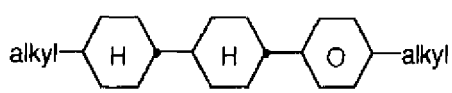
RXIII
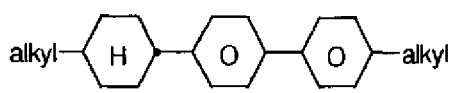
RXIV
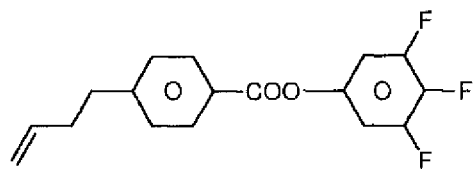
RXV